(12) United States Patent
Kenyon et al.

(10) Patent No.: US 7,794,957 B2
(45) Date of Patent: Sep. 14, 2010

(54) EUKARYOTIC GENES INVOLVED IN ADULT LIFESPAN REGULATION

(75) Inventors: Cynthia Kenyon, San Francisco, CA (US); Javier Apfeld, San Francisco, CA (US); Andrew Dillin, Oakland, CA (US); Delia Garigan, San Francisco, CA (US); Ao-Lin A. Hsu, Albany, CA (US); Josh Lehrer-Graiwer, San Francisco, CA (US); Coleen Murphy, San Francisco, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 11/282,262

(22) Filed: Nov. 18, 2005

(65) Prior Publication Data

US 2006/0162002 A1    Jul. 20, 2006

Related U.S. Application Data

(63) Continuation of application No. 10/179,766, filed on Jun. 24, 2002, now abandoned.

(60) Provisional application No. 60/373,975, filed on Apr. 18, 2002, provisional application No. 60/301,052, filed on Jun. 25, 2001, provisional application No. 60/300,577, filed on Jun. 22, 2001.

(51) Int. Cl.
*G01N 33/567* (2006.01)
*G01N 33/53* (2006.01)
*C12N 5/00* (2006.01)
*A01N 61/00* (2006.01)
*C07K 1/00* (2006.01)

(52) U.S. Cl. .................. 435/7.21; 435/7.1; 435/325; 514/1; 530/350

(58) Field of Classification Search ................ 435/7.1, 435/7.21, 325; 514/1; 530/350
See application file for complete search history.

(56) References Cited

U.S. PATENT DOCUMENTS

| | | | |
|---|---|---|---|
| 5,744,300 | A | 4/1998 | Linskens et al. |
| 5,945,330 | A | 8/1999 | Hillman et al. |
| 5,965,543 | A | 10/1999 | Campisi et al. |
| 6,225,120 | B1 | 5/2001 | Ruvkun et al. |
| 6,319,708 | B1 | 11/2001 | Chalfie et al. |
| 6,406,853 | B1 | 6/2002 | Spindler |
| 6,653,326 | B1 * | 11/2003 | Vigh et al. .......... 514/318 |
| 2001/0016332 | A1 | 8/2001 | Ruvkun et al. |
| 2001/0029617 | A1 | 10/2001 | Ruvkun et al. |
| 2002/0007496 | A1 | 1/2002 | Rothman et al. |
| 2002/0098495 | A1 | 7/2002 | Burmer et al. |
| 2003/0082597 | A1 | 5/2003 | Cannon et al. |

FOREIGN PATENT DOCUMENTS

| | | |
|---|---|---|
| WO | WO 99/32619 A1 | 7/1999 |
| WO | WO 01/12851 A2 | 2/2001 |
| WO | WO 02/14552 A2 | 2/2002 |
| WO | WO 02/059310 A2 | 8/2002 |
| WO | WO 03/000861 A2 | 1/2003 |

OTHER PUBLICATIONS

Liu et al., 1996, EXS, vol. 77, p. 393-407.*
Tatar, M., 1999 (American Zoologist, vol. 39, p. 920-927.*
Tyner, et al.; "p53 Mutant Mice That Display Early Ageing-Associated Phenotypes", Nature, vol. 415, pp. 45-53, (Jan. 3, 2002).
Knight, J., "The Biochemistry of Aging", Advances in Clinical Chem., vol. 35, pp. 11-62, (2001).
Nehlin, et al., "The Werner Syndrome, A Model for the Study of Human Aging", Annals of the New York Academy of Sciences, vol. 908, pp. 167-179 (2000).
Lithgow, et al., "Thermotolerance and Extended Life-Span Conferred by Single-Gene Mutations and Induced by Thermal Stress", Proc. Natl. Acad. Sci., USA, vol. 92, pp. 7540-7544, (Aug. 1995).
Tsang, et al., "Mitochondrial Respiratory Chain Deficiency in *Caenorhabditis elegans* Results in Developmental Arrest and Increased Life Span", Jour. of Biol. Chem., vol. 276, No. 34, pp. 32240-32246, (2001).
Kamath, et al., "Effectiveness of Specific RNA-Mediated Interference Through Ingested Double-Stranded RNA in *Caenorhabditis elegans*", Genome Biol. vol. 2, No. 1, pp. 1-10, (Dec. 20, 2000).
Apfeld, et al., "Cell Nonautonomy of *C. Elegans* DAF-W Functions in the Regulation of Diapause and Life Span", Cell, vol. 95, pp. 199-210, (Oct. 16, 1998).
Cahill, et al., "Phosphatidylinositol 3-Kinase Signaling Inhibits DAF-16 DNA Binding and Function Via 14-3-3-Dependent and 14-3-3-Independent Pathways", The Jour. of Biol. Chem, vol. 276, No. 16, pp. 13402-13410, (2001).
Lin, et al., "Regulation of the *Caenorhabditis elegans* Longevity Protein DAF-16 by Insulin/IGF-1 and Germline Signaling", Nature Genetics, vol. 28, pp. 139-145, (Jun. 2001).
Honda, et al., "The DAF-2 Gene Network for Longevity Regulates Oxidative Stress Resistance and MN-Superoxide Dismutase Gene Expression in *Caenorhabditis elegans*", The FASEB Jour., vol. 13, pp. 13851393, (Aug. 1999).
Anisimov, V.N., "Mutant and Genetically Modified Mice As Models for Studying the Relationship Between Aging and Carcinogenesis", Mechanisms of Ageing and Development, vol. 122, pp. 1221-1255, (2001).
Boulianne, G., "Neuronal Regulation of Lifespan: Clues From Flies and Worms", Mechanisms of Ageing and Development, vol. 122, pp. 883-894, (2001).
Garigan, et al., "Identifying and Characterizing New Lifespan Genes in *C. elegans*", Abstract No. 121, West Coast Worm Meeting, (1998).
Alcedo, et al., "Identification and Characterization of Long-Lived Mutants in *C. elegans*", Abstract 144, International Worm Meeting, (1999).
Dillin, et al., "Temporal Regulation of Aging in the Nematode *C. elegans*", West Coast Worm Meeting (2000).

(Continued)

*Primary Examiner*—Shin-Lin Chen
(74) *Attorney, Agent, or Firm*—Townsend and Townsend and Crew LLP

(57) ABSTRACT

The present invention relates to regulation of adult lifespan in eukaryotes. More particularly, the present invention is directed to methods of assaying for activators of the heat shock factor 1 (HSF-1) protein, which increases lifespan when overexpressed in an organism.

4 Claims, 12 Drawing Sheets

OTHER PUBLICATIONS

Dillin< et al., "Two Pathways for the Regulation of Lifespan by Metabolic Genes in *C. elegans*", Abstract 313, International Worm Meeting (2001).

Murphy, et al., "Gene Expression Analysis of *C. elegans* Lifespan Mutants", Abstract 331, International Worm Meeting (2001).

Garigan, et al., "Characterization of a Short-Lived *C. elegans* Mutant",Abstract 854, International Worm Meeting (2001).

Lin, et al., "Expression and Regulation of DAF-16::GFP Constructs", Abstract 183, West Coast Worm Meeting (2000).

Hill, et al., "Genomic Analysis of Gene Expression in *C. elegans*", Science, vol. 290, pp. 809-812 (Oct. 27, 2000).

Apfeld, et al., "Regulation of Lifespan by Sensory Perception in *Caenorhabditis elegans*", Nature, vol. 402, pp. 804-809 (Dec. 16, 1999).

Kenyon, C., "A Conserved Regulatory System for Aging", Cell, vol. 105, pp. 165-168, (Apr. 20, 2001).

Dillin, et al., "Rates of Behavior and Aging Specified by Mitochondrial Function During Development", Science, vol. 298, pp. 2398-2401, (Dec. 20, 2002).

Dillin, et al, "Timing Requirements for Insulin/IGF-1 Signaling in *C. elegans*", Science, vol. 298, pp. 830-834, (Oct. 25, 2002).

Hsin, et al., "Signals From the Reproductive System Regulate the Lifespan of *C. elegans*", Nature, vol. 399, pp. 362-366 (May 27, 1999).

Tatar, et al., "Chaperoning Extended Life", Nature, vol. 390, p. 30, (Nov. 6, 1997).

Garigan, et al., "Genetic Analysis of Tissue Aging in *Caenorhabditis elegans*: A Role for Heat-Shock Factor and Bacterial Proliferation", Genetics, vol. 161, pp. 1101-1112 (Jul. 2002).

Guarente, et al., "Genetic Pathways That Regulate Ageing in Model Organisms", Nature, vol. 408, pp. 255-262, (Nov. 9, 2000).

Yokoyama, et al., "Extended Longevity of *Caenorhabditis elegans* by Knocking in Extra Copies of HSP70F, A Homolog of MOT-2 (Mortalin)/MTHSP70/GRP75", FEBS Letters, vol. 516, pp. 53-57 (2002).

Migliaccio, et al., "The P66$^{SHC}$ Adaptor Protein Controls Oxidative Stress Response and Life Span in Mammals", Nature, vol. 402, pp. 309-313, (Nov. 18, 1999).

Klass, M.R., "Aging in the Nematode *Caenorhabditis elegans*: Major Biological and Environmental Factors Influencing Life Span", Mechanism of Ageing and Development, vol. 6, pp. 413-429, (1977).

Fraser, et al., "Functional Genomic Analysis of *C. elegans* Chromosome I by Systematic RNA Interference", Nature, vol. 408, pp. 325-330 (Nov. 16, 2000).

Benedictis, et al., "Recent Advances in Human Gene-Longevity Association Studies", Mechanisms of Ageing and Development, vol. 122, pp. 909-920 (2001).

Jazwinski, S. Michael, "Metabolic Control and Ageing", TIG, vol. 16, No. 11, pp. 506-511, (2000).

Campisi, J., "From Cells to Organisms: Can We Learn About Aging From Cells in Culture?", Experimental Gerontology, vol. 36, pp. 607-618 (2001).

"The Search for Genes That Control the Rate of Aging", CSI Press, *C. elegans II*, Chap. 28, Book Viewer, pp. 1-12. (Jan. 3, 2002).

Fire, Andrew et al.; "Potent and specific genetic interference by double-stranded RNA in *Caenorhabditis elegans*"; 1998, Nature, vol. 391, pp. 806-811.

Blake et al., "A Molecular Marker Confirms That the Rate of Adult Maturation Is Largely Independent of the Rate of Pre-Adult Development in *Drosophila melanogaster*", Dev Genetics 18:125-130 (1996).

Blake et al., "Changes in gene expression during post-eclosional development in the olfactory system of *Drosophila melanogaster*", Mech. Dev. 52:179-185 (1995).

Dozmorov et al., "Age-associated decline in responses of naïve T cells to in vitro immunization reflects shift in glucocorticoid sensitivity", Life Sci. 64(20):1849-1859 (1999).

Dozmorov et al., "Array-based expression analysis of mouse liver genes: effect of age and of the longevity mutant Prop $I^{df}$", J Gerontol Biol Sci. 56A(2):B72-B80 (2001).

Dozmorov et al., "Gene expression profile of long-lived snell dwarf mice", J Gerontol Biol Sci. 57A(3):B99-B108 (2002).

Fleming et al., "Role of oxidative stress in *Drosophila* aging", Mutation Research 275:267-279 (1992).

Hayflick, "The future of ageing", Nature 408:267-269 (2000).

Helfand et al., "Regulation of Gene Expression During Aging", Res. And Prob. In Cell Diff. 29:67-80 (2000).

Helfand et al., "Temporal Patterns of Gene Expression in the Antenna of the Adult *Drosophila melanogaster*", Genetics 140:549-555 (1995).

Helfand et al., "The expression of a reporter protein, β-galactosidase, is preserved during maturation and aging in some cells of the adult *Drosophila melanogaster*", Mech. Dev. 55:45-51 (1996).

Heymes et al., "Cardiac Senescence Is Associated with Enhanced Expression of Angiotensin II Receptor Subtypes", Endocrinology 139(5):2579-2587 (1998).

Jackson et al., "Mouse loci associated with life span exhibit sex-specific and epistatic effects", J Gerontol Biol Sci. 57A:B9-B15 (2002).

King et al., "Aging-Specific Expression of *Drosophila* hsp22", Dev. Biol. 207:107-118 (1999).

Kirk et al., "Age-related decline in activation of JNK by TCR- and CD28-mediated signals in murine T-lymphocytes", Cell. Immunol. 197:75-82 (1999).

Kirk et al., "Age-sensitive and -insensitive pathways leading to JNK activation in mouse CD4$^+$T-cells", Cell. Immunol. 197:83-90 (1999).

Kirk et al., "Analysis of Raf-1 activation in response to TCR activation and costimulation in murine T-lymphocytes: effect of age", Cell. Immunol. 190:33-42 (1998).

Kurapati et al., "Increased hsp22 RNA Levels in *Drosophila* Lines Genetically Selected for Increased Longevity", J. Gerontol Biol Sci. 55A(11):B552-B559 (2000).

Miller, "Biochemical and genetic analyses of T cell aging in mice", Springer Semin Immunopathol 24:61-73 (2002).

Miller, "Biomarkers of aging: prediction of longevity by using age-sensitive T-cell subset determinations in a middle-aged, genetically heterogeneous mouse population", J Gerontol Biol Sci. 56A(4):B180-B186 (2001).

Miller, "Effect of aging on T lymphocyte activation", Vaccine 18:1654-1660 (2000).

Miller, "Genes for ageing? Keystone Symposium: Ageing: Genetic and Environmental Influences on Life Span, Durango, Colorado, USA, Feb. 2-7, 1999", Trends in Genetics 15(5):175-176 (1999).

Miller, "New paradigms for research on aging and late-life illness", Mech Ageing Dev. 122:130-132 (2001).

Miller, "Telomere diminution as a cause of immune failure in old age: an unfashionable demurral", Biochem Soc Trans 28(2):241-245 (2000).

Miller, "The aging immune system: subsets, signals, and survival", Aging Clin. Exp. Res. 9(4 Suppl):23-24 (1997).

Miller et al., "Differential longevity in mouse stocks selected for early life growth trajectory", J Gerontol Biol Sci. 55A(9):B455-B461 (2000).

Miller et al., "Genetics of aging and immunity", Aging Clin. Exp. Res. 10(2):154-155 (1998).

Miller et al., "Interpretation, design, and analysis of gene array expression experiments", J Gerontol Biol Sci. 56A(2):B52-B57 (2001).

Miller et al., "Longer life spans and delayed maturation in wild-derived mice", Exp Biol Med 227(7):500-5088 (2002).

Mosley et al., "Idiosyncratic alterations of TCR size distributions affecting both CD4 and CD8 T cell subsets in aging mice", Cell. Immunol. 189:10-18 (1998).

Rogina et al., "Cu, Zn superoxide dismutase deficiency accelerates the time course of an age-related marker in *Drosophila melanogaster*", Biogerontology 1:163-169 (2000).

Rogina et al., "*Drosophila drop-dead* mutations accelerate the time course of age-related markers", Proc. Natl. Acad. Sci. USA 94:6303-6306 (1997).

Rogina et al., "Extended Life-Span Conferred by Cotransporter Gene Mutations in *Drosophila*", Science 290:2137-2140 (2000).

Rogina et al., "Regulation of Gene Expression Is Linked to Life Span in Adult *Drosophila*", Genetics 141(3):1043-1048 (1995).

Rogina et al., "Regulation of gene expression is preserved in aging *Drosophila melanogaster*", *Current Biology* 8:475-478 (1998).

Rogina et al., "Spatial and temporal pattern of expression of the *wingless* and *engrailed* genes in the adult antenna is regulated by age-dependent mechanisms", *Mech. Dev.* 63:89-97 (1997).

Rogina et al., "Timing of Expression of a Gene in the Adult *Drosophila* Is Regulated by Mechanisms Independent of Temperature and Metabolic Rate", *Genetics* 143:1643-1651 (1996).

Roth et al., "Biomarkers of Caloric Restriction May Predict Longevity in Humans", *Science* 297:811 (2002).

Salehi et al., "Age-related changes in gene expression in the rat brain revealed by differential display", *Experientia* 52:888-891 (1996).

Sun et al., "FLP Recombinase-Mediated Induction of Cu/Zn-Superoxide Dismutase Transgene Expression Can Extend the Life Span of Adult *Drosophila melanogaster* Flies", *Mol. Cell. Biol.* 19:216-228 (1999).

Tamir et al., "Age-dependent alterations in the assembly of signal transduction complexes at the site of T cell/APC interaction", *J. Immunol.* 165:1243-1251 (2000).

Tower, "Aging mechanisms in fruit flies", *BioEssays* 18(10):799-807 (1996).

Tower, "Transgenic methods for increasing *Drosophila* life span", *Mech Ageing Dev.* 118:1-14 (2000).

Yokoyama, K. et, "Extended Longevity of *Caenorhabditis elegans* by Knocking in Extra Copies of hsp70f, a homolog of mot-2 (mortalin)/mthsp70/Grp75", Federation of European Biochemical Societies, 2002, 53-57, 516, Japan.

\* cited by examiner

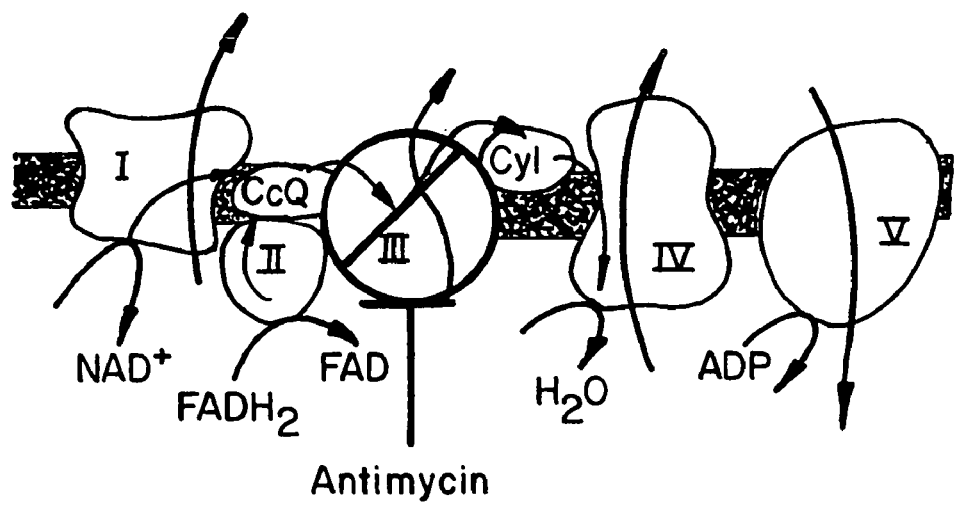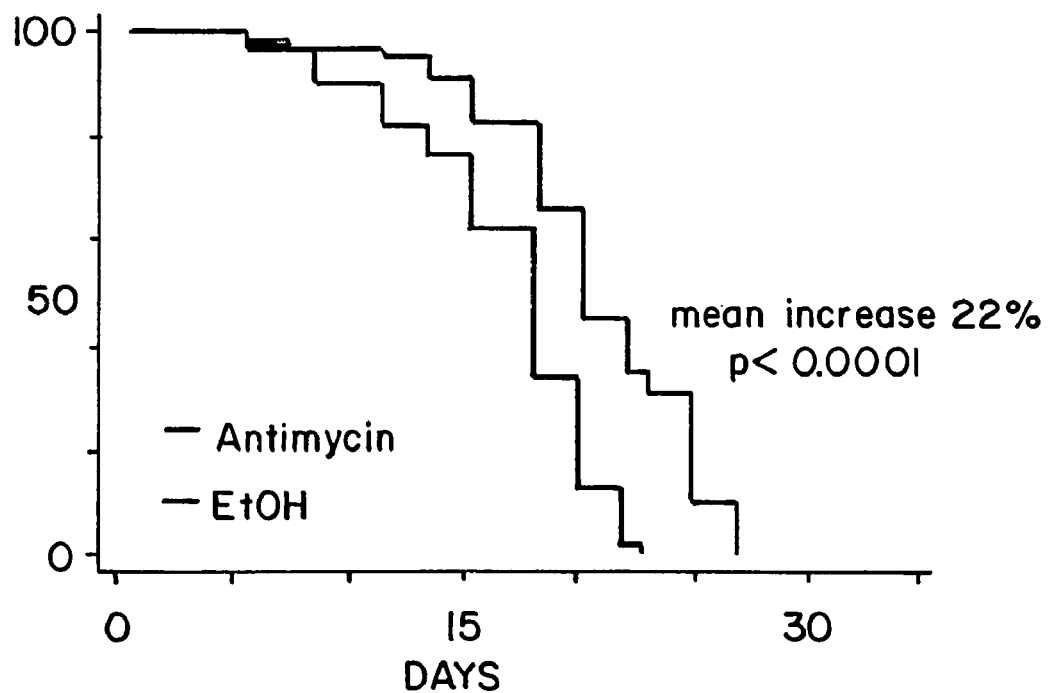
FIG. 3.

Group 1: Genes that are upregulated in *daf-2(-)* worms

Oxidative stress protection
sod-3: Manganese superoxide dismutase
ctl-1: cytosolic catalase
ctl-2: Peroxisomal catalase
● mtl-1: Metallothionein; cadmium-binding
glutathione S-transferase protein family-2
● hsp-12.6, sip-1, hsp-16.1, hsp-16.11

Steroid metabolism/lipid synthesis
● CytP450 heme-thiolate protein family-3
UDP-glucuronosyltransferase protein family-4
estradiol 17 beta-dehydrogenase-2
fat-6: stearoyl-CoA delta-9 fatty acid desaturase
fat-7: stearoyl-CoA delta-9 fatty acid desaturase
fat-3: delta6-fatty acid-desaturase activity
ASAH acid ceramidase
aminopeptidases--many
Carboxypeptidases--many Proteolysis
ges-1: Carboxylesterase expressed in gut cells
gcp-1: Cysteine protease expressed in the intestine
cathepsin Z-like cysteine protease Metabolic
acyl-CoA synthetase
alcohol dehydrogenase
Malate synthase 1/isocitrate lyase
acyl CoA dehydrogenase
hydroxyacyl-CoA dehydrogenase
dao-3: C1-tetrahydrofolate synthase
trehalase
trehalose-6-phosphate synthase
acyl-CoA oxidase Antibacterial, antifungal
Thaumatin-like antifungal-3
Bactericidal amoebapores; antibacterial agent
Pathogen-related in yeast (PRY) protein family
N-acetylmuraminidase-2

Many unknown genes/
members of unknown families

*FIG. 5.*

Group 2: Genes downregulated in *daf-2* mutants

Neuronal

- similarity to human ASMTL protein, acetylserotonin N-methyltransferase-like protein
  Putative G protein-coupled receptor, no homolog found in human or D. melanogaster
  gcy-18: Protein with a cytoplasmic receptor tyrosine kinase domain and a guanylate cyclase domain, has strong similarity to human natriuretic peptide receptor NPR1
  gcy-6: Putative guanylyl cyclase expressed in the ASEL neuron Other (most are unidentified)

- vitellogenins
  nhr-64: Member of the nuclear hormone receptor/Zinc finger protein family
  pep-2: Member of the proton-coupled oligopeptide transporter superfamily
  mtl-2: Metallothionein-related, cadmium-binding protein
  lbp-7: Member of the fatty acid-binding protein family
  aminopeptidases--many
  Carboxypeptidases--many

- ins-7: Insulin-related protein of the type-beta subfamily

*FIG. 9.*

EUKARYOTIC GENES INVOLVED IN ADULT LIFESPAN REGULATION

CROSS-REFERENCES TO RELATED APPLICATIONS

The present application is related to U.S. Ser. No. 60/300,577, filed Jun. 22, 2001, U.S. Ser. No. 60/301,052, filed Jun. 25, 2001, and U.S. Ser. No. 60/373,975, filed Apr. 18, 2002, each herein incorporated by reference in their entirety.

STATEMENT AS TO RIGHTS TO INVENTIONS MADE UNDER FEDERALLY SPONSORED RESEARCH AND DEVELOPMENT

This invention was made with government support under Grant No. NIH AG11816, awarded by the NIH. The government has certain rights in this invention.

FIELD OF THE INVENTION

The present invention relates to regulation of lifespan in eukaryotes. More particularly, one aspect of the present invention is directed to methods of assaying for genes, gene products, and genes in pathways controlled by such genes and gene products, using RNAi and microarray analysis, that regulate lifespan (e.g., extend or truncate adult lifespan) in eukaryotes such as invertebrates (e.g., *C. elegans*), plants, and mammals, e.g., humans. For example, one aspect of the present invention is directed to genes, in particular human genes, encoding components of the mitochondrial respiratory chain and genes encoding glycolysis enzymes, which are involved in lifespan regulation, and genes and gene products in pathways controlled by such genes. Other genes and gene products identified as regulating aging and aging pathways include a gene encoding a GTPase; a transcriptional activator; novel genes: llw-1, llw-2, llw-3, and llw-4; genes encoding cytochrome P450 proteins (involved in steroid biosynthesis); a melatonin synthesis gene; genes encoding insulin and insulin-like peptides; genes encoding heat shock factors; genes encoding catalases; stress-response genes; and metabolic genes. The invention further relates to methods for identifying and using agents, including small molecule chemical compositions, antibodies, antisense nucleic acids, and ribozymes, that regulate, e.g., enhance, adult lifespan via modulation of aging associated proteins; as well as to the use of expression profiles, markers, and compositions in diagnosis and therapy related to lifespan extension, life expectancy, and aging. The present invention also relates to gene therapy involving lifespan associated genes.

BACKGROUND OF THE INVENTION

Previously, classic genetic screens have been used to identify genes involved in the *C. elegans* development. In one example, inhibition of mitochondrial respiratory chain genes such as NADH ubiquinone oxidoreductase and ATP synthase in *C. elegans* larva was found to impair larval development and cause arrest in the third larval stage (see, e.g., Tsang et al., *JBC* 276:33240-33246 (2001)). In other examples, classical genetic screens have been used to identify *C. elegans* genes involved in a variety of processes, including dauer formation, and embryonic development. Some of these genes, for example the daf-2 and daf-16 genes, have been implicated in the regulation of lifespan see, e.g., Kenyon et al., *Nature* 366:461-464 (1993); Morris et al., *Nature* 382:536-539 (1996); Kimura et al., *Science* 277:942-946 (1997); Paradis et al., *Genes Dev.* 12:2488-2498 (1998); Paradis et al., *Genes Dev.* 13:1438-1452 (1999); Off & Ruvkun, *Mol. Cell* 2:886-893 (1998); Guarente & Kenyon, *Nature* 408:255-262 (2000); Ogg et al., *Nature* 389:994-999 (1997); and Lin et al., *Science* 278:1319-1322 (1997)).

Classical genetic screens are frequently time consuming, both in identification of interesting mutants and in cloning a gene associated with a mutation. Classical genetic screens can include labor intensive backcrosses to eliminate mutations unlinked to the phenotype of interest. Classical genetic screens also may require the extra step of cloning the gene of interest, by complementation of the mutation.

Many different genes likely regulate the process of aging in eukaryotes and their identification will aid in understanding the process. Regulation of biological processes is frequently conserved between divergent organisms. For example, cell cycle proteins and their mechanism of action are conserved between organisms as divergent as yeast and humans. Thus, regulatory mechanisms identified in a genetically tractable organism can be used to predict and identify homologous genes and gene products that regulate similar biological processes in higher eukaryotes. However, even in genetically tractable organisms, such as *C. elegans*, classical genetic methods are frequently labor intensive and cumbersome for identification of interesting mutants and for isolation of a gene of interest. The present invention solves these and other problems.

SUMMARY OF THE INVENTION

The present invention provides, for the first time, methods of assaying for aging associated genes and proteins using RNAi, as well as aging associated genes and proteins so identified. Double-stranded RNA libraries are administered to a test organism or cell, e.g., *C. elegans*. For administration to *C. elegans*, the RNAi library can be expressed in a bacterial cell and fed to the *C. elegans*. Age-associated mutants (those that live longer or age faster) are identified by measuring lifespan increase or decrease, or an age-associated parameter such as stress resistance or a Nomarski analysis indicia, e.g., yolk accumulation, loss of ability to chew and expel (distended oral and anal cavities), necrotic cavities in tissue, curdled appearing tissue, and germ cell appearance (graininess, large, well separated nuclei, fewer nuclei, and cavities).

Other methods can be used to identify age-associated genes and gene products, including microarray analysis, database profiling with known age-associated genes, mammalian complementation assays, yeast two hybrid assays, immunoprecipitation, etc.

The use of dsRNA has identified a number of genes and gene products which, when inhibited by dsRNA, results in longer lifespans, e.g., phosphoglucose isomerase, cytochrome C1, NADH oxidoreductase, ATP synthase, cytochrome. C oxidase, a GTPase, and four novel genes, llw1-4 (see also Tables 5 and 6). Thus, compounds that inhibit such genes and gene products, as well as genes in a pathway controlled by such genes and gene products, would be useful for increasing lifespan and modulating the aging process in eukaryotes, e.g., plants, mammals, humans. The genes identified herein include any mammalian or human homologs thereof.

In addition, the use of dsRNA has identified genes and gene products which, when inhibited by dsRNA, results in a shorter lifespan, e.g., heat shock protein or heat shock factor (HSF) (see also Table 5 and Table 6). Overexpression of HSF has also been shown to increase lifespan in *C. elegans*. Thus, compounds that activate heat shock proteins or genes such as HSf-1 or HSF targets, or genes or gene products controlled by HSF, or genes that respond to stress and activate HSF would be useful for increasing lifespan and modulating the aging process in eukaryotes, e.g., plants, mammals, humans. In one example, compounds such as zinc finger proteins (naturally occurring or recombinant) can be used to bind to HSF binding regions on genes and alter expression of HSF-controlled genes (see, e.g., U.S. Pat. Nos. 5,789,538 and 6,242,568).

Microarrays were used to analyze gene expression profiles in daf-2 and daf-16 mutants and identify genes and gene products involved in lifespan regulation. The expression of a number of genes varied (by over- or under-expression) in long-lived (daf-2) or short-lived (daf-16 and daf-16; daf-2) *C. elegans* mutants (see Table 5). The activity of genes identified using microarray analysis was then modulated using RNAi (Table 6). The genes thus identified include hormones that activate the daf-2 pathway, several encoding cytochrome P450 proteins (involved in steroid biosynthesis), the melatonin synthesis gene, insulin and insulin-like peptides, heat shock factors, catalases, stress-response genes, and metabolic genes. These genes and gene products, and genes and gene products controlled by these genes (e.g., steroid hormones, melatonin) are therefore useful for developing drugs to regulate aging in eukaryotes, e.g., plants, mammals, humans. In addition, these genes can be used as markers for the insulin/IGF system activity, as markers for the aging process, and as markers that indicate the likely longevity of an individual.

In one aspect of the invention, nucleic acids from *C. elegans* and corresponding mammalian genes (e.g., human) encoding glycolysis proteins, e.g., phosphoglucose isomerase, and mitochondrial respiratory chain proteins, e.g., cytochrome C1 component of complex III (CYC1), NADH oxidoreductase (NUO2), ATP synthase (ATP3, a member of the ATP synthase delta family), and cytochrome C oxidase (CCO1), are provided, as are nucleic acids from *C. elegans* and corresponding mammalian genes encoding a GTPase associated with aging; a transcriptional activator, heat shock factors, e.g., HSF-1; novel proteins LLW-1, LLW-2, LLW-3, and LLW-4; cytochrome P450 proteins, a melatonin synthesis gene, insulin and insulin-like peptides, heat shock factors, catalases, stress-response genes, and other genes listed in Tables 5 and 6. In another aspect, the present invention provides nucleic acids, such as probes, antisense oligonucleotides, and ribozymes, that hybridize to glycolysis genes, e.g., phosphoglucose isomerase (GPI-1); mitochondrial respiratory chain genes, e.g., cytochrome C1, NADH oxidoreductase, ATP synthase, and cytochrome C oxidase; a GTPase associated with aging; a transcriptional activator, heat shock factors, e.g., HSF-1; novel genes llw-1, llw-2, llw-3, and llw-4; cytochrome P450 proteins, a melatonin synthesis gene, insulin and insulin-like peptides, heat shock factors, catalases, stress-response genes, and other genes listed in Tables 5 and 6.

In another aspect, the invention provides expression vectors and host cells comprising nucleic acids encoding glycolysis proteins, e.g., phosphoglucose isomerase; mitochondrial respiratory chain proteins, e.g., cytochrome C1, NADH oxidoreductase, ATP synthase, and cytochrome C oxidase; a GTPase associated with aging; a transcriptional activator, heat shock factors, e.g., HSF-1; novel genes llw-1, llw-2, llw-3, and llw-4; cytochrome P450 proteins, a melatonin synthesis gene, insulin and insulin-like peptides, heat shock factors, catalases, stress-response genes, and other genes listed in Tables 5 and 6. In another aspect, the present invention provides glycolysis proteins, e.g., phosphoglucose isomerase; mitochondrial respiratory chain proteins, e.g., cytochrome C1, NADH oxidoreductase, ATP synthase, and cytochrome C oxidase; a GTPase associated with aging; a transcriptional activator, the heat shock factor; novel proteins LLW-1, LLW-2, LLW-3, LLW-4; cytochrome P450 proteins, a melatonin synthesis protein, insulin and insulin-like peptides, heat shock factors, catalases, stress-response proteins, and other gene products listed in Tables 5 and 6 and antibodies thereto.

In another embodiment, the invention provides heterologous constructs comprising an age-associated gene as described herein, and a heterologous sequence such as a regulatory region, a reporter gene, a purification tag, e.g., for production of a fusion protein, for purification of a gene product, for more efficient expression of the gene or gene product, or for regulated expression of the gene.

In one embodiment, methods known to those of skill in the art such as RT-PCR, northern, Southern analysis, cDNA and genomic library cloning, etc. can be used to identify eukaryotic orthologs, e.g., invertebrate, vertebrate, plant, mammalian, and human orthologs, of the age-associated proteins provided herein. In another embodiment, computer sequence analysis can be used to identify orthologs. Such methods optionally include the step of assessing an age associated parameter in a cell in which the suspected ortholog is perturbed.

In one embodiment, endogenous or recombinant gene products of the age associated genes described herein are purified using the methods described herein, to at least about 50% purity, preferably 60%, 70%, 80%, 90% or higher purity. In another embodiment, the present invention provides a reaction mixture comprising an age-associated protein and another component such as a test compound, an antibody, a peptide, etc.

In another aspect, the present invention provides a method for identifying a compound that modulates adult aging, the method comprising the steps of: (i) contacting the compound with a glycolysis protein, e.g., phosphoglucose isomerase, or a mitochondrial respiratory chain protein, e.g., cytochrome C1, NADH oxidoreductase, ATP synthase, and cytochrome C oxidase or a GTPase associated with aging; a novel proteins LLW-1, LLW-2, LLW-3, LLW-4; and (ii) determining the functional effect, e.g., lifespan effect or another age-associated parameter of the compound upon the polypeptide.

In another aspect, the present invention provides a method for identifying a compound that modulates adult aging, the method comprising the steps of: (i) contacting the compound with protein encoded by a gene listed in Table 5 or 6; and (ii) determining the functional effect, e.g., lifespan effect or another age-associated parameter of the compound upon the polypeptide.

In another aspect, the present invention provides a method for identifying a compound that modulates adult aging, the method comprising the steps of: (i) contacting the compound with a heat shock factor and (ii) determining the functional effect, e.g., lifespan effect or another age-associated parameter, of the compound upon the polypeptide.

In one embodiment, the functional effect is a physical effect or a chemical effect. In another embodiment, the functional effect is a phenotypic effect. In one embodiment, the polypeptide is expressed in a eukaryotic host or host cell, e.g., *C. elegans*. In another embodiment, the functional effect is determined by measuring longevity, average lifespan, or mean lifespan of an organism contacted with a compound. In one embodiment, the functional effect is determined by measuring enzymatic activity. In one embodiment, the functional effect is determined by measuring transcriptional activation. In one embodiment, the organism is *C. elegans*. In another embodiment, the organism is mammalian host or cell, e.g., a mouse, a rat, a guinea pig, a monkey, or a human.

In another embodiment, compounds that modulate aging are identified using computer programs that model age-associated protein structure and determining compounds that bind or interact with the modeled protein. Optionally, the effect of the compound can be validated by examining its effect on a cell or organism expressing the modeled age-associated protein.

In another embodiment, the method comprises providing a sequence comprising an age-associated protein, altering the sequence, e.g., by mutagenesis, and assaying the protein encoded by the altered sequence.

In another aspect, the present invention provides a method of modulating lifespan in a subject, the method comprising the step of contacting the subject with an therapeutically effective amount of a compound identified using the methods described herein, e.g., a compound such as antimycin. In one embodiment, the subject is C. elegans. In another embodiment, the subject is a mammalian subject, e.g., a mouse, a rat, a guinea pig, a monkey, or a human. In one embodiment, the subject is a plant. In one embodiment, the compound is antimycin or an analog thereof.

In another aspect, the present invention provides a method of detecting the presence of a lifespan associated protein described herein, and the genes encoding such proteins in eukaryotic tissue, the method comprising the steps of: (i) isolating a biological sample; (ii) contacting the biological sample with a specific reagent that selectively associates with the protein of choice; and, (iii) detecting the level of specific reagent that selectively associates with the sample.

In one embodiment, the specific reagent is selected from the group consisting of: antibodies, oligonucleotide primers, and nucleic acid probes.

BRIEF DESCRIPTION OF THE DRAWINGS

FIG. 3 shows antimycin increases lifespan.

FIG. 5 shows certain genes identified using microarray analysis that are upregulated in daf-2(−) worms.

FIG. 9 shows certain genes identified using microarray analysis that are downregulated in daf-2 mutants.

DETAILED DESCRIPTION OF THE INVENTION

Introduction

Figure 1:
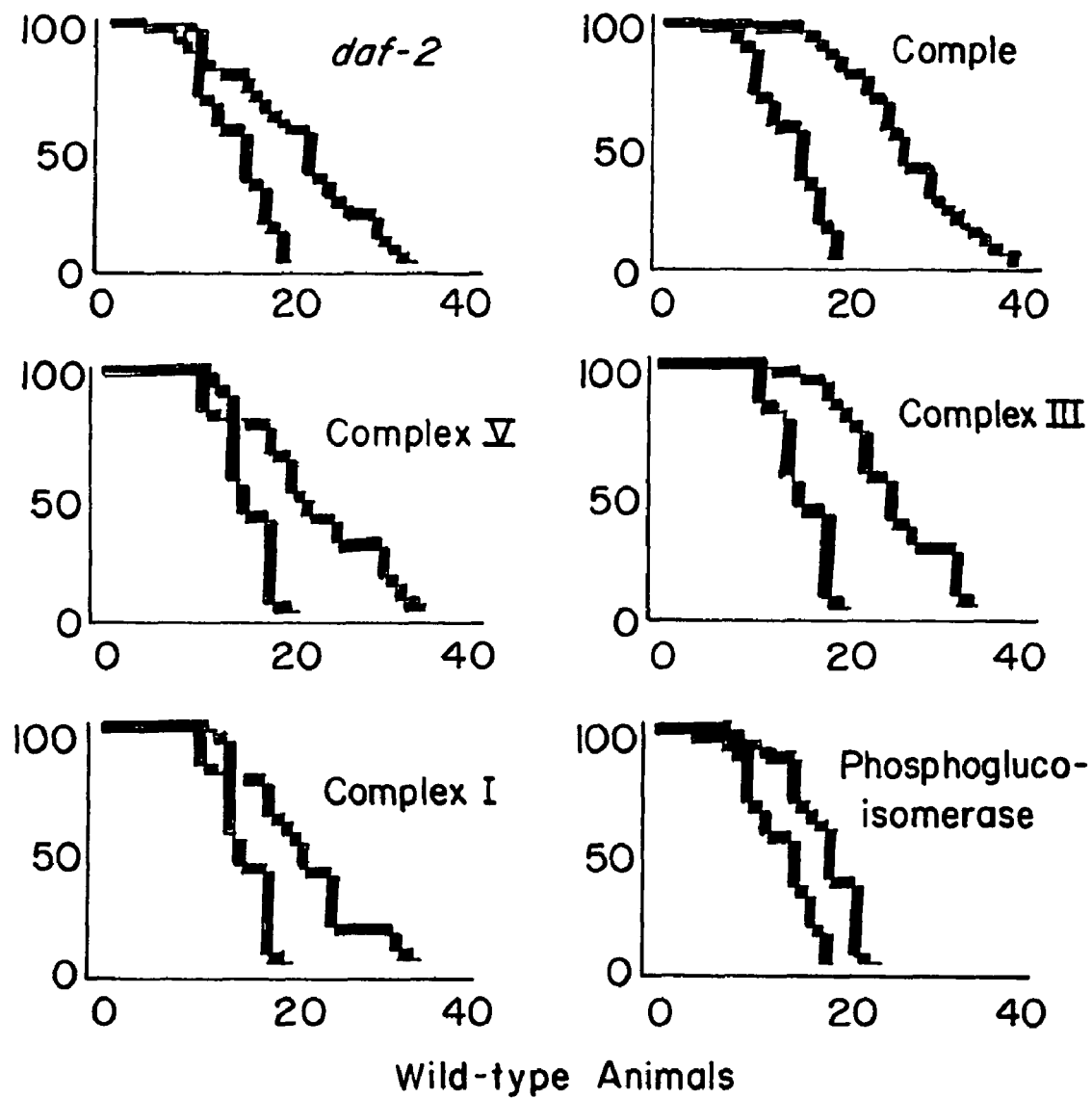
FIG. 1 shows RNAi of respiratory chain and glycolysis genes increasing lifespan.
Figure 2:
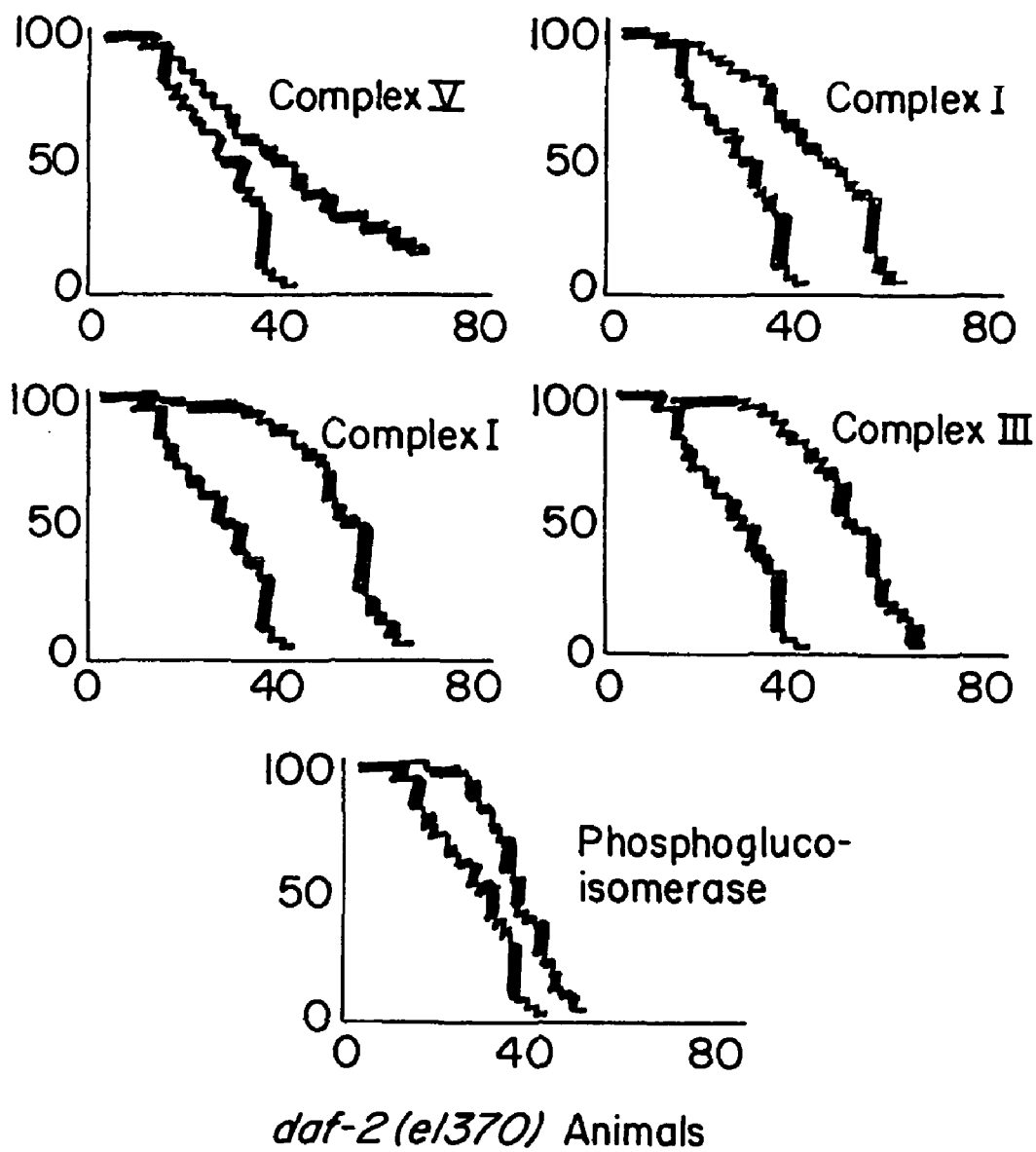
FIG. 2 shows daf-2(e1370) worms treated with dsRNAs of respiratory and glycolytic genes.
Figure 4:
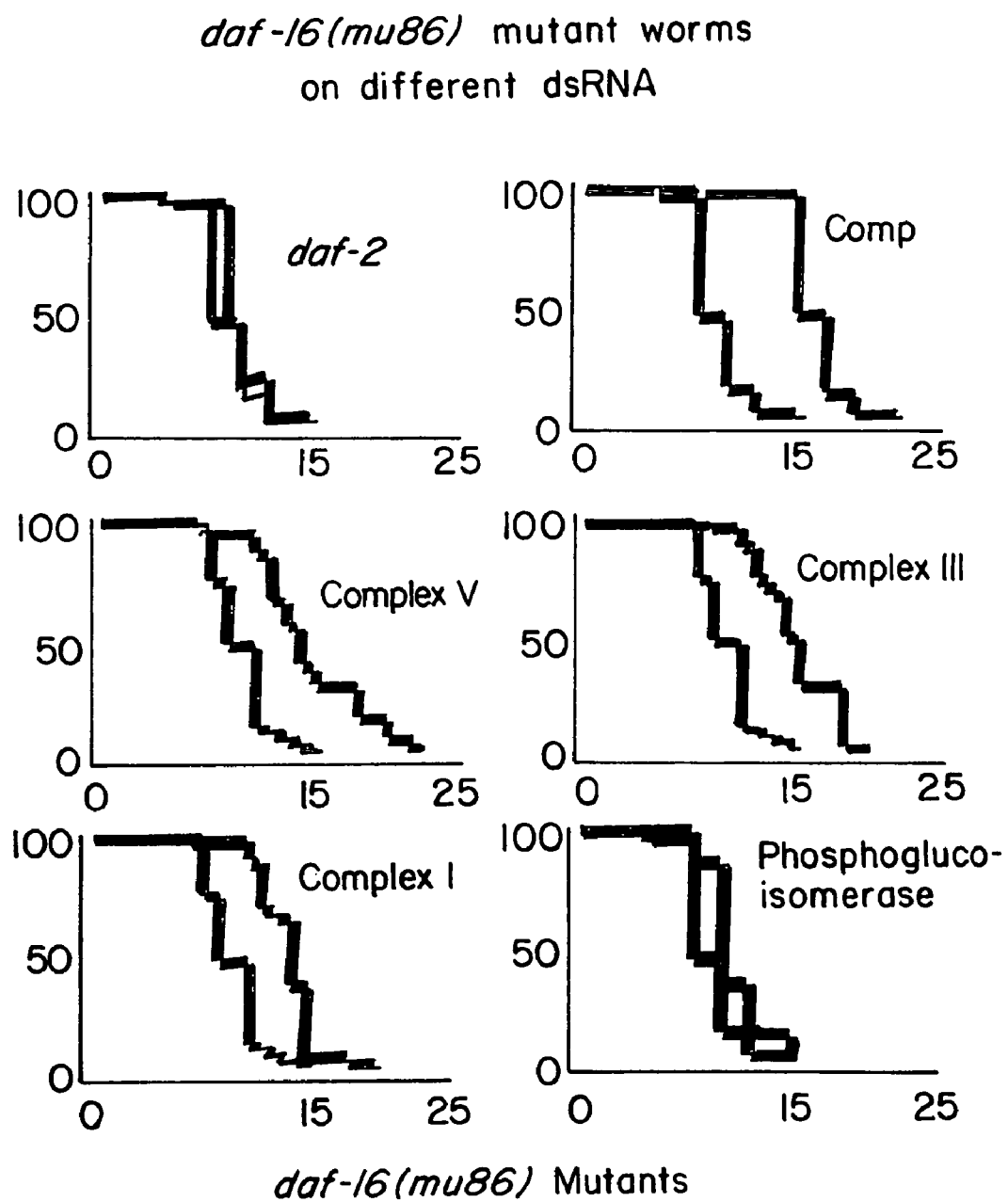
FIG. 4 shows daf-16(mu86) mutant worms treated with dsRNAs of respiratory and glycolytic genes.

Double-stranded RNA-mediated interference (RNAi) provides a sequence specific mechanism for inhibiting gene expression in C. elegans (see, e.g., Fire et al., Nature 391: 806-811 (1998) and WO 99/32619)). This technique is also useful for functional genomics analysis of C. elegans genes (see, e.g., Fraser et al., Nature 408:325-330 (2000); Kamath et al., Genome Biol. 2:RESEARCH0002 (2000)).

Surprisingly, RNAi can be used to identify genes and gene products involved in lifespan and aging mechanisms in adults, by feeding bacteria expressing a dsRNA library over long-term time periods to C. elegans and measuring, e.g., mean and median lifespan increase or decrease in adults. Such assays can be used, in addition, to determine if two or more genes function together in a similar aging pathway, to determine if gene function is cell autonomous, and to determine if drug compounds known to alter the aging process function in the same or different pathways. Microarray assays can also be used to identify genes and gene products involved in lifespan and aging (see, e.g., Table 5 and Table 6).

Microarray and RNAi assays are also useful in combination, e.g., by identifying a gene or gene product involved in lifespan using RNAi and then examining its expression pattern in old and young adults using microarray analysis, or by identifying a differentially expressed gene or gene product involved in lifespan using microarray analysis and then examining the effects of gene or gene product inhibition using RNAi. Microarray analysis can also be performed on animals treated with RNAi of genes identified using microarray analysis.

Using the technique of double-stranded RNA inhibition (RNAi), two types of metabolic genes and gene products have been found to regulate the adult lifespan of a model eukaryote, C. elegans. Inhibition of genes and gene products that function in the mitochondrial respiratory chain, including genes encoding cytochrome C1, cytochrome C oxidase and ATP synthetase, lengthen lifespan, as does inhibition of a gene that functions in glycolysis, glucose phosphate isomerase. However, these perturbations produce different phenotypes. Inhibition of respiratory chain components cause a Clk (clock) phenotype, including slow growth to adulthood, and, in adults, slow movement, and decreased pumping and defecation rates. In contrast, inhibition of glucose phosphate isomerase extends adult lifespan without producing a Clk phenotype. Together these findings indicate that at least two distinct pathways can regulate lifespan in response to changes in metabolic gene activities in eukaryotes. These RNAi-mediated phenotypes are examples of "reverse phenotypes," i.e., suppression or inhibition of the gene lengthens lifespan. For RNAi interventions that decrease lifespan, restoring gene expression should restore a normal lifespan. Therefore, under- and over-expression of lifespan genes, gene products and pathways, as well as activation or inhibition of lifespan gene, gene products, and pathways, can be used to modulate aging in a subject.

The present invention therefore provides nucleic acids from C. elegans encoding cytochrome C1 component of complex III, gene C54G4.8 (CYC1, SEQ ID NO:1, Accession No. CAA99820.1, which is 50% identical to human ortholog CYC1); NADH oxidoreductase, gene T10E9.7 (NUO2, SEQ ID NO:2, Accession No. AAB522474.1, which is 56% identical to human ortholog NDUFS3, Accession No. NM_004551); ATP synthase (delta family), gene F27C1.7 (ATP3, SEQ ID NO:3, Accession No. AAB37654.1, 43% identical to human ortholog ATP5O); and cytochrome C oxidase, gene F26E4.9 (CCO1, SEQ ID NO:4, Accession No. CAB03002.1, 35% identical to human ortholog COX5B, Accession No. NM_001862), which are protein components of the mitochondrial respiratory chain. The present invention also provides nucleic acids from C. elegans encoding glucose phosphate isomerase, gene Y87G2A.8 (GPI-1, SEQ ID NO:5, Accession No. CAB60430.1, 68% identical to human ortholog GPI, Accession No. NM_000175). The present invention also provides gene and gene products shown in Tables 5 and 6, and human homologs thereof. The present invention also provides homologs of these conserved proteins that are found in mammals, such as humans, and which are known to those of skill in the art. The invention therefore provides methods of screening for compounds, e.g., small molecules, antibodies, antisense molecules, and ribozyme, that are capable of modulating lifespan in adult eukaryotes, in particular, in mammals, e.g., for lifespan enhancement and treatment of premature aging.

Furthermore, it was discovered that administration of antimycin, a mitochondrial respiration inhibitor, substantially increased lifespan in the model C. elegans.

The present invention includes other genes and gene products that regulate the aging process in C. elegans. One such gene, encodes a GTPase, gene T23H2.5; (SEQ ID NO:6, Accession No. AAC48200.1). Inhibition of GTPase results in a longer lifespan.

Four other genes and gene products that regulate aging in C. elegans are also provided: llw-1, gene Y54G11A.8 (SEQ ID NO:7, Accession No. CAA22452); llw-2, gene F59E12.10 (SEQ ID NO:8, Accession No. AAB54251); and llw-3, gene Y48E1B.1 (SEQ ID NO:9, Accession No. CAB07688). Also included is llw4, gene F45H10.4 (SEQ ID NO:10; Accession No. CAB04386). Inhibition of these genes results in a Long-Lived Worm (llw) phenotype.

Also using the technique of double stranded RNA inhibition, a gene encoding a heat shock factor (HSF) or heat shock protein (HSP) was found to regulate aging in C. elegans. Inhibition of the HSF gene and gene product resulted in worms that display the objective characteristic of aging prematurely (described below) and have short lifespans compared to control worms. HSF is a transcriptional activator of stress related genes. The present invention provide nucleic acids from C. elegans encoding HSF-1, gene Y53C10A.12 (SEQ ID NO:11, Accession No. CAA22146). As described above, for RNAi treatments that decrease lifespan, restoring gene expression should restore a normal lifespan. Furthermore, overexpression of this gene in C. elegans extends lifespan.

It has been discovered that old worms have a number of characteristic features that are highly recognizable and diagnostic when the animals are viewed with Nomarski optics. These characteristics allow for a determination of whether of not a worm is aging prematurely, aging normally, aging slowly, or not aging at all, e.g., has a mutation that causes a sick rather than an aging phenotype. Thus, these objective characteristics can be used as an assay, in combination with RNAi, for genes, gene products, and drugs involved in lifespan regulation. The present invention therefore also provides genes, identified using RNAi, that regulate the aging process in adult eukaryotes.

As described above, the present invention provides a method of using RNAi to identify genes and gene products involved in lifespan regulation, by screening, e.g., for increased or decreased mean and median lifespan. The present invention also demonstrates that Nomarski microscopy provides a powerful way to monitor the aging process in cells and tissues of C. elegans. This technique permits an objective of the quality of cells and tissues that make up most of the body mass. It was found that the tissues of aging animals have a very characteristic appearance, using a number of objective criteria, e.g., yolk accumulation, loss of ability to chew and expel (distended oral and anal cavities), bacterial packing in the intestine (constipation), necrotic cavities in tissue, curdled appearing tissue, and germ cell appearance (graininess, large, well separated nuclei, fewer nuclei, and cavities). These characteristics allow for a determination of whether of not a worm is aging prematurely (progeria), aging normally, aging slowly, or not aging at all, e.g., has a mutation that causes a sick rather than an aging phenotype. Thus, these objective characteristics can be used, as an assay for genes and drugs involved in lifespan regulation. In one embodiment, the characteristics are used to evaluate an organism or cell that is treated with RNAi. In another embodiment, the characteristics are used to evaluate an organism or cell that is genetically mutated. Using the technique of double stranded RNA inhibition, a gene encoding Heat Shock Factor (HSF) was found to prevent premature aging in C. elegans.

In one aspect, the invention features a method that includes: (1) providing a library of nucleic acids, each nucleic acid of the library comprising a segment of a gene of an organism; and (2) for each member of the library, (a) generating double-stranded RNA (dsRNA) from the respective member of the library, (b) providing the dsRNA to a cell or one or more cells of an organism to provide a dsRNA treated cell or a dsRNA treated organism, and (b) monitoring an age-associated parameter of the dsRNA treated cell or the dsRNA treated organism. Exemplary dsRNA-treated organisms include a nematode, C. elegans, an organism other than a nematode, Drosophila, zebrafish, and a mammal, e.g., a mouse. The providing of dsRNA can include feeding the organism the dsRNA or a bacterium that expresses the dsRNA. Exemplary dsRNA-treated cells include a Drosophila cell or a mammalian cell, e.g., a murine, canine, bovine, primate, or human cell. The cell can be culture in vitro. The age-associated parameter can be any age-associated parameter, e.g., a parameter described herein such as lifespan.

The method can be repeated for a cohort of dsRNA treated organisms and the age-associated parameter can include a survival curve for the cohort. The method can further include, for each member of the library indicated as affecting lifespan of the organism, evaluating abundance of an RNA or a protein corresponding to indicated library member or an RNA or protein corresponding to a gene listed in Tables 5 and 6. The abundance can be evaluated, for example, in a defined set of cells or in organisms of defined age. The abundance can be evaluated using an array, e.g., a nucleic acid microarray. The method can include other features described herein.

In another aspect, the invention features a method that includes: evaluating a relationship between presence or abundance for each species of a plurality of RNA or protein species with respect to age of a cell or organism; producing or delivering a double-stranded RNA to a cell or one or more cells of an organism, the RNA corresponding to a species whose presence or abundance is correlated with age; and monitoring an age-associated parameter of the cell or the one or more cells or the organism. Evaluating the relationship can include transcriptional profiling using a nucleic acid array. The plurality of RNA or protein species can include one or more species corresponding to a gene listed in Tables 5 and 6. The plurality can include at least 10, 20, 40, 50, 60, 70% or 100% of the genes listed in Tables 5 and 6. In one embodiment, the organism is an invertebrate. In another embodiment, the organism is a vertebrate, e.g., a mammal. Similarly, a cell can be a cell of a vertebrate (e.g., a mammal, e.g., a human) or an invertebrate, e.g., a nematode.

In another aspect, the invention features a method that includes: contacting a test compound to a living or biochemical system that includes a target protein selected from the group consisting of: a respiratory chain component, a heat shock promoter activator (e.g., an HSF protein or is an artificial chimeric transcription factor), LLW-1, LLW-2, LLW-3, LLW-4, a small GTPase, a protein encoded by a gene listed in Table 5 and 6, and mammalian (e.g., human) homologues thereof; and evaluating a property associated with the target protein. The method can be used, e.g., to evaluating a test compound, e.g., for an effect on lifespan or a lifespan-related process. In one embodiment, the target protein is a *C. elegans* protein, e.g., a protein that includes SEQ ID NO:1, 2, 3, 4, 5, 6, 7, 8, 9, 10, or 11. In another embodiment, the target protein is a mammalian protein.

The living or biochemical system can be a mammalian or non-mammalian system. In one embodiment, the system includes a cell extract, e.g., a lysate or fraction of a cell, e.g., a membrane preparation, a cytoplasmic preparation, or a partially or completely purified preparation. In another embodiment, the system includes isolated mitochondria, e.g., a cell extract or fraction enriched in mitochondria. In still another embodiment, the system includes a living cell, e.g., cultured cells, e.g., primary cell or transformed cells. In yet another embodiment, the system includes a living organism. The organism includes a cell that can express the target protein.

The method can further include contacting the test compound to an organism (e.g., *C. elegans, Drosophila*, or a mammal, e.g., a mouse) and evaluating an age-associated parameter of the organism.

Exemplary properties include a catalytic parameter; structural conformation; post-translational modification; redox state; physical interaction of the target protein with another protein; metabolite formation or consumption; subcellular localization of the target protein; in vivo half-life of the target protein or target protein activity; transcription of a gene encoding the target protein or translation of the target protein.

In one embodiment, the catalytic parameter describes the catalytic properties of an enzyme, other than the target protein. For example, the target protein is a substrate of the enzyme. In one embodiment, the post-translational modification is a modification of the target protein. In another embodiment, the post-translational modification is catalyzed by the target protein. Exemplary post-translational modifications include phosphorylation, ubiquitination, methylation, acetylation/deacetylation, geranylgeranylation, farnesylation, or proteolytic modification. In one embodiment, where the property relates to metabolite production or consumption, the metabolite can be a direct substrate or direct product of a reaction catalyzed or effected by the target protein. In another embodiment, where the property relates to metabolite production or consumption, the metabolite can be an indirect substrate or indirect product of a reaction catalyzed or effected by the target protein.

A culture cell used in the method can include a heterologous nucleic acid that encodes and expresses the target protein. The method can further include assessing whether the test compound directly interacts with the target protein.

In one embodiment, the target protein is operably linked to a reporter protein and the evaluating comprises evaluating the reporter protein.

In one embodiment, the target protein is a cytochrome, and the property is redox state of the cytochrome.

In another aspect, the invention features a method that includes providing a nematode in which activity of a target protein is reduced in the organism by RNA interference; expressing a gene encoding a protein (e.g., candidate protein) that is heterologous to the organism; and evaluating an age associated parameter of the organism. The method can further include, prior to the evaluating, contacting the organism with a test compound. The candidate protein can be, for example, a mammalian protein. The candidate protein can be, for example, a respiratory chain component. The method can include other features described herein.

In another aspect, the invention features a method that includes: providing a cell in which activity of a target protein is reduced in the organism by RNA interference; expressing a gene encoding a protein (e.g., candidate protein) that is heterologous to the organism; and evaluating an age associated parameter of the organism. The method can include other features described herein.

In still another aspect, the invention features a method that includes providing a cell or an organism (e.g., a nematode) in which activity of a target protein is reduced in the cell or one or more cells of the organism by RNA interference; contacting the organism or the cell with a test compound; and evaluating an age associated parameter of the organism.

In another aspect, the invention features a method that includes assessing an age-related parameter of a nematode that (1) expresses a heterologous gene in at least some cells; and (2) is deficient in at least some cells for an endogenous activity provided by a respiratory chain component. In one embodiment, the heterologous gene is from a non-nematode species, e.g., a mammalian species. In a related embodiment, the heterologous gene encodes a variant of a mammalian protein, the variant having between one and ten substitutions, insertions, or deletions. The heterologous gene can encode a domain of at least 30 amino acids from a mammalian protein or a variant thereof, having between one and six substitutions, insertions, or deletions.

In one embodiment, the endogenous activity is provided by a respiratory chain component (e.g., cytochrome $C_1$ (SEQ ID NO:1), NADH oxidoreductase (SEQ ID NO:2), ATP synthase (SEQ ID NO:3), cytochrome C oxidase (SEQ ID NO:4), phosphoglucose isomerase (SEQ ID NO:5)), a GTPase (SEQ ID NO:6), LLW-1 (SEQ ID NO:7), LLW-2 (SEQ ID NO:8), LLW-3 (SEQ ID NO:9); LLW-4(SEQ ID NO:10); HSf-1 (SEQ ID NO:11), or a protein listed in Table 5 or 6.

The method can include contacting the organism with a test compound, e.g., prior to the assessing. The method can include other features described herein.

In another aspect, the invention features a method of characterizing a protein, the method includes: providing a nucleic acid that encodes a protein having a subject amino acid sequence that contains at least one substitution, insertion, or deletion relative to a reference amino acid sequence, wherein the subject amino acid sequence and the reference amino acid sequence are at least 70% identical; expressing the nucleic acid in a culture cell or in an invertebrate cell; and evaluating an age-associated parameter of the cell, or an organism that includes the cell. The reference amino acid sequence can be selected from a sequence described herein, e.g., one of the following sequences cytochrome $C_1$ (SEQ ID NO: 1), NADH oxidoreductase (SEQ ID NO:2), ATP synthase (SEQ ID NO:3), cytochrome C oxidase (SEQ ID NO:4), phosphoglucose isomerase (SEQ ID NO:5), GTPase (SEQ ID NO:6), LLW-1 (SEQ ID NO:7), LLW-2 (SEQ ID NO:8), LLW-3 (SEQ ID NO:9), LLW-4 (SEQ ID NO:10); HSf-1 (SEQ ID NO:11), the amino acid sequences of proteins listed in Table 5 and 6, and human homologues.

In another aspect, the invention features a *C. elegans* nematode that (1) expresses a heterologous gene in at least some cells, the heterologous gene encoding a heterologous protein (e.g., a protein described herein (e.g., a mammalian gene described herein) that is non-identical to a corresponding endogenous protein, or a functional domain thereof; and (2) is deficient in at least some cells for an endogenous activity provided by the corresponding endogenous protein. For example, the nematode can (1) express a heterologous gene in at least some cells, the heterologous gene encoding a respiratory chain component that is non-identical to the corresponding endogenous respiratory chain component, or a functional domain thereof; and (2) be deficient in at least some cells for an endogenous activity provided by the corresponding endogenous respiratory chain component.

In one embodiment, the heterologous gene encodes a mammalian protein. In another embodiment, the heterologous gene encodes a variant of a mammalian protein, the variant having between one and ten substitutions, insertions, or deletions. For example, the heterologous gene encodes at least a domain of at least 30 amino acids from a mammalian protein or a variant thereof, having between one and six substitutions, insertions, or deletions. The deficiency can be mediated by dsRNA, e.g., by RNA interference.

The invention also features a method that includes assessing an age-associated parameter of a nematode described herein, e.g., a nematode described above. In one embodiment, the method further includes, prior to the assessing, contacting the nematode to a test compound.

In another aspect, the invention features a C. elegans nematode that (1) is deficient in at least some cells for an endogenous activity, the deficiency generated by dsRNA in the cells, and (2) has an average lifespan of at least 24, 26, or 28 days (e.g., in the N2 background) or an average lifespan of at least 25% greater than the average lifespan of an otherwise identical nematode not contacted with the dsRNA. The nematode is such that, absent the deficiency, the nematode has an average lifespan of less than 22, 20, 18, or 16 days. In one embodiment, the nematode has functional genes for dauer pathway and/or functional genes for clk-1, gro-1, and/or another gene described herein. For example, the nematode can be wild-type with respect to a laboratory standard, e.g., the N2 background or another background. The dsRNA may include a strand that is complementary to a nucleic acid encoding a protein described herein, e.g., comprising an amino acid sequence selected from the group consisting of: cytochrome $C_1$ (SEQ ID NO:1), NADH oxidoreductase (SEQ ID NO:2), ATP synthase (SEQ ID NO:3), cytochrome C oxidase (SEQ ID NO:4), phosphoglucose isomerase (SEQ ID NO:5), GTPase (SEQ ID NO:6), LLW-1 (SEQ ID NO:7), LLW-2 (SEQ ID NO:8), LLW-3 (SEQ ID NO:9); LLW-4 (SEQ ID NO:10); and HSF-1 (SEQ ID NO:11), proteins listed in Table 5 and 6, and human homologues corresponding to all of the above.

In another aspect, the invention features a method that includes: providing a nematode described herein, e.g., a nematode described above; introducing a heterologous gene that encodes a polypeptide into the nematode; expressing the heterologous gene in the nematode or a progeny of the nematode under conditions wherein the polypeptide is produced; and monitoring an age-associated parameter of the nematode or the progeny of the nematode. The heterologous gene can be, e.g., a nematode gene or a mammalian gene.

In another aspect, the invention features a method includes: providing a library of a test agents; contacting each test agent of the library to cells; evaluating expression of a HSF-regulated gene in the contacted cells; for each test agent that alters the expression of a HSF-regulated gene, contacting a test organism with the test compound; and evaluating an age-associated parameter of the test organism. Many genes regulated by HSF are known or can be readily identified. See, e.g., GuhaThakurta et al. *Genome Res* 12(5):701-12 (2002) and Christians et al. *Crit Care Med* 2002 January; 30(1 Suppl): S43-50 (2002).

In another aspect, the invention features a nucleic acid vector that includes (1) a coding sequence encoding an amino acid sequence comprising SEQ ID NO:7, 8, 9, or 10 or a fragment thereof; and (2) one or more of the following: (a) a promoter that is operably linked and heterologous to the coding sequence, and (b) a second coding sequence encoding a reporter protein or protein tag, the second coding sequence being operably linked and heterologous to the coding sequence. The invention also features a dsRNA (e.g., an isolated dsRNA) that comprises a nucleic acid segment that is complementary to a C. elegans gene that encodes SEQ ID NO:7, 8, 9, or 10, wherein the dsRNA, when administered to a C. elegans or cell thereof, causes an extension of lifespan of at least 20%. In one embodiment, the dsRNA is not complementary to a homologue (e.g., a homologue described herein) of the C. elegans gene that encodes SEQ ID NO:7, 8, 9, or 10. The invention also provides a method that includes providing (e.g., feeding) an adult nematode a dsRNA described herein. The invention also features an antibody that binds to SEQ ID NO:7, 8, 9, or 10. In a related aspect, the invention features a nucleic acid vector that includes (1) a coding sequence encoding an amino acid sequence comprising to a gene listed in Table 5 or 6; and (2) one or more of the following: (a) a promoter that is operably linked and heterologous to the coding sequence, and (b) a second coding sequence encoding a reporter protein or protein tag, the second coding sequence being operably linked and heterologous to the coding sequence.

The invention also features a method that includes: providing a cell, organism, or biochemical system that includes a subject protein described herein (e.g., a protein comprising an amino acid sequence selected from the group consisting of: cytochrome $C_1$ (SEQ ID NO:1), NADH oxidoreductase (SEQ ID NO:2), ATP synthase (SEQ ID NO:3), cytochrome C oxidase (SEQ ID NO:4), phosphoglucose isomerase (SEQ ID NO:5), GTPase (SEQ ID NO:6), LLW-1 (SEQ ID NO:7), LLW-2 (SEQ ID NO:8), LLW-3 (SEQ ID NO:9); LLW-4 (SEQ ID NO:10); and HSF-1 (SEQ ID NO:11), and proteins described in Tables 5 and 6, or human homologues thereof); contacting an antibody that binds to the subject protein or antigen-binding fragment thereof to the cell or the organism; and evaluating an age-associated parameter of the cell, organism, or biochemical system.

Definitions

As is known to those of skill in the art, "oxidative phosphorylation" or "mitochondrial respiratory chain protein" and "glycolysis" proteins are involved in metabolic energy pathways that are universal in eukaryotic biological systems. The terms "oxidative phosphorylation or mitochondrial respiratory chain protein," e.g., cytochrome C1 (SEQ ID NO:1 Accession No. CAA99820.1); NADH oxidoreductase (SEQ ID NO:2 Accession No. AAB522474.1); ATP synthase (SEQ ID NO:3 Accession No. AAB37654.1); and cytochrome C oxidase (SEQ ID NO:4 Accession No. CAB03002.1); or a "glycolysis protein," e.g., phosphoglucose isomerase, hexose isomerase, or glucose phosphate isomerase (SEQ ID NO:5 Accession No. CAB60430.1); or "GTPase" e.g., (SEQ ID NO:6, Accession No. AAC48200.1); or "heat shock factor," e.g. HSf-1 (SEQ ID NO:11, Accession No. CAA22146); or "Long-lived worm protein," e.g. LLW-1 (SEQ ID NO:7, Accession No. CAA22452), LLW-2 (SEQ ID NO:8, Accession No. AAB54251), LLW-3 (SEQ ID NO:9, Accession No. CAB07688), LLW-4 (SEQ ID NO: 10, Accession No. CAB04386), or a nucleic acid encoding a "mitochondrial respiratory chain protein, e.g., cytochrome $C_1$, cytochrome C oxidase, NADH oxidoreductase, and ATP synthase" or a "glycolysis protein, e.g., phosphoglucose isomerase," or a "GTPase" or a "heat shock factor" or a "long-lived worm protein, e.g., llw-1, llw-2, llw-3, llw-4" as well as the genes and gene products listed in Table 5 and Table 6 refer to eukaryotic and mammalian nucleic acids and polypeptide polymorphic variants, alleles, mutants, and interspecies homologs that: (1) have an amino acid sequence that has greater than about 50% amino acid sequence identity, preferably 60%, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by the *C. elegans* genes provided herein; (2) bind to antibodies, e.g., polyclonal antibodies, raised against an immunogen comprising an amino acid sequence of a *C. elegans* mitochondrial respiratory chain, glycolysis protein, GTPase, heat shock factor, or long-lived worm protein, or gene product listed in Table 5 or 6 provided herein, and conservatively modified variants thereof; (3) specifically hybridize under moderately stringent hybridization conditions to an anti-sense strand corresponding to a nucleic acid sequence encoding an *C. elegans* mitochondrial respiratory chain, glycolysis protein, GTPase, heat shock factor, or long-lived worm protein or gene listed in Table 5 or Table 6 as provided herein, and conservatively modified variants thereof; (4) have a nucleic acid sequence that has greater than about 50%, preferably greater than about 60%, 65%, 70%, 75%, 80%, 85%, 90%, preferably 91%, 92%, 93%, 94%, 95%, 96%, 97%, 98% or 99% or higher nucleotide sequence identity, preferably over a region of at least about 25, 50, 100, 200, 500, 1000, or more nucleotides, to a *C. elegans* mitochondrial respiratory chain, glycolysis protein, GTPase, heat shock factor, or long-lived worm protein as provided herein; and/or (5) sequences that genetically complement the *C. elegans* loss of function of a mitochondrial respiratory chain, glycolysis protein, GTPase, heat shock factor, or long-lived worm protein or gene listed in Table 5 or Table 6, as provided herein. A polynucleotide or polypeptide sequence is typically from a eukaryote, e.g., an invertebrate, vertebrate, or plant, preferably a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. The sequence of the *C. elegans* genome can be found in *Science* 282:2012-2018 (1998).

The definition explicitly includes the human or mammalian homologues or counterparts of each *C. elegans* aging associated gene or protein described herein, e.g., cytochrome C1, gene C54G4.8 (SEQ ID NO: 1, Accession No. CAA99820.1), NADH oxidoreductase, gene T10E9.7 (SEQ ID NO:2, Accession No. AAB522474.1), ATP synthase, gene F27C1.7 (SEQ ID NO:3, Accession No. AAB37654.1), cytochrome C oxidase, gene F26E4.9 (SEQ ID NO:4, Accession No. CAB03002.1), GTPase, gene T23H2.5; (SEQ ID NO:6, Accession No. AAC48200.1) llw-1, gene Y54G11A.8 (SEQ ID NO:7, Accession No. CAA22452); llw-2, gene F59E12.10 (SEQ ID NO:8, Accession No. AAB54251); llw-3, gene Y48E1B.1 (SEQ ID NO:9, Accession No. CAB07688); llw-4, gene F45H10.4 (SEQ ID NO:10, Accession No. CAB04386); HSF-1, gene Y53C10A.12 (SEQ ID NO:11, Accession No. CAA22146), and the genes and gene products listed in Tables 5 and 6.

The phrase "functional effects" in the context of assays for testing compounds that modulate activity of aging associated genes and proteins includes the determination of a parameter that is indirectly (e.g., upstream or downstream biochemical or genetic effects) or directly under the influence of aging associated proteins, e.g., a chemical or phenotypic effect, such as the ability to increase or decrease lifespan (see, e.g., Kenyon et al., *Nature* 366:461-464 (1993); Hsin & Kenyon, *Nature* 399:362-366 (1999); Apfeld & Kenyon, *Cell* 95:199-210 (1998); and Lin et al., *Nature Genet.* 28:139-145 (2001)) or, e.g., a physical effect such as ligand, cofactor or substrate binding or inhibition of ligand, cofactor or substrate binding. A functional effect therefore includes ligand, cofactor and substrate binding activity; changes in gene expression and gene expression levels in cells; changes in post transcriptional modification of a protein, e.g., phosphorylation or glycosylation; reporter gene or marker expression; changes in abundance and cellular localization; enzymatic activity; cellular half life; redox state; and structural conformation, etc.; and age-associated parameters, i.e., characteristics of young or old cells or organisms such as stress resistance, lifespan, doubling time, telomere length, physiological characteristics, appearance, disease states, etc. "Functional effects" include in vitro, in vivo, and ex vivo activities. The functional effect can be measured in a host cell, organelle (e.g., isolated mitochondria), host cell membrane, isolated organelle membrane (e.g., isolated mitochondrial membrane), cellular extract, organelle extract (e.g., mitochondrial extract) or host organism.

By "determining the functional effect" is meant assaying for a compound that increases or decreases a parameter that is indirectly or directly under the influence of aging associated proteins or genes, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for the protein; measuring inducible markers or transcriptional activation of the protein; measuring binding activity or binding assays, e.g. binding to antibodies; measuring changes in ligand binding activity; measuring cellular proliferation or lifespan; measuring cell surface marker expression; measurement of changes in protein levels for associated sequences; measurement of RNA stability; phosphorylation or dephosphorylation; signal transduction, e.g., receptor-ligand interactions, second messenger concentrations (e.g., cAMP, IP3, or intracellular $Ca^{2+}$); identification of downstream or reporter gene expression (CAT, luciferase, β-gal, GFP and the like), e.g., via chemiluminescence, fluorescence, colorimetric reactions, antibody binding, inducible markers, and ligand binding assays.

"Ligand" refers to a molecule that is specifically bound by a protein.

"Substrate" refers to a molecule that binds to an enzyme and is part of a specific chemical reaction catalyzed by the enzyme.

"Cofactor" refers to an additional component required for activity of an enzyme. (Leninger, *Principles of Biochemistry* (1984); Stryer, *Biochemistry* (1995)). A cofactor may be inorganic such as Fe, Cu, K, Ni, Mo, Se, Zn, Mn or Mg ions, or an organic molecule also known as a coenzyme. Coenzymes include flavin adenine dinucleotide (FAD), nicotinamide adenine dinucleotide (NAD), nicotinamide adenine dinucleotide phosphate (NADP), heme, coenzyme A, pyrodoxal phosphate, thiamine pyrophosphate, 5'-deoxyadenosylcobalamine, biocytin, tetrahydrofolate, retinal, and 1,25-dihydroxycholecalciferol. A co-factor can also include a protein subunit bound to the co-factor.

"Inhibitors", "activators", and "modulators" of aging associated genes and proteins are used to refer to activating, inhibitory, or modulating molecules identified using in vitro and in vivo assays of aging associated proteins and genes.

Inhibitors are compounds that, e.g., bind to, partially or totally block activity, decrease, prevent, delay activation, inactivate, desensitize, or down regulate the activity or expression of aging associated proteins and genes, e.g., antagonists. "Activators" are compounds that increase, open, activate, facilitate, enhance activation, sensitize, agonize, or up regulate aging associated proteins. Inhibitors, activators, or modulators also include genetically modified versions of aging associated proteins and genes, e.g., versions with altered activity, as well as naturally occurring and synthetic ligands, antagonists, agonists, antibodies, antisense molecules, ribozymes, small chemical molecules and the like. Such assays for inhibitors and activators include, e.g., expressing aging associated proteins in vitro, in cells, or cell membranes, applying putative modulator compounds, and then determining the functional effects on activity, as described above.

Samples or assays comprising aging associated proteins and genes that are treated with a potential activator, inhibitor, or modulator are compared to control samples without the inhibitor, activator, or modulator to examine the extent of inhibition. Control samples (untreated with inhibitors) are assigned a relative protein or gene activity value of 100%. Inhibition of aging associated proteins or genes is achieved when the activity value relative to the control is about 80%, preferably 50%, more preferably 25-0%. Activation of aging associated proteins or genes is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation lymphocyte activation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, e.g., *C.* *elegans*, most preferably a mammal such as a primate e.g., chimpanzee or human; cow; dog; cat; a rodent, e.g., guinea pig, rat, mouse; or a rabbit.

The terms "identical" or percent "identity," in the context of two or more nucleic acids or polypeptide sequences, refer to two or more sequences or subsequences that are the same or have a specified percentage of amino acid residues or nucleotides that are the same (i.e., about 50% identity, preferably 55%, 60%, 65%, 70%, 75%, 80%, 85%, 90%, 91%, 92%, 93%, 94%, 95%, 96%, 97%, 98%, 99%, or higher identity over a specified region (e.g., the *C. elegans* proteins provided herein), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., extracellular domains, transmembrane domains, and cytoplasmic domains. Domains are portions of a polypeptide that form a compact unit of the polypeptide and are typically 15 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.–2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al "Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to aging associated proteins, polymorphic variants, alleles, orthologs, and conservatively modified variants, or splice variants, or portions thereof, can be selected to obtain only those polyclonal antibodies that are specifically immunoreactive with aging associated proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

Assays for Genes and Gene Products That Regulate Aging

Genetic and other models can be used to identify mutants, phenotypes (mediated by mutants and by RNAi), genes, and gene products in the aging process, e.g., RNAi analysis; microarray analysis; chemical mutagenesis; mammalian complementation assays for age-associated proteins; yeast two hybrid assays, immunoprecipitation; alteration in age-associated reporter gene expression or localization (e.g., daf-2 or daf-16); overexpression, underexpression, or knock-out of gene expression, etc. Suitable controls include organisms with altered lifespan, e.g., by mutation or RNAi. These assays can be used with eukaryotic organisms, cells, and organelles such as mitochondria. The genes and gene products associated with a mutation are then identified and used to analyze the aging process at a molecular level. Genes and gene products that regulate the aging process can be identified under normal aging conditions. Patterns of gene expression that correlate with normal or abnormal aging can also be used to identify genes associated with aging. The aging process has likely been conserved throughout evolution. Thus, genes and gene products that regulate the aging process in one species will be useful to identify similar or orthologous genes and gene products in divergent species.

A. Manifestations of the Aging Process

The most obvious disruption of the aging process is a change in lifespan of an individual. Lifespan can either be increased or decreased by a mutation in a gene that participates in the aging process or, as shown here, by another intervention, e.g., RNAi mediated silencing of such a gene. In addition, for all eukaryotic organisms other physical characteristics can be used to distinguish young individuals from older individuals. Thus, at an organismal level, a mutation that affects the aging process will usually affect the lifespan of an individual and may also affect other aging characteristics of that individual. Such manifestations of the aging process are known as "age-associated parameters," e.g., indicia from Nomarski analysis, stress resistance, appearance, physiological changes, disease states, loss of doubling capacity, changes in differentiated phenotype, indirect effects such as fusion protein expression and localization or posttranscriptional modification, etc., are described in more detail below.

Those of skill in the art will recognize that the aging process can also be manifested at an organismal level or at a cellular level. While a list of characteristics of aging is provided below, it is not exhaustive and other characteristics of the aging process may also be analyzed within the scope of the present invention.

Characteristics of aging can be distinguished at the organismal level and may be species specific. For example, characteristics of older human individuals include skin wrinkling, graying of the hair, baldness, cataracts, hypermelanosis, osteoporosis, cerebral cortical atrophy, lymphoid depletion, thymic atrophy, increased incidence of diabetes type II, atherosclerosis, cancer, and heart disease (Nehlin et al., *Annals NY Acad. Sci.*, 980:176-179 (2000)). Other characteristics of mammalian aging include the following: weight loss; lordokyphosis (hunchback spine); absence of vigor; lymphoid atrophy; decreases in bone density, dermal thickness, and subcutaneous adipose tissue; decreased ability to tolerate stresses, such as wound healing, anesthesia, and response to hematopoietic precursor cell ablation; sparse hair; liver pathologies; atrophy of intestinal villi; skin ulceration; amyloid deposits; and joint diseases (Tyner et al., *Nature* 415:45-53 (2002)).

Careful observation reveals characteristics of the aging process in other eukaryotes, including invertebrates. For example, characteristics of aging in the model nematode *C. elegans* as observed by Nomarski analysis include slow movement, flaccidity, yolk accumulation, intestinal autofluorescence (lipofuscin), loss of ability to chew and expel (distended oral and anal cavities), necrotic cavities in tissue, curdled appearing tissue, and germ cell appearance (graininess, large, well separated nuclei, fewer nuclei, and cavities).

Characteristics of aging can also be observed in cultured cells and also in mitochondria. Note that many of these characteristics can also be observed in animals. Normal eukaryotic cells have a defined lifespan when taken from the organism grown in culture. These "primary" tissue culture cells are cells that have neither been immortalized nor acquired a transformed phenotype. The primary cells will divide a defined number of times in culture and then die (reviewed in Campisi, *Exper. Geron.* 36:6-7-618 (2001)). Cellular aging is also characterized by changes other than loss of doubling capability, e.g. changes in apoptotic death and changes in differentiated phenotypes (Id.). In some cases, cellular characteristics of aging can also be observed in immortalized or transformed cell lines. Aging cells also show stress resistance, e.g., free radical generation and $H_2O_2$ resistance. Age-related bio-markers, gene, and protein expression patterns may also be used to determine or measure aging.

Finally, aging can be assessed indirectly, by an aging related functional effects (phenotypic, physical, and chemical effects), e.g., gene expression (e.g., transcript abundance), protein abundance/localization/modification state, chromatin structure, signal transduction, second messenger levels, marker expression, phosphorylation, posttranscriptional modification, reporter gene expression, reporter or fusion protein localization, etc. Such effects can often be monitored when examining upstream or downstream genetic or biochemical pathways of an aging associated gene. Such effects can also be monitored using the aging associated gene.

In one embodiment, a test compound is contacted to one or more cells of an organism or one or more culture cells, and the one or more cells, or the entire organism is evaluated. In particular, a characteristic of aging (e.g., a direct observation or an aging-related functional effect) can be evaluated to determine the test compound has an affect on aging or an aging-related process such as stress resistance or metabolism.

B. Isolation of Genes Associated with Aging

Those of skill in the art will recognize that aging associated nucleic acids and proteins may be conserved in divergent species. Thus, the sequence of a nucleic acid or protein associated with aging in one species can be used to identify aging associated nucleic acids and proteins from other species, as well as genetic and biochemical pathways for the aging associated genes. For example, using methods described in this specification, aging associated genes identified in *C. elegans* can be used to identify aging associated genes or proteins in humans or other higher eukaryotes.

Isolation of Genes and Gene Products Associated with Aging Using Classical Genetic Methods.

Using classical genetic methods (random genomic mutagenesis), aging mutants are be generated by mutagenesis. The mutagenesis protocol will depend on the organism. For example, some eukaryotic organisms can be randomly mutagenized chemically by treatment with compounds like ethane methyl sulfonate (EMS) or can be mutagenized by exposure to UV or gamma irradiation. Preferably, these compounds would be used on organisms such as mammalian cells, yeast, *C. elegans, Drosophila melanogaster*, or zebrafish.

Mutants in the aging process will preferably be characterized by an increase or a decrease in lifespan. Mutants in the aging process will also preferably exhibit a temporal change in expression of an aging characteristic, including those listed above. Those of skill in the art will recognize that mutants can be generated in many ways depending on the organism and phenotypes studied. Typically, the mutagenesis process decreases, increases, or changes gene activity. Examples of such mutants include age-1, daf-2, and daf-16 in *C. elegans*.

Isolation of Genes and Gene Products Associated with Aging Using Gene Inactivation.

In another embodiment, aging mutants are made by inactivation of a gene of interest, using methods other than classical genetic mutagenesis methods. The gene of interest can be inactivated, e.g., using dsRNA inhibition, by using antisense technology, or can be inactivated by homologous recombination. The inactivation can take place in a multicellular organism or in cultured cells. For example, the p66 gene has been removed from mice using homologous recombination, creating a mouse with a longer lifespan than wildtype. Transgenic mice of interest which show lifespan increase include Ames dwarf mutant mice, p66(-/-) knockout mice, alpha MUPA and MGMT transgenic mice (see, e.g., Anisimov, *Mech Aging Dev.* 122:1221-1255 (2001); Lithgow & Andersen, *Bioessays* 22:410-413 (2000)).

dsRNA inhibition can also be used to screen a large number of genes for a phenotype. The method is preferably done in an organism whose genome has been sequenced. DNA fragments corresponding to predicted genes are cloned into a vector between two bacterial promoters in inverted orientation. The library is then transformed into a bacterial strain capable of expressing the DNA fragments. The transformed bacteria or the library DNA alone is then introduced into the experimental organism. If desired, inducible promoters can be used and expression of the inhibitory dsRNA can be induced during a particular time of development or under desired conditions.

A preferred embodiment uses a library whose members each include a DNA fragment from *C. elegans*. Each library member is transformed into *E. coli* and the *E. coli* fed to the worms. The DNA fragments are under the control of T7 promoters. The bacteria express a T7 polymerase that is inducible by IPTG, rendering expression of the inhibitory dsRNA inducible by IPTG.

Isolation of Genes and Gene Products Associated with Aging Using Overexpression.

In another embodiment, aging mutants are made by overexpressing a gene associated with aging, using methods other than classical genetic mutagenesis methods. The gene associated with aging is cloned into a vector under the control of a promoter appropriate for the experimental system. The expression vector is then introduced into the experimental system. The overexpression can take place in either a multicellular organism or in cultured cells.

Isolation of Genes and Gene Products Associated with Aging Using Naturally Occurring Mutants.

Aging mutants can also occur naturally. Those of skill in the art will recognize that such mutants do exist and can be used in the present invention. For example, in humans, several premature aging syndromes have been characterized including Werner syndrome, Hutchinson-Guilford disease, Bloom's syndrome, Cockayne's syndrome, ataxia telangiectasia, and Down's syndrome. Where appropriate, cells from an individual afflicted with an aging syndrome can be studied, rather than the whole organism.

Isolation of Genes and Gene Products Associated with Aging Using Genetic or Biochemical Pathways Known to Regulate Aging.

Genetic analysis can also be used to delineate regulatory pathways and determine functional relationships between genes and gene products. In the case of a complex biological process such as aging, more than one regulatory pathway may regulate the aging process. Those of skill in the art will recognize that genetic analysis of mutants can be used to characterize regulatory pathways and determine relationships between genes. Of course, it also possible to use RNA interference to modulate gene activity in analyzing the regulatory pathways and relationships.

An example of genetic analysis of a regulatory pathway is found in *C. elegans*. The daf-2 gene encodes an insulin/IGF-1 receptor homologue. Mutations that lower the level of daf-2 result in animals that have enhanced lifespans. (For review see Guarente and Kenyon, *Nature* 408:255-262 (2000)). daf-16 encodes a forkhead transcription factor homologue that acts downstream of daf-2 and is required for daf-2 activity. daf-16 mutants have short lifespans. Newly isolated mutations can be analyzed for interaction with the daf2/daf16 pathway. In that way, genes and gene products can be assigned to a regulatory pathway.

In addition, genes that interact with the pathway can be identified by using an appropriate mutant screen. For example, the *C. elegans* protein DAF-16 is a transcriptional activator. A fusion protein between DAF-16 and green fluorescent protein (DAF-16/GFP) can be used to identify the cellular location of the protein. In wild-type animals the protein is localized throughout cells. In long-lived daf-2 mutants, DAF-16 is localized to the nucleus.

Those of skill in the art will recognize that the localization of DAF-16/GFP can be used to identify mutants that perturb the daf2/daf16 pathway. Localization of DAF-16/GFP to the nucleus can be used to screen for drugs that enhance lifespan or mutations that enhance lifespan.

A similar fusion using an end product of the pathway, superoxide dismutase (SOD-3), was constructed. Long lived mutants of the daf-2/daf-16 pathway expressed SOD-3/GFP at a higher level than wild-type worms. Levels of fluorescence from SOD-3/GFP can be followed by microscopy. Those of skill in the art will recognize that expression of SOD-3/GFP can be used to screen for long-lived mutants.

Isolation of Genes and Gene Products Associated with Aging Using Changes in Expression Levels.

Those of skill in the art will recognize that levels of messenger RNA can be measured during the aging process. For aging associated proteins, changes in mRNA levels can be detected either during normal aging process or when comparing an aging mutant to a wild-type individual. Changes in mRNA levels can be measured using techniques known to those of skill in the art, including microarrays, northern blots, and RT PCR.

Aging associated genes can be identified through the use of microarrays where changes in expression of mRNA levels under different conditions or at different times of development can be assayed (see Tables 5 and 6). mRNA levels can also be analyzed in aging mutants to identify genes that are affected by increases or decreases in lifespan.

Microarrays are made by methods known to those of skill in the art, or are purchased. Gene expression profiles for the genes described herein can be generated and used for comparison to identify other age-associated genes. The profile can be generated using a microarray, or by other means. The profiles can be derived from animals, cells, mitochondria, or other suitable sources expressing the genes of interest, e.g., RNAi treated cells or animals. Such profiles can be stored as computer files and analyzed or compared to identify additional genes using algorithms known to those of skill in the art.

Moreover, a gene identified by any method, e.g., transcript or protein profiling, RNAi, or genetic mutation, can then by analyzed by one of the other methods. For example, the activity of a gene whose transcription is correlated with aging can altered using RNAi. Further, chromosomal deficiencies and genetic mutations can be identified in the gene of interest. These exemplary alterations can be used to evaluate the contribution of a gene or gene product to the aging phenotype. The functional relevance of genes so identified can be tested with mutants or RNAi.

Computer Assisted Drug Design and Profiling

Yet another assay for compounds that modulate aging involves computer assisted drug design, in which a computer system is used to generate a three-dimensional structure of an aging associated protein based on the structural information encoded by the amino acid or nucleic acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind, e.g., ligands, substrates, cofactors, etc. These regions are then used to identify ligands that bind to the protein.

The three-dimensional structural model of the protein is generated by entering an aging associated protein amino acid sequences of at least 25, 50, 75 or 100 amino acid residues or corresponding nucleic acid sequences encoding an aging associated protein into the computer system. The amino acid sequence represents the primary sequence or subsequence of each of the proteins, which encodes the structural information of the protein. At least 25, 50, 75, or 100 residues of the amino acid sequence (or a nucleotide sequence encoding at least about 25, 50, 75 or 100 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the aging-associated protein is then generated by the interaction of the amino acid sequence and the computer system, using software known to those of skill in the art. The resulting three-dimensional computer model can then be saved on a computer readable substrate. For example, three-dimensional models of the structures of a number of proteins described here are known and can be used to model homologs and interactions with other chemical compounds. See, e.g., Damberger et al. *Protein Sci.* 1994 October; 3(10): 1806-21. (HSF structure); Harrison et al. *Science.* 1994 Jan. 14; 263(5144):224-7 (HSF structure); Lange et al. *Proc Natl*

*Acad Sci U S A.* 2002 Mar. 5; 99(5):2800-5 (cytochrome bc1 complex); Iwata, et al., *Science.* 1998 Jul. 3; 281(5373):64-71; Gibbons et al., *Nat Struct Biol.* 2000 November; 7(11): 1055-61 (F(1)-ATPase); Faig et al., (2001) *Structure* (Camb). 2001 August; 9(8):659-67 (NAD(P)H:quinone oxidoreductase 1); Ingelman et al. *Biochemistry.* 1999 Jun. 1; 38(22): 7040-9. (NAD(P)H:flavin oxidoreductase).

The amino acid sequence represents a primary structure that encodes the information necessary to form the secondary, tertiary and quaternary structure of the aging associated protein. The software looks at certain parameters encoded by the primary sequence to generate the structural model. These parameters are referred to as "energy terms," or anisotropic terms and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand and substrate binding regions are identified by the computer system. Three-dimensional structures for potential ligands are generated by entering amino acid or nucleotide sequences or chemical formulas of compounds, as described above. The three-dimensional structure of the potential ligand is then compared to that of the aging associated protein to identify ligands that bind to the aging associated protein, orthologs thereof, etc. Binding affinity between the protein and ligands is determined using energy terms to determine which ligands have an enhanced probability of binding to the protein.

Computer systems are also used to screen for mutations, polymorphic variants, alleles and interspecies homologs of the aging associated protein or gene. Such mutations can be associated with disease states. Once the variants are identified, diagnostic assays can be used to identify patients having such mutated genes associated with disease states. Identification of the mutated aging associated protein involves receiving input of a first nucleic acid, e.g., SEQ ID NOS:1-11, and genes disclosed in Tables 5 and 6 and orthologs or conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in aging associated protein, e.g., human genes and mutations associated with disease states. The first and second sequences described above can be saved on a computer readable substrate.

Nucleic acids encoding aging associated proteins can be used with high density oligonucleotide array technology (e.g., GeneChip™) to identify family members and homologs, orthologs, alleles, conservatively modified variants, and polymorphic variants in this invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435448 (1998); Hacia et al., *Nucleic Acids Res.* 26:3865-3866 (1998).

In another aspect, the invention features a computer medium having a plurality of digitally encoded data records. Each data record includes a value representing the level of expression of one or more age-associated gene as described herein in a sample, and a descriptor of the sample. The level of expression can relate to mRNA level and/or protein levels. The record can further include an aging-associated parameter as described herein. The descriptor of the sample can be indicate a subject from which the sample was derived (e.g., a patient, a mutant animal), a treatment (e.g., RNAi treatment), or a location of the sample. In one embodiment, the data record further includes values representing the level of expression of genes and proteins other than an age-associated gene of the invention (e.g., other genes associated with an aging-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining an expression profile of the sample, wherein the profile includes a value representing the level expression of an age-associated gene described herein. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to infer a longevity-associated phenotype in a subject wherein an increase or decrease expression of an age-associated gene described herein is an indication that the subject has or is disposed to having an altered longevity-associated phenotype. The method can be used to monitor a treatment for an aging in a subject. For example, the gene expression profile can be determined for a sample from a subject undergoing treatment. The profile can be compared to a reference profile or to a profile obtained from the subject prior to treatment or prior to onset of the disorder (see, e.g., Golub et al., *Science* 286:531 (1999)).

Isolation of Nucleic Acids Encoding Aging Associated Proteins

This invention can include use of routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

Aging associated protein-encoding nucleic acids, polymorphic variants, orthologs, and alleles can be isolated using the *C. elegans* genes provided herein using, e.g., moderate or low stringent hybridization conditions, by screening libraries, by analyzing a sequence database, and/or by synthetic gene construction. Alternatively, expression libraries can be used to clone aging associated proteins, polymorphic variants, orthologs, and alleles by detecting expressed homologs immunologically with antisera or purified antibodies made against *C. elegans* or mammalian aging associated proteins or portions thereof or by complementation, e.g., of a *C. elegans* phenotype. In a preferred embodiment, human nucleic acid libraries are screened for homologues of *C. elegans* genes or proteins that are associated with aging.

To make a cDNA library, one can choose a source that is rich in the RNA of choice. The mRNA is then made into cDNA using reverse transcriptase, ligated into a recombinant vector, and transfixed into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

An alternative method of isolating aging associated protein-encoding nucleic acid and their orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of aging associated protein-encoding genes directly from mRNA, from cDNA, from genomic libraries or cDNA libraries. Degenerate oligonucleotides can be designed to amplify homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of aging associated protein encoding mRNA in physiological samples, for nucleic acid sequencing, or for other purposes. Genes amplified by the PCR reaction can be purified from agarose gels and cloned into an appropriate vector.

Gene expression of aging associated proteins can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like.

Nucleic acids encoding aging associated proteins can be used with high density oligonucleotide array technology (e.g., GeneChip™) to identify aging associated proteins, orthologs, alleles, conservatively modified variants, and polymorphic variants in this invention. In the case where the homologs being identified are linked to modulation of aging associated proteins, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435448 (1998); Hacia et al., *Nucleic Acids Res.* 26:3865-3866 (1998).

The gene for aging associated proteins are typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding aging associated proteins, one typically subclones aging associated protein encoding nucleic acids into an expression vector that contains a strong promoter to direct transcription, a transcription/translation terminator, and a ribosome binding site for translational initiation. Suitable bacterial promoters are well known in the art and described, e.g., in Sambrook et al., and Ausubel et al, supra. Bacterial expression systems for expressing aging associated proteins are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of aging associated protein encoding nucleic acid in host cells. A typical expression cassette thus contains a promoter operably linked to the nucleic acid sequence encoding aging associated proteins and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/$A^+$, pMTO10/$A^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with mitochondrial respiratory chain protein encoding sequences and glycolysis protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of aging associated proteins, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing aging associated proteins.

After the expression vector is introduced into the cells, the transfected cells are cultured under conditions favoring expression of aging associated proteins, which is recovered from the culture using standard techniques identified below.

Expression vectors with appropriate regulatory sequences can also be used to express a heterologous gene in a nematode. In one example, the expression vector is injected in the gonad of the nematode, and the vector is incorporated, e.g., as an extra-chromosomal array in progeny of the nematode. The vector can further include a second gene (e.g., a marker gene) that indicates the presence of the vector. For example, the heterologous gene can be a mammalian gene, e.g., a mammalian cDNA, or a fragment thereof.

Purification of Aging Associated Proteins

Either naturally occurring or recombinant aging associated proteins can be purified for use in functional assays. Naturally occurring aging associated proteins can be purified, e.g., from human tissue. Recombinant aging associated proteins can be purified from any suitable expression system.

Aging associated proteins may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant aging associated proteins are being purified. For example, proteins having established molecular adhesion properties can be reversible fused to aging associated proteins. With the appropriate ligand, aging associated proteins can be selectively adsorbed to a purification column and then freed from the column in a relatively pure form. The fused protein is then removed by enzymatic activity. Finally, aging associated proteins could be purified using immunoaffinity columns.

A. Purification of Aging Associated Proteins from Recombinant Bacteria.

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of aging associated protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Aging associated proteins are separated from other bacterial proteins by standard separation techniques, e.g., with Ni-NTA agarose resin.

Alternatively, it is possible to purify aging associated proteins from bacteria periplasm. After lysis of the bacteria, when the aging associated proteins are exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Aging Associated Proteins Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the aging associated proteins can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The aging associated proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Immunological Detection of Aging Associated Proteins

In addition to the detection of aging associated genes and gene expression using nucleic acid hybridization technology, one can also use immunoassays to detect aging associated proteins of the invention. Such assays are useful for screening for modulators of aging associated proteins, e.g., for regulation of lifespan, as well as for therapeutic and diagnostic applications. Immunoassays can be used to qualitatively or quantitatively analyze aging associated proteins. A general overview of the applicable technology can be found in Harlow & Lane, *Antibodies: A Laboratory Manual* (1988).

Methods of producing polyclonal and monoclonal antibodies that react specifically with the aging associated proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of aging associated proteins may be used to produce antibodies specifically reactive with an aging associated protein. For example, recombinant protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-specific proteins, using a competitive binding immunoassay. Specific polyclonal antisera and monoclonal antibodies will usually bind with a Kd of at least about 0.1 mM, more usually at least about 1 µM, preferably at least about 0.1 µM or better, and most preferably, 0.01 µM or better. Antibodies specific only for a particular ortholog, such as a human ortholog, can also be made, by subtracting out other cross-reacting orthologs from a species such as a non-human mammal.

Once the specific antibodies against aging associated proteins are available, the protein can be detected by a variety of immunoassay methods. In addition, the antibody can be used therapeutically as aging associated protein modulators, e.g., to enhance and extend lifespan or to prevent premature aging. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra.

It is also possible to use protein arrays to detect an aging associated protein, e.g., to concurrently detect a plurality of aging associated proteins. Exemplary methods for producing protein arrays are provided in De Wildt et al. (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000) *Science* 289:1760-1763; WO 0/98534, WO01/83827, WO02/12893, WO 00/63701, WO 01/40803 and WO 99/51773. In some implementations, polypeptides (including peptides) are spotted onto discrete addresses of the array, e.g., at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

Assays for Modulators of Aging Associated Proteins

A. Assays

Modulation of aging associated proteins and genes can be assessed using a variety of in vitro and in vivo assays, as described herein, and, such assays can be used to test for inhibitors and activators of aging associated proteins. Such modulators of aging associated proteins and genes, which are involved in aging, are useful for enhancing lifespan or treating premature aging. Modulators of aging associated proteins and genes are tested using either recombinant or naturally occurring, preferably *C. elegans*, mouse, rat, guinea pig, monkey, or human aging associated proteins.

An example of a modulator of the mitochondrial respiratory chain is antimycin. Antimycin inhibits the transfer of electrons from complex 2 to complex 3 during mitochondrial respiration. This drug has been found to extend the lifespan of *C. elegans*. Administration of antimycin to adult worms increased lifespan, while administration of antimycin to worms from hatching through adulthood substantially increases lifespan. Mean lifespan of untreated worms was 17 days while animals grown in the presence of 0.1 micromolar antimycin in ethanol had a mean lifespan of 21 days.

Preferably, the aging associated proteins or genes will have a *C. elegans* or a mammalian, e.g., rat, mouse, guinea pig, rabbit; monkey, or human sequence. Alternatively, the aging associated proteins or genes of the assay will be derived from a eukaryote and include an nucleic acid or amino acid subsequence having sequence identity to the *C. elegans* genes and gene products described herein. Generally, the sequence identity will be at least 30%, 35%, 40%, 45% or 50%, preferably at least 55%, 60%, 65%, 70%, 75%, 80%, 85%, or 90%, most preferably at least 95%.

Measurement of modulation of aging phenotype with aging associated proteins or cells expressing aging associated proteins or genes, either recombinant or naturally occurring, can be performed using a variety of assays, in vitro, in vivo, and ex vivo. A suitable physiological change that affects activity can be used to assess the influence of a test compound on the polypeptide or nucleic acid of this invention. When the functional effects are determined using intact cells or animals, one can also measure a variety of effects such as, increases or decreases in lifespan, cellular proliferation, or in the case of signal transduction, hormone release, transcriptional changes to both known and uncharacterized genetic markers (e.g., northern blots), changes in cell metabolism such as cell growth or pH changes, and changes in intracellular second messengers such as cGMP.

In a preferred embodiment, aging associated protein or gene modulators are assayed in vivo by screening in *C. elegans* or in a mammalian model system (cellular or animal) for changes in mean and median lifespan.

Some aging associated proteins have measurable enzymatic activity. Thus, enzymatic assays can be performed to identify compounds that modulate the enzymatic activity. Enzymatic activity can encompass a chemical reaction carried out by a protein, as well as binding of substrates, cofactors, regulatory compounds, or ligands to the protein. It may also be useful to monitor the affect of a test compound on other properties of the aging associated protein, e.g., a structural property (e.g., conformation, oligomerization state, stability, mobility, and the like) or a cellular property (e.g., cellular localization, accessibility, clustering, and the like).

The protein activity and binding capabilities assayed will depend on the aging associated protein. For example, the following proteins with known enzymatic activities have been associated with aging in *C. elegans*: cytochrome $C_1$ (gene C54G4.8, SEQ ID NO:1 Accession No. CAA99820.1), NADH oxidoreductase (gene T10E9.7, SEQ ID NO:2 Accession No. AAB522474.1), ATP synthase (gene F27C1.7, SEQ ID NO:3 Accession No. AAB37654.1), cytochrome C oxidase (gene F26E4.9, SEQ ID NO:4 Accession No. CAB03002.1), phosphoglucose isomerase (gene Y87G2A.8, SEQ ID NO:5 Accession No. CAB60430.1), a GTPase (gene T23H2.5, SEQ ID NO:6 Accession No. AAC48200.1), and HSf-1 (gene Y53C10A.12, SEQ ID NO:11 Accession No. CAA22146), and the genes and gene products listed in Table 5 and Table 6

For activity of cytochrome C and C1, binding to the cofactor heme is important. (Lehninger, *Principles of Biochemistry* (1984); Stryer, *Biochemistry* (1995)). Thus, changes in ability to bind heme may correlate with a mutant phenotype or change during aging. Cytochrome C1 is an electron-transferring protein that contains heme and is found in cytochrome reductase, a membrane-associated proton pump. Cytochrome C is a water soluble protein that transfers electrons from cytochrome reductase to cytochrome oxidase. Changes in electron transport may also be seen during aging or as a result of an aging mutation. It is possible to monitor the redox state of the heme cofactor, for example, by spectroscopy.

NADH oxidoreductase is an oligomeric enzyme complex located in the inner mitochondrial membrane. (Lehninger, *Principles of Biochemistry* (1984); Stryer, *Biochemistry* (1995)). In *C. elegans* inhibition of the 30 Kd subunit resulted in enhanced lifespan. Thus, assays of NADH oxidoreductase activity could be associated with aging. It is possible to monitor the redox state of NADH, for example, by spectroscopy.

Cytochrome C oxidase catalyzes the transfer of electrons from cytochrome C to molecular oxygen. (Lehninger, *Principles of Biochemistry* (1984); Stryer, *Biochemistry* (1995)). Those of skill in the art will recognize that this activity can be assayed spectrophotometrically. In addition to this activity, changes in binding to substrates cytochrome C and oxygen may also be assayed.

ATP synthase catalyzes the synthesis of ATP from ADP and orthophosphate. (Lehninger, *Principles of Biochemistry* (1984); Stryer, *Biochemistry* (1995)). The energy of a proton gradient is used to release the ATP product from its binding site. The ATP synthase protein is a multisubunit enzyme. Inhibition of the *C. elegans* homologue of the delta subunit of ATP synthase resulted in an enhanced lifespan phenotype. Activity of the delta subunit is sensitive to the drug oligomycin. Stryer, page 546.

Phosphoglucose isomerase catalyzes the reversible isomerization of glucose-6-phosphate and fructose-6-phosphate. (Lehninger, *Principles of Biochemistry* (1984); Stryer, *Biochemistry* (1995)). The enzyme is involved in glycolysis in most higher organisms and in gluconeogenesis in mammals. An extracellular role has been reported for the protein as a nerve growth factor and cytokine. (Jeffery et al., *Biochem.* 39:955-964 (2000)).

A GTPase enzyme catalyzes the hydrolysis of GTP to GDP. The reaction can be followed using radioactively labeled GTP an separating the reaction products from the reaction substrates.

HSF, a transcription factor, activates transcription by forming a tri-mer, binding to a specific DNA sequence called a promoter and then recruiting RNA polymerases to begin transcription. Stress response and heat shock response proteins are known as chaperoning. Activation of transcription and binding to a target DNA site can measured in vitro using purified or partially purified components. Activation of transcription can also be measured in vivo using a reporter gene construct with these proteins.

The functional activities described above do not represent all of the enzymatic activities that could be found in aging associated proteins. For example, some aging proteins could act to down regulate transcription of messenger RNA. Still other aging proteins may functional, e.g., as a structural scaffold or adaptor protein, e.g., they may or may not have an enzymatic activity.

Assays to identify compounds with modulating activity can be performed in vitro, e.g., in a test tube, or using isolated membranes, e.g., mitochondrial membranes, or using cellular or mitochondrial extracts. Exemplary assays can include, for example, methods described or referenced in Al-Awqati, *Annu. Rev. Cell Biol.* 2:179-199 (1986); Brand et al., *Biol. Rev. Cambridge Philsophic Soc.* 62:141-193 (1987); Capaldi et al., *FEBS Lett* 138:1-7 (1982); Casey, *Biochim. Biophys. Acta* 768:319-347 (1984); Erecinska et al., *J. Membr. Biol.* 70:1-14 (1982); Fillingame, *Annu. Rev. Biochem.* 49:1079-1113 (1980); Hamamoto, *Proc. Natl. Acad. Sci. USA* 82:2570-2573 (1985); Hatefi, *Annu. Rev. Biochem.* 54:1015-1070 (1985); Klingenberg, *Trends Biochem. Sci.* 4:249-252 (1979); LaNoue et al., *Annu. Rev. Biochem.* 48:871-922 (1979); Mitchell, *Nature* 191:144-148 (1961); Prince, *Trends Biochem. Sci.* 13:159-160 (1988); Slater, *Trends Biochem. Sci.* 8:239-242 (1983); Srere, *Trends Biochem. Sci.* 7:375-378 (1982); Tzagoloff, *Mitochondria*, New York: Plenum (1982); Weiss et al., *Biochem. Soc. Trans.* 15:100-102 (1987).

For example, the aging associated protein or gene is first contacted with a potential modulator and incubated for a suitable amount of time, e.g., from 0.5 to 48 hours. In one embodiment, aging associated protein or gene expression levels are determined in vitro by measuring the level of protein or mRNA. The level of protein or nucleic acid is measured using immunoassays such as western blotting, ELISA and the like with an antibody that selectively binds to the polypeptide or a fragment thereof For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using an aging associated protein promoter operably linked to a reporter gene such as chloramphenicol acetyltransferase, firefly luciferase, bacterial luciferase, β-galactosidase and alkaline phosphatase. Furthermore, the gene or protein of interest can be used as an indirect reporter via attachment to a second reporter such as green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

B. Modulators

The compounds tested as modulators of aging associated proteins and genes can be any small chemical compound, or a biological entity, such as a protein, e.g., an antibody, a sugar, a nucleic acid, e.g., an antisense oligonucleotide or a ribozyme, or a lipid. Alternatively, modulators can be genetically altered versions of an aging associated proteins and genes. Typically, test compounds will be small chemical molecules and peptides, or antibodies, antisense molecules, or ribozymes. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. *J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525, 735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Ma.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing aging associated proteins is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100-about 1500 different compounds. It is possible to assay many plates per day; assay screens for up to about 6,000, 20,000, 50,000, or 100,000 or more different compounds are possible using the integrated systems of the invention.

C. Solid State and Soluble High Throughput Assays

In one embodiment the invention provides soluble assays using aging associated proteins or genes, or a cell or tissue expressing aging associated proteins or genes, either naturally occurring or recombinant. In another embodiment, the invention provides solid phase based in vitro assays in a high throughput format, where the aging associated protein or gene is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

The protein of interest, or a cell or membrane comprising the protein of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.). Similarly, any haptenic or antigenic compound can be used in combination with an appropriate antibody to form a tag/tag binder pair.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids (SEQ ID NO:12). Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Another example of a high-throughput assay does not require immobilizing a target protein. Such examples include homogenous assays such as fluorescence resonance energy transfer and fluorescence polarization. Spectroscopy can also be used in a variety of ways. Assays can also be used to generate structure-activity relationships (SAR). A method of analyzing an aging associated protein can also include assays that may not be traditionally associated with a particular throughput, e.g., certain NMR binding assays (e.g., SAR by NMR), calorimetry, crystallization, and so forth.

Cellular Transfection and Gene Therapy

The present invention provides the nucleic acids of aging associated proteins for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a protein of the present invention, thereby mitigating the effects of absent, partial inactivation, or abnormal expression of the gene of interest, or increasing lifespan in a subject with normal gene expression. For example, as described herein, overexpression of HSf-1 extends adult lifespan. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)).

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the protein of choice, the physician evaluates circulating plasma levels of the vector, vector toxicities, progression of the disease, and the production of anti-vector antibodies. In general, the dose equivalent of a naked nucleic acid from a vector is from about 1 μg to 100 μg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

The following examples are provided by way of illustration only and not by way of limitation. Those of skill in the art will readily recognize a variety of noncritical parameters that could be changed or modified to yield essentially similar results.

Example 1

Objective Characteristics of Aging Identified Using Nomarski Differential Interference Contrast Microscopy A. Introduction In this study, the tissues of wild-type animals were compared to those of long-lived and short-lived insulin/IGF-1 signaling mutants during the course of their lives. We have found that Nomarski differential interference contrast (DIC) microscopy provides an effective, rapid and convenient means of visualizing many features of tissue aging. Using this method, we have found that extensive tissue deterioration takes place during aging, not only in the post-mitotic somatic tissues of the animal, but also in a mitotic lineage, the germline. Our findings indicate that insulin/IGF-1 signaling influences lifespan by changing the rate at which the tissues age, and that this pathway governs the aging not only of the post-mitotic somatic cells, but mitotic lineages as well. Interestingly, the majority of animals we have examined whose adult lifespans were shortened by mutations or certain RNAi treatments did not look prematurely "old" upon observation with Nomarski microscopy. However, animals with lifespan mutations that caused shorter lifespans due to premature aging looked prematurely old (e.g., hsp). Thus, this technique aids in distinguishing mutated animals who die young, and mutated animals with premature aging, even though both classes of animals have shortened adult lifespans.

B. Methods

The following strains were used: N2, daf-16(mu86)I, daf-2(e1370)III, daf-2(mu150)III, daf-2(e1370)III; deg-1(u38) X, ced-3(n1286)IV, DH1033 bIs1[vit-2::gfp; rol-6]; sqt-1 (sc103), daf-2(e1370)III; him-5(e1490) V.

Lifespan Analysis: Wild-type, daf-2 and daf-16 animals raised at 20° C. were shifted to 25° C. at the L4 molt, and transferred to new plates every other day thereafter until progeny production ceased. Animals were judged to be dead when they no longer responded to gentle prodding. Animals that crawled off the plate, became desiccated on the sides of the plate, displayed extruded internal organs or died from internally-hatched progeny were censored. Censored animals were incorporated into the data set until the day of their disqualification, as described previously (Apfeld & Kenyon Nature 402:804-9 (1999). Lifespan analysis of ced-3 mutant animals was conducted at 25° C. using isogenic N2 from the Horvitz lab, kindly provided by Cori Bargmann, as a control. Lifespans of daf-2; deg-1 animals were assayed at 20° C. Statview 5.0.1 (SAS) software was used to construct lifespan curves, and to determine means and percentiles. Ages given refer to days of adulthood.

Lipofuscin: Endogenous gut fluorescence was photographed using a 525 nm bandpass filter. Images were collected without automatic gain control in order to preserve the relative intensity of different animals' fluorescence. 2-, 5- and 10-day old adults were photographed on the same day in order to avoid effects of light source variation on apparent fluorescence intensity.

Visualization of Yolk: The vit-2::GFP fusion strain (see above) was a kind gift of David Hersch and Barth Grant. Animals were allowed to age and were photographed using both Nomarski optics and epifluorescence (525 nm).

Nomarski Analysis: Animals were placed on a 2% agarose pad in M9 buffer with 2 mM sodium azide and covered with a coverslip. Control experiments indicated that sodium azide did not affect the age-related phenotypes we observed. Delicate older animals of all genotypes occasionally ruptured and were lost during this process (approximately 10%). Images were captured using a CCD camera coupled to Universal Imaging Corporation's MetaMorph Imaging System (version 3.6). Image files were contrast-balanced and rotated when necessary using PhotoShop 5.0.

Quantification of Tissue Damage: C. elegans heads were photographed as described above. In a blind experiment, photographs of heads were given a score of 1-5, with 1 representing a youthful, unsullied appearance, and 2 through 4 denoting low, medium and high levels of overall deterioration. A rare score of 5 was assigned to animals so deteriorated as to be nearly unrecognizable.

Photographs of germ cells in the distal gonad also were rated-on a scale of 1-5 based on these criteria. In addition, these photographs were also assigned a cumulative value that represented the presence and extent of several of the correlates of aging, e.g., graininess; large, well-separated nuclei; cavities; and a shriveled appearance. Each correlate of aging was given a separate score, which contributed to the final score. Animals could thus be compared not only by the extent of age-related degeneration, but also by the type of changes they exhibited.

Scores were assigned without knowledge of the age or genotype of the worm in the photograph. Overall scores were re-evaluated at least once, and a naive observer was asked to score a selection of photographs in a double-blind experiment.

Statistical Analysis of Tissue damage: Nonparametric analysis of head scores was conducted, using the Kruskal-Wallis Test to determine if there were significant differences between multiple groups, followed by a pairwise comparison, the Mann-Whitney test. All statistical analysis was conducted using Statview 5.0.1 (SAS) software.

C. Results

Decline of Tissue Integrity in Aging Wild-Type Animals

Nomarski optics are commonly used to observe the development of C. elegans. In young animals, the nuclei and nucleoli of all cells are readily visualized using this method. It is also possible to see the boundaries of certain cells and tissues, such as the muscles, gonad, epidermal seam cells, and certain neurons. We observed that in young adults, the cells and tissues appeared similar to those of late juvenile stages, except that the nuclear boundaries were less distinct. This lack of definition became more pronounced as the animals grew older. For example, by day 10 of adulthood, it was very difficult to see the nuclei of the epidermal cells. Neuronal nuclei, which have a wrinkled, "raisin-like" appearance, remained visible throughout the life of the animal, although they, too, grew less distinct with time. In young animals, the cytoplasm and nucleoplasm of most cells are smooth and uniform. However, as the animals grew older, both began to show signs of deterioration. Necrotic cavities of various sizes appeared, often containing vibrating particles that appeared to display Brownian motion. Tissues often acquired a curdled texture.

In older animals, the pharynx, as well as the anterior and anal regions of the intestine were frequently distended and packed with the bacteria. We wondered whether these animals were failing to chew or expel their food, or whether they might be succumbing to bacterial infection. To test this, we looked for constipation in animals grown on plates seeded with bacteria killed by UV-irradiation. We found that worms grown on killed bacteria also become highly constipated shortly before death. This suggests that very aged animals lose the ability to chew or expel their food.

Older animals also accumulated shiny, mobile patches of a substance that appeared be yolk. In young animals, yolk is transported from its site of synthesis in the intestine into the gonad, where it is incorporated into embryos. It is possible that yolk accumulates in old animals when the production of embryos ceases. We examined animals expressing a GFP-tagged yolk protein, and confirmed that this substance was in fact yolk. We also observed shiny but less-mobile material in the bodies of worms that did not show GFP fluorescence. Finally, we also observed increased intestinal autofluorescence, which is thought to be caused by lysosomal deposits of lipofuscin. Lipofuscin is a pigment that progressively accumulates in aging eukaryotic tissues as a result of the oxidative degradation and autophagocytosis of cellular components. Its ubiquitous occurrence in a variety of organisms makes it a universal marker of aging.

The cellular deterioration that we observed during aging was widespread. We chose to study the head of the worm in more detail, since it is a particularly informative and compact area composed of multiple tissue types. The head contains the pharynx, a neuromuscular pump that ingests and grinds bacteria, as well as nervous tissue, muscle, and surrounding epidermis. Using Nomarski optics, we were able to evaluate the general character of this body region, but, because cellular boundaries are often indistinct, we were not able to resolve individual tissue types with certainty.

To quantify the changes we observed, we analyzed photographs of 84 individual wild-type worm heads and assigned each animal a numerical value that represented the extent of damage and deterioration it exhibited (see Methods). At every age, some animals exhibited more extensive tissue deterioration than others, consistent with the fact that some animals live longer than others. Nevertheless, the average level of tissue deterioration in the overall population increased steadily with age in a statistically-significant manner. Together these findings indicate that the tissues of C. elegans deteriorate in a progressive fashion as the animals grow older. This tissue decline can account for the decreased mobility and the flaccid appearance of old worms that are visualized with a low power-dissecting microscope, and is likely to contribute to the death of the animals.

Tissue Deterioration Occurs in the Germline of Aging Wild-Type Animals

The only cells that are able to divide in C. elegans adults are the germline stem cells. Thus it was particularly interesting to ask whether signs of age-related tissue deterioration were present in this tissue. We found that the germlines of older animals showed dramatic signs of aging. The germline of C. elegans is a multinucleate syncytium; however, in young animals the boundaries of individual nuclei are easy to see. We found that older animals often had fewer nuclei within the gonad, that the boundaries of these nuclei were often ragged. In addition, the surrounding tissue often acquired a granular texture. Occasionally the nuclei were enlarged and appeared to be cellularized, suggesting that they might have entered meiosis. These changes became apparent at approximately the fifth day of adulthood and increased with age. Our findings indicate that integrity of the germline declines during the life of the animal. Germline deterioration was quantified as described above, by assigning photographs of individual animals a value that reflected the condition of the tissue. Two-day, five-day and ten-day-old animals exhibited progressively more extensive degeneration, and these differences were statistically significant ($p=0.0003$).

Mutations in the Insulin/IGF-1 Pathway Change the Rate at Which Both Mitotic and Post-Mitotic Tissues Age To ask how mutations in the insulin/IGF-1 signaling system influence tissue aging, we examined long-lived daf-2 (e1370) and daf-2(mu150) mutants and short-lived daf-16 (mu86) mutants at different ages. The daf-2(e1370) allele has been characterized previously (Dorman et al., *Genetics* 141: 1399-1406 (1995); Gems et al., *Genetics* 150:129-155 (1998); Larsen et al., *Genetics* 139:1567-1583 (1995)). At 25°, this mutant is uncoordinated and produces progeny late in life (up to day 40; data not shown). It appears dark when viewed with a dissecting microscope. We found that these animals were shorter than normal animals (1.0 vs 1.4 mm, $p<0.0001$), and their bodies were thinner (47 μm vs 54 μm, $p=0.002$). In contrast, the mu150 allele, which we isolated in a screen for long-lived mutants, is also long lived but appears much healthier than e1370. Unlike daf-2(e1370) animals, which all become dauers at 25° C., only approximately 30% of daf-2(mu150) animals become dauers at this temperature. In addition, mu150 animals moved normally and did not produce progeny late in life. Their bodies were not dark like e1370 mutants, but resembled wild type, indicating that fat production and longevity can be uncoupled. They were only slightly shorter than normal (1.2 vs 1.4 mm, $p=0.01$), and not thinner (53 μm vs 54 μm, $p=0.45$). Overall, this mutant appears remarkably similar to wild type in terms of its behavior and morphology. We also examined short-lived animals carrying the daf-16 null mutation mu86. We were particularly interested to learn whether the signs of aging that we observed in wild-type animals were present in these mutants, or whether they might age in an entirely new way. In addition, since these mutations change the lifespan of the animal, we wanted to know whether they might change the rate at which the tissues aged.

We found that the quality of tissue deterioration in both daf-2 and daf-16 mutants resembled that of wild type, suggesting that both types of mutants age in a normal way but at a different rate. All of the mutants displayed increased lipofuscin-like intestinal fluorescence at relatively old ages. We found that both the somatic tissues and the germlines of daf-2(mu150) and daf-16 mutants exhibited age-related damage that appeared identical to that seen in wild-type. daf-2 (e1370) mutants also aged in a manner similar to wild type, but they exhibited high levels of autofluorescence throughout life, and had less yolk in the body cavity than wild type, even at advanced ages (perhaps because yolk was still exported into progeny). Also, the frequency of constipation and bacterial packing in the pharynx was markedly reduced in daf-2 (e1370) mutants, although it was present in some infirm individuals.

Although the character of the tissue deterioration we observed in daf-2 mutants was similar to that of wild type, we found that the rate of this deterioration was dramatically slowed. For example, in daf-2(e1370) mutants, the outlines of epidermal nuclei were clearly visible until at least 20 days of adulthood, compared to approximately 5 days in wild type. In addition, it was not until daf-2 animals were approximately 20 days old that we began to see the cavities and "curdled" tissues that were so common in 5-day old wild-type animals.

We quantified the extent of tissue damage by scoring photographs of individual heads and germ cells in the distal gonad. Nonparametric analysis of scores assigned to daf-2 and wild type animals of the same age confirmed our impression that daf-2 animals exhibited far less age-related damage in both tissues. We also examined the tissues of daf-16 mutants, whose lifespans are slightly shorter than normal at 25° C. In general, daf-16 animals did not look dramatically older than age-matched wild type animals. On the second day of adulthood, wild type and daf-16 heads looked marginally older than heads of daf-2 mutants (p=0.04). By the fifth day of adulthood, the difference in head scores between wild type or daf-16 and either daf-2 allele was highly significant (p<0.0001). daf-16 and wild-type heads and germ cells were indistinguishable at early ages; it was only on the tenth day of adulthood that daf-16 mutant animals began to look significantly older than wild type when scores of heads (p=0.01) and germ cells (p=0.02) were compared. daf-16 animals at this age will all be dead within two days, whereas wild type worms have a longer life expectancy.

The cavities we saw in old wild-type animals resembled the necrotic cell death seen in certain neurodegeneration mutants, such as the deg-1 sodium-channel mutants. If daf-2 mutations delay the appearance of necrotic cavities during aging, they might be expected to suppress or ameliorate these degenerations in deg-1 animals. However, we found that daf-2; deg-1 double mutants displayed both an abundance of necrotic cavities at a young age and a long, daf-2-like lifespan. This suggests that daf-2 may not directly suppress necrotic cell death, but instead may act to delay an age-dependent process that causes necrosis.

Apoptosis is Unlikely to Influence Aging in *C. elegans*

In vertebrates, apoptosis, or programmed cell death, occurs throughout life and plays an important role in development and cellular growth control. In *C. elegans,* 131 cells undergo apoptosis, during development. It is reasonable to think that apoptosis, could potentially influence the lifespan of the organism. We looked for apoptotic cells, which have a characteristic refractile appearance (Sulston et al., *Developmental Biology* 56:110-156 (1977)), in the somatic tissues of wild type and mutant animals during aging, and failed to observe them. Apoptotic cell death does occur in early meiotic cells of the germline (Gumienny et al., *Development* 126:1011-1022 (1999)). To test the role of apoptosis in a more definitive way, we examined the lifespans of ced-3 mutants, which lack a caspase that is required for apoptosis in *C. elegans*. In ced-3 mutants, cells that should die instead remain alive and, at least in some cases, differentiate into functional cells. We reasoned that if programmed cell death influences organismal death, mutants defective in apoptosis should have abnormal, possibly extended, lifespans. However, we found that ced-3 mutants had lifespans that were indistinguishable from those of wild type. We conclude that apoptosis does not play a significant role in the regulation of wild-type lifespan.

Example 2

*C. elegans* Mutants That Extend Lifespan

Using libraries representing double stranded RNAs from Chromosome I (Fraser et al., *Nature* 408:325-330 (2000)) and Chromosome II, genes that extend the lifespan of *C. elegans* when inhibited were identified. The gene encoded include mitochondrial respiratory proteins, glycolytic proteins, a GTPase, and three genes of unknown function.

A. Screen for Lifespan Enhancing Genes.

Animals were cultured on bacterial strains expressing double stranded RNA in a bacterial feeding library. (Kamath et al., *Genome Biol.* 2:research0002.1-0002.10 (2000); Fraser et al., *Nature* 408:325-330 (2000)). The library was made as follows. The sequence of the *C. elegans* genome is known and has been used to identify predicted genes. DNA fragments corresponding to predicted genes were cloned into a feeding vector L4440 between two T7 bacterial promoters in inverted orientation. The library was then transformed into a bacterial strain carrying IPTG-inducible expression of T7 polymerase. Expression of the dsRNA was induced by addition of IPTG.

*C. elegans* were cultured on bacterial strains expressing dsRNA corresponding to predicted gene sequences from Chromosomes I or II. Worm lifespan was monitored. A sterile *C. elegans* strain (fem-1, fer-2 double mutant) was used to allow the lifespan of a single generation to be analyzed. To analyze lifespan, after reaching adulthood worms were transferred to new plates at least once every seven days. Worms were scored as dead if they failed to respond to being prodded three times with a wire loop. Lifespan data was entered into the Statview statistical data management program for analysis.

B. Inhibiting Metabolic Pathways Results in Enhanced Lifespan.

In the present invention, several metabolic genes were identified that influence the lifespan of *C. elegans* in an RNAi screen of genes located on chromosome I. All of the genes on chromosome I were expressed as double-stranded RNA in a bacterial feeding library (see, e.g., Fraser et al., *Nature* 408: 325-330 (2000)). *C. elegans* were cultured on each of these bacterial strains, and lifespan was monitored. Inhibition of any of four metabolic genes extended lifespan significantly.

Respiratory Chain Mutants

During a systematic screen of a *C. elegans* Chromosome I RNAi library it was discovered that animals grown on bacteria expressing atp-3 double-stranded RNA lived much longer than normal (Fraser et al., *Nature* 408:325 (2000)). Lifespan analysis was conducted at 25° C. as described previously (Kenyon et al., *Nature* 366:461 (1993)). The pre-fertile period of adulthood was used as t=0 for lifespan analysis. Strains were grown at 20° C. for at least two generations before use in lifespan analysis. Statview 5.0.1 (SAS) software was used for statistical analysis and to determine means and percentiles. In all cases, p values were calculated using the logrank (Mantel-Cox) method.

atp-3 encodes a component of the mitochondrial ATP synthase (Complex V). In addition, we found that RNAi of three genes encoding components of the mitochondrial respiratory chain also extended lifespan. These were nuo-2, which encodes a component of complex I (NADI/ubiquinone oxidoreductase), cyc-1, which encodes a component of complex III (cytochrome C reductase) and cco-1, which encodes a component of complex IV (cytochrome C oxidase). Results are shown in Table 1.

TABLE 1

Statistical analysis of adult lifespans

| Strain/treatment | Mean ± s.e.m. (days) | 75th percentile (days)* | Number of animals that died/total[†] | P |
|---|---|---|---|---|
| N2 animals grown at 25° C. on bacteria containing: | | | | |
| Vector (α) | 15.2 ± 0.4 | 18 | 48/52 | |
| daf-2 dsRNA | 20.1 ± 0.9 | 26 | 55/71 | <0.0001[§] |
| Complex I (nuo-2) dsRNA | 21.6 ± 0.9 | 25 | 51/54 | <0.0001[§] |
| Complex IV (cco-1) dsRNA | 24.5 ± 0.7 | 27 | 67/69 | <0.0001[§] |
| Complex V (atp-3) dsRNA | 22.1 ± 0.9 | 30 | 54/54 | <0.0001[§] |
| Vector (β) | 13.6 ± 0.5 | 17 | 65/69 | |
| Complex III (cyc-1) dsRNA | 25.4 ± 0.9 | 29 | 65/69 | <0.0001[≠] |
| gpi-1 dsRNA | 18.2 ± 0.5 | 22 | 63/67 | <0.0001[≠] |
| Antimycin A Treatments | | | | |
| fer-15(b26); fem-1(hc17) + ethanol | 16.6 ± 0.6 | 20 | 57/61 | |
| fer-15(b26); fem-1(hc17) + 0.1 μM Antimycin A | 20.4 ± 0.7 | 25 | 51/61 | <0.0001[‡] |
| Lifespans of fer-15(b26); fem-1(hc17) animals grown at 25° C. on bacteria containing the following dsRNA for the indicated times: | | | | |
| Vector, larval and adult | 16.6 ± 0.6 | 20 | 57/64 | |
| Complex III (cyc-1) dsRNA, larval and adult | 24.0 ± 1.0 | 29 | 50/68 | <0.0001[Δ] |
| Complex III (cyc-1) dsRNA, adult only | 16.9 ± 0.6 | 20 | 62/63 | 0.6585[Δ] |
| Complex V (atp-3) dsRNA, larval and adult | 25.2 ± 0.8 | 29 | 61/80 | <0.0001[Δ] |
| Complex V (atp-3) dsRNA, adult only | 15.7 ± 0.5 | 18 | 55/64 | 0.1714[Δ] |
| gpi-1 dsRNA, larval and adult | 20.2 ± 0.8 | 25 | 68/71 | <0.0001[Δ] |
| gpi-1 dsRNA, adult only | 16.3 ± 0.7 | 20 | 61/63 | 0.6075[Δ] |
| daf-16(mu86) animals grown at 25° C. on bacteria containing: | | | | |
| Vector (α) | 9.8 ± 0.2 | 11 | 45/47 | |
| daf-2 dsRNA | 9.7 ± 0.2 | 10 | 55/62 | 0.0792[#] |
| Complex I (nuo-2) dsRNA | 13.7 ± 0.3 | 15 | 59/60 | <0.0001[#] |
| Complex IV (cco-1) dsRNA | 14.6 ± 0.4 | 18 | 60/60 | <0.0001[#] |
| Complex V (atp-3) dsRNA | 14.5 ± 0.6 | 18 | 35/37 | <0.0001[#] |
| Vector (β) | 9.2 ± 0.3 | 10 | 60/69 | |
| Complex III (cyc-1) dsRNA | 16.1 ± 0.3 | 17 | 43/53 | <0.0001[∞] |
| gpi-1 dsRNA | 10.8 ± 0.3 | 12 | 57/64 | <0.0001[∞] |
| daf-2(e1370) animals shifted to 25° C. as L4 and grown on bacteria containing: | | | | |
| Vector | 25.1 ± 1.2 | 34 | 55/58 | |
| Complex I (nuo-2) dsRNA | 48.5 ± 1.4 | 54 | 47/60 | <0.0001[¶] |
| Complex III (cyc-1) dsRNA | 41.5 ± 1.8 | 54 | 52/60 | <0.0001[¶] |
| Complex IV (cco-1) dsRNA | 48.3 ± 1.4 | 56 | 50/62 | <0.0001[¶] |
| Complex V (atp-3) dsRNA | 40.8 ± 3.2 | 54 | 46/59 | <0.0001[¶] |
| gpi-1 dsRNA | 34.5 ± 1.0 | 39 | 58/60 | <0.0001[¶] |
| Alteration of the reproductive system of N2 animals grown at 20° C. on bacteria containing: | | | | |
| intact + vector | 22.3 ± 0.5 | 24 | 62/80 | |
| intact + Complex IV (cco-1) dsRNA | 28.9 ± 1.4 | 38 | 63/80 | <0.0001[¥] |
| germline ablation + Complex IV (cco-1) dsRNA | 44.8 ± 1.9 | 53 | 44/46 | <0.0001[¥] |
| whole-gonad ablation + Complex IV (cco-1) dsRNA | 31.7 ± 1.5 | 40 | 41/44 | <0.0001[¥] |
| Alteration of the reproductive system of clk-1(qm30) animals grown at 20° C.: | | | | |
| N2 | 19.8 ± 0.5 | 24 | 132/159 | |
| clk-1(qm30) | 31.0 ± 1.2 | 37 | 67/80 | <0.0001[✓] |
| clk-1(qm30) germline ablation | 37.5 ± 2.4 | 49 | 49/55 | <0.0001[✓] |
| clk-1(qm30) whole-gonad ablation | 19.9 ± 0.8 | 23 | 45/50 | 0.4549[✓] |

*The 75th percentile is the age when the fraction of animals alive reaches 0.25.

TABLE 1-continued

Statistical analysis of adult lifespans

| Strain/treatment | Mean ± s.e.m. (days) | 75th percentile (days)* | Number of animals that died/total† | P |
|---|---|---|---|---|

†The total number of observations equals the number of animals that died plus the number censored. Animals that crawled off the plate, exploded or bagged were censored at the time of the event. This step incorporated those worms into the data set until the censor date, and was necessary to avoid the loss of information;for example, if a 50-day-old animal crawls off the plate, it is important to include that information in the data set, as that animal was long lived. Control and experimental animals were cultured in parallel and plates were changed at the same time. The logrank (Mantel-Cox) test was used to test the hypothesis that the survivalfunctions among groups were equal. P values were calculated for individual experiments, each consisting of control and experimental animals examined at the same time.
§Compared with N2 worms cultured on HT115 bacteria containing an empty plasmid vector at 25° C. Vector (α), daf-2, Complex I, IV and V dsRNA experiments were conducted at the same time.
¢Compared with N2 worms cultured on HT115 bacteria containing an empty plasmid vector at 25° C. Vector (β), Complex III, and gpi-1 dsRNA experiments were conducted at the same time.
‡Compared with control fer-15(b26); fem-1(hc17) double mutants grown on equivalent amount of solvent (ethanol) at 25° C.
ΔCompared with control fer-15(b26); fem-1(hc17) double mutants cultured on bacteria containing an empty plasmid vector at 25° C.
Compared with daf-16(mu86) mutants cultured on bacteria containing an empty plasmid vector at 25 C. Vector (α), daf-2, Complex I, IV and V dsRNA experiments were conducted at the same time.
∞Compared with daf-16(mu86) mutants cultured on bacteria containing an empty plasmid vector at 25° C. Vector (β), Complex III and gpi-1 experiments were conducted at the same time.
¶Compared with daf-2(e1370) mutants cultured on bacteria containing an empty plasmid vector shifted to 25° C. as L4 larvae.
₹Compared to N2 worms with an intact reproductive system cultured on bacteria containing an empty plasmid vector at 20° C.
✓Compared to N2 worms with an intact reproductive system cultured on OP-50 bacteria at 20° C.

The protein ATP3 (Genbank # AAB37654.1) is a member of the ATP synthase delta family and is 43% identical to human ATP50. NUO2 (Genbank # AAB52474.1) protein is 56% identical to human NDUFS3. CYC1 (Genbank # CAA99820.1) is 50% identical to human CYC1. CCO1 (Genbank # CABO3002.1) is 35% identical to human COX5B. GPI-1 (Genbank # CAB60430.1) is 68% identical to human GPI.

We also found that treatment of wild-type animals with the drug antimycin A, which inhibits complex III (Slater, *Trends Biochem Sci.* 8:239 (1983)), increased lifespan as well.

OP-50 bacteria were spread onto NG plates and allowed to grow for two days at room temperature. 50 μl of 0.01 M Antimycin A (Sigma) dissolved in 100% ethanol was dropped onto bacterial lawn and allowed to dry overnight in a fume hood at room temperature. Eggs offer-15(b26); fem-1 (hc17) double mutants, which become sterile adults at 25° C., were added to the dried plates and incubated at 25° C. Animals were transferred to new Antimycin A plates every 4 days. Control worms (ethanol only) were handled in the same manner) (Table 1).

Because RNAi reduces the level of wild-type mRNA, these treatments were all predicted to decrease the rate of electron transport and ATP production. We measured ATP levels as follows. For each time point, 750 fer-15(b26); fem-1(hc17) double mutants were grown at 25° C., to inhibit progeny production. Each time point was repeated in triplicate. The collected worms were washed four times with S-basal buffer, resuspended in cell lysis buffer and quickly frozen in liquid $N_2$. All samples were stored at −80° C. and processed on the same day. A Roche ATP Bioluminescent HSII kit was used to measure ATP concentrations with an OPTOCOMP I luminometer. ATP concentrations were normalized to absolute protein concentrations. A BioRad protein assay kit was used to measure protein concentrations using a Perkin Elmer MBA2000 spectrophotometer.

ATP levels were reduced 60-80% in animals subjected to complex III (cyc-1) or ATP synthase (atp-3) RNAi, and 40-60% in animals treated with complex I (nuo-2) or complex IV (cco-1) RNAi. Thus, these perturbations all decrease the rate of mitochondrial respiration.

In addition to extending lifespan, respiratory-chain RNAi affected growth and behavior. First, the animals were smaller than normal, suggesting that mitochondrial respiration promotes growth. Because the small animals were well proportioned, it seems likely that a metabolite whose level is regulated by mitochondrial respiration acts as a signal to control body size. Small body size itself is unlikely to cause lifespan extension, because mutants defective in daf-4, which encodes a Smad protein (Estevez et al., *Nature* 365:644 (1993)), are small but not long lived (Tissenbaum et al., *Nature* 410:227 (2001)). Respiratory-chain RNAi also decreased the rate of growth to adulthood, as well as the rates of pharyngeal pumping (eating) and defecation (Table 2). In addition, the animals moved much more slowly than normal (Table 2). Mutations in mev-1, gas-1, clk-1 and isp-1 all reduce the rates of development and movement (Ishii et al., *Nature* 394:694 (1998); Hartman et al., *Mech Aging Dev.* 122:1187 (2001); Wong et al., *Genetics* 139:1247 (1995); Feng et al., *Developmental Cell* 1:663 (2001)) but do not affect body size, suggesting that the level of respiratory activity in our RNAi-treated animals may be lower than in these mutants.

TABLE 2

Timing of biological processes in RNAi-treated and clk-1 mutant animals

| dsRNA or Other Treatment | Feeding Rate (pumps/min. ± s.d.)* | Defecation Rate (seconds/ defecation ± s.d.)† | Mobility (swim strokes/ min. ± s.d.)# | Length of post-embryonic development (hours ± s.d.)‡ |
|---|---|---|---|---|
| Vector | 201 ± 9 | 41 ± 3 | 130 ± 6 | 43 ± 2 |
| Complex I(nuo-2) | 159 ± 8 | 80 ± 4 | 90 ± 2 | 69 ± 3 |

TABLE 2-continued

Timing of biological processes in RNAi-treated and clk-1 mutant animals

| dsRNA or Other Treatment | Feeding Rate (pumps/min. ± s.d.)* | Defecation Rate (seconds/ defecation ± s.d.)† | Mobility (swim strokes/ min. ± s.d.)# | Length of post-embryonic development (hours ± s.d.)‡ |
|---|---|---|---|---|
| Complex III(cyc-1) | 161 ± 10 | 81 ± 1 | 75 ± 13 | 88 ± 2 |
| Complex IV(cco-1) | 144 ± 9 | 79 ± 2 | 94 ± 3 | 68 ± 2 |
| Complex V(atp-3) | 124 ± 17 | 87 ± 5 | 90 ± 9 | 96 ± 2 |
| gpi-1 | 198 ± 8 | 43 ± 3 | 127 ± 6 | 43 ± 2 |
| clk-1(qm30) intact | 161 ± 36 | 69 ± 6 | 77 ± 9 | |
| clk1(qm30) germline-ablated | 140 ± 20 | 50 ± 8 | 91 ± 7 | |
| clk-1(qm30) gonad-ablated | 117 ± 22 | 63 ± 9 | 93 ± 5 | |

*Mean ± s.d. The number of pharyngeal pumps observed in a one-day-old adult animal in 1 minute at 20° C. (n ≧ 8).
†Mean ± s.d. The time required to complete one defecation cycle. A minimum of three consecutive defecations was recorded for each trial at 20° C. (n ≧ 5).
Mean ± s.d. The number of swim cycles completed in 1 minute of a one-day-old adult animal at 20° C. (n ≧ 5).
‡Mean ± s.d. Time (hours) to adulthood at 20° C. (n ≧ 25).

Because RNAi can be administered at different times during the life of an animal, we were able to ask whether mitochondrial respiration acts in an ongoing fashion throughout life to influence aging. To do this, we transferred animals onto bacteria expressing respiratory-chain dsRNA at different ages (Dillin et al., Nature, submitted). Surprisingly, we found that if we allowed the animals to grow to adulthood on normal bacteria, and then shifted them as young adults onto bacteria expressing respiratory-chain dsRNA, their lifespans were not extended (Table 1). To determine whether RNAi lowered respiratory-chain activity in these animals, we assayed their ATP levels and found that they were reduced to the same extent as in animals exposed to respiratory-chain dsRNA from hatching. Thus respiratory-chain RNAi does decrease mitochondrial activity in adult animals. Together these findings indicate that the respiratory chain acts during development and not during adulthood to influence lifespan.

We also asked whether initiating RNAi during adulthood decreased behavioral rates. The rate of movement we observed was the same as that of control animals, but the rate of pumping was decreased (Table 3). Interestingly, however, whereas animals treated with RNAi from the time of hatching pumped in a slow but steady fashion, animals treated as young adults exhibited bursts of rapid pumping followed by pauses. Possibly these pauses were caused by transient depletion of ATP.

TABLE 3

Pumping rates of larva and adults treated with respiratory-chain RNAi

| | Feeding Rate (pumps/min ± s.d.)* | | | |
|---|---|---|---|---|
| RNAi Treatment | Day 2 | Day 3 | Day 4 | Day 5 |
| Vector | 118 ± 15 (0/8) | 140 ± 21 (0/8) | 145 ± 24 (0/8) | 131 ± 49 (1/10) |
| Complex III (cyc-1) larval + adult | 97 ± 21 (0/10) | 83 ± 12 (0/10) | 84 ± 12 (0/10) | 75 ± 12 (0/10) |
| Complex III (cyc-1) adult only | 79 ± 62 (5/12) | 112 ± 80 (3/12) | 80 ± 59 (4/12) | 69 ± 45 (4/12) |
| Complex V (atp-3) larval and adult | 98 ± 15 (0/10) | 87 ± 10 (0/10) | 80 ± 9 (0/10) | 75 ± 8 (0/10) |
| Complex V (atp-3) adult only | 88 ± 80 (6/14) | 98 ± 64 (5/14) | 83 ± 59 (4/14) | 89 ± 54 (4/14) |

*Mean ± s.d. The number of pharyngeal pumps observed in an adult animal in 1 minute at 25° C. Number in parentheses is the number of animals that produced less than 50 pumps per minute/total number of animals tested.

Interaction of Respiratory Chain Mutants with the DAF 16 Pathway.

The insulin/IGF-1 signaling pathway affects lifespan (Guarente et al., Nature 408:25 (2000)). Reducing the activity of DAF-2, an insulin/IGF-1 receptor homolog, or downstream signaling components, extends lifespan approximately two-fold. This lifespan extension requires activity of the forkhead-family transcription factor DAF-16.

However, we found that daf-16(mu86) null mutants lived much longer than normal when subjected to respiratory-chain RNAi (Table 1). In addition, we found that the already long lifespans of daf-2(e1370) mutants were nearly doubled again when the animals were cultured on any of the four bacterial strains expressing respiratory chain dsRNA (Table 1). Moreover, unlike reduction of respiratory chain activity, reduction of insulin/IGF-1 signaling is known to cause a significant increase in ATP levels (Braeckman et al., Curr Biol, 9:493 (1999)).

Finally, both daf-2 and daf-16 act exclusively in adults to regulate lifespan (Dillin et al., Nature). Together these findings indicate that respiratory-chain RNAi does not increase lifespan by inhibiting the DAF-2 pathway.

Interaction of Respiratory Chain Mutants with the Reproductive Pathway.

In C. elegans, removing the germline extends lifespan (Hsin et al., Nature 399:362 (1999)). This lifespan extension is not caused by sterility per se, because animals in which the somatic gonad as well as the germline are removed have normal lifespans (Hsin et al., Nature 399:362 (1999); Kenyon et al., Nature 366:461 (1993)).

We found that animals treated with respiratory-chain RNAi were either sterile or had small broods. The longevity of these animals was not likely to be caused by reduced germline activity, however, because the lifespan extension caused by germline ablation is daf-16 dependent (Hsin et al., Nature 399:362 (1999)).

To test whether the reproductive system could influence lifespan in these RNAi-treated animals, we removed either their germlines or the entire reproductive systems. The germlines or the entire reproductive systems of complex IV (cco-1) RNAi-treated animals were removed by killing Z2 and Z3 or Z1 and Z4, respectively. Laser ablations were performed on newly hatched animals using a nitrogen-pumped dye laser, which produces a wavelength of 440 nm. Successful ablation was confirmed by examining the reproductive systems of adult animals with a dissecting microscope. Worms were anaesthetized with 1.0-1.5 M $NaN_3$ during ablation, a treatment that had no effect on lifespan. The germline and whole-gonad of ablation clk-1(qm30) mutants was performed as described above, in two experiments, with similar results.

In addition to the laser ablation experiments described above, the germlines of respiratory-chain RNAi-treated animals were ablated genetically using glp-1(e214ts) mutant worms, which, at 25° C., produce only a few germ cells and live longer than wild type. Mean lifespans of glp-1(e2141ts) mutant worms grown at 25° C. on bacteria expressing the following dsRNA were: Control (empty vector), 15.0±0.7; Complex I (nuo-2) dsRNA, 19.2±0.7 (p<0.0001); Complex III (cyc-1) dsRNA, 19.7±1.0 (p<0.0001); Complex IV (cco-1) dsRNA, 22.9±0.6 (p<0.0001); and Complex V (atp-3) dsRNA, 23.0±0.6 (p<0.0001)). As with wild type, germline ablation further extended lifespan, whereas whole-gonad ablation did not (Table 1). Thus the reproductive system of these animals appeared to influence lifespan in a normal way.

We also examined the role of the reproductive system in clk-1 mutants. As with animals subjected to respiratory-chain RNAi, ablating the germlines of clk-1 mutants caused an increase in lifespan. However, removing the whole gonad of clk-1 (qm30) mutants produced an unexpected result; it completely abolished their lifespan extensions (Table 1). Thus the longevity of these animals is entirely dependent on the presence of the reproductive system. Interestingly, ablation of the gonad did not rescue the slow growth or behavioral phenotypes of clk-1 (qm30) mutants (Table 2). This finding is significant, because it indicates that the longevity of these mutants is not likely to be caused by their slow rates of growth or behavior.

Glycolytic Pathway Mutants

In our Chromosome I RNAi screen, we also found that lowering the activity of a gene that functions in glycolysis, glucose phosphate isomerase (gpi-1), increased lifespan approximately 20% (Table 1). GPI-1 (Genbank # CAB60430.1) is 68% identical to human GPI. The C. elegans genome contains only one glucose phosphate isomerase, implying that these animals have lowered rates of glycolysis. Consistent with this, we found that these animals had reduced levels of ATP.

In vertebrates, PGI is required not only for glycolysis but also for the survival of sensory neurons (Chaput et al., Nature 332:454 (1988); Faik et al., Nature 332:455 (1988)). Sensory neurons are known to influence the lifespan of C. elegans (Apfeld et al., Nature 402:804 (1999)). However, when we used a fluorescent dye (DiI) to visualize many sensory neurons, we failed to detect any abnormalities (data not shown). In addition, whereas the lifespan extension of sensory mutants is largely daf-16 dependent (Apfeld et al., Nature 402:804 (1999)), this was not the case for animals treated with gpi-1 RNAi (Table 1). Together these findings suggest that gpi-1 RNAi does not increase lifespan by affecting sensory neurons.

Like respiratory chain RNAi, gpi-1 RNAi further extended the lifespans of daf-2(e1370) mutants (Table 1). Interestingly, unlike animals treated with respiratory-chain RNAi, these animals appeared healthy and were normal in size. They had wild-type rates of growth to adulthood and rates of behavior (Table 2). In addition, animals treated with gpi-1 RNAi as adults were not long-lived (Table 1), suggesting that, like respiratory-chain activity, gpi-1 may function during development to affect lifespan.

C. Inhibiting a GTPase Results in Enhanced Lifespan.

Using the screen described above, a Rab-like GTPase Was identified from a Chromosome I library. The name of the gene is T23H2.5 and its accession number is AAC482001. Analysis of the mutant demonstrated that inhibition of the gene extended lifespan by 25%. The inhibition of lifespan was independent of the Daf2/16 pathway.

D. Inhibiting llw Genes Results in an Enhanced Lifespan.

An RNAi screen of a chromosome II library identified three novel genes that extend lifespan when inhibited. llw-1, gene Y54G11A.8, contains a TPR-like domain and its accession number is CAA22452 (SEQ ID NO: 7). llw-3, gene Y48E1B.1, contains a proline-rich domain and its accession number is CAB07688 (SEQ ID:9). Inhibition of llw-2, gene F59E12.10, also resulted in enhanced lifespan, and its accession number is AAB54251 (SEQ ID NO:8). Table I shows the result of dsRNA expression corresponding to these genes.

TABLE 4

Inhibition of llw genes enhances C. elegans lifespan

| Gene | dsRNA expressed | % worms dead at day 20 |
|---|---|---|
| | Vector only | 88% |
| llw-1 | Y54G11A.8 | |
| llw-2 | F59E12.10 | 37% |
| llw-3 | Y48E1B.1 | 52% |
| llw-4 | F45H10.4 | 35% |

Example 3

C. elegans Mutants That Shorten Lifespan

Using the Chromosome I library described previously, C. elegans were fed bacteria expressing dsRNA and screened for shortened lifespan. A cursory examination using objective aging criteria allowed immediate discarding of 6 out of 7 short-lived RNAi-treated strains from further consideration as possible progeric animals. Moreover, the one remaining clone had a dramatic phenocopy of normal aging.

The progeric RNAi candidate encoded a homologue of HSF (heat-shock factor), a transcription factor that activates expression of heat-shock genes in response to heat shock and oxidative stress. The HSf-1 gene is Y53C10.12 and the accession number is CAA22146. As heat shock factor genes are highly conserved, this family of genes therefore is shown to be involved in aging, including human homologs of HSF family genes, e.g., HSF-1.

In a second experiment, over-expression of HSf-1 gene in C. elegans caused an increased adult lifespan. The HSf-1 gene has been cloned and constructed into a plasmid that can be used to inject into the worm. The HSf-1 gene was ectopically over-expressed in the worms that carry this plasmid. Compared to wild type worms, these worms have an increased lifespan.

Example 4

Screening for Genes That Affect Aging Using Microarrays

In C. elegans, aging is regulated in one instance by an insulin/IGF-1 pathway. An insulin receptor homolog, DAF-2 activates a PI 3 kinase pathway which in turn appears to inhibit the function of DAF-16, a forkhead-family transcription factor. daf-2 mutants are long lived, whereas daf-16 and daf-16; daf-2 mutants are short lived. Previous experiments have shown that this daf-2 pathway functions non-cell autonomously, meaning that it must regulate the expression of one or more genes that either encode or regulate the production of a downstream signal or hormone. In addition, there must be a cellular pathway that responds to this second hormone, and finally genes that encode proteins directly involved in the aging process.

Figure 6:
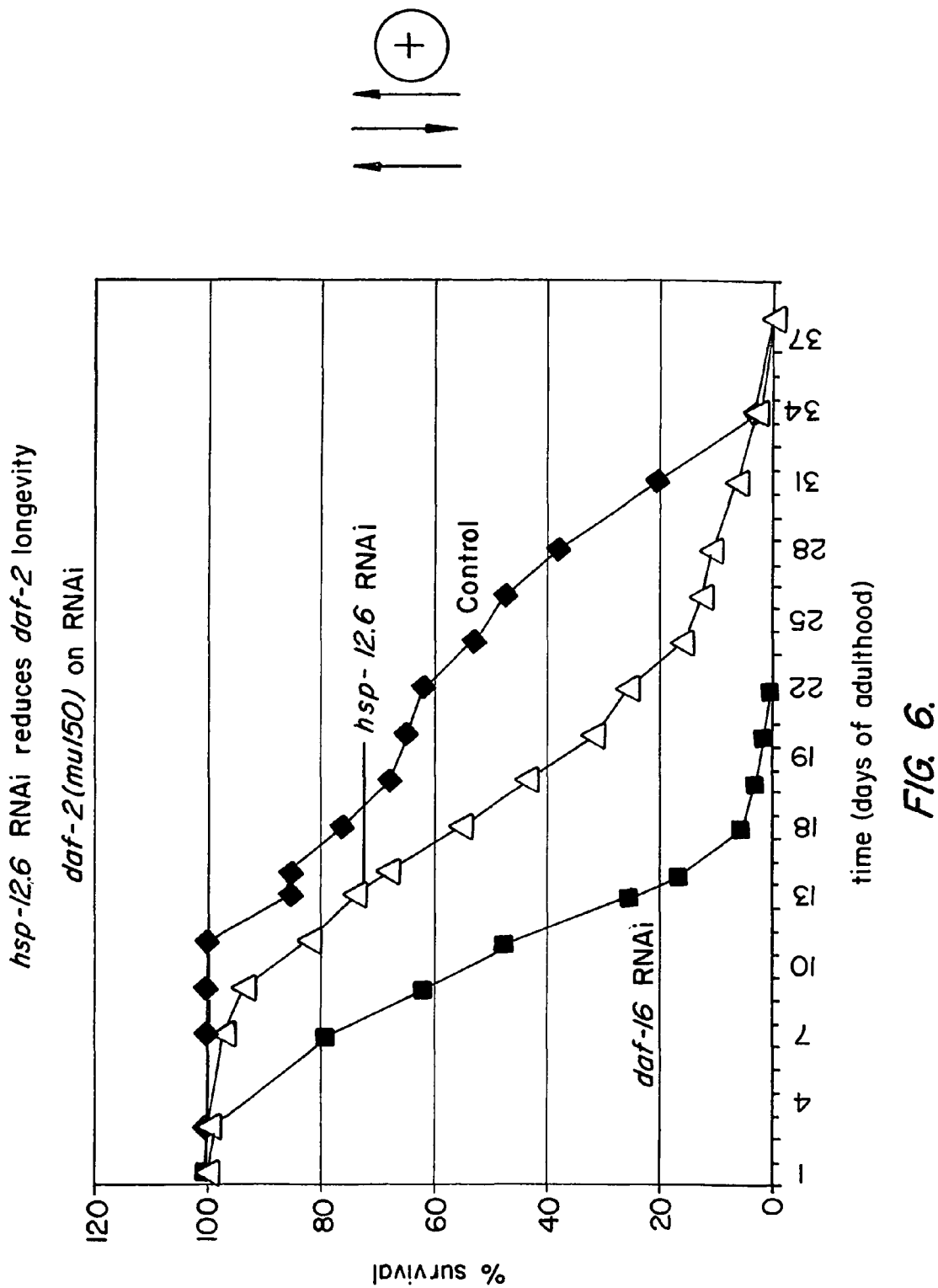
FIG. 6 shows that hsp-12.6 RNAi reduces daf-2 longevity.
Figure 7:
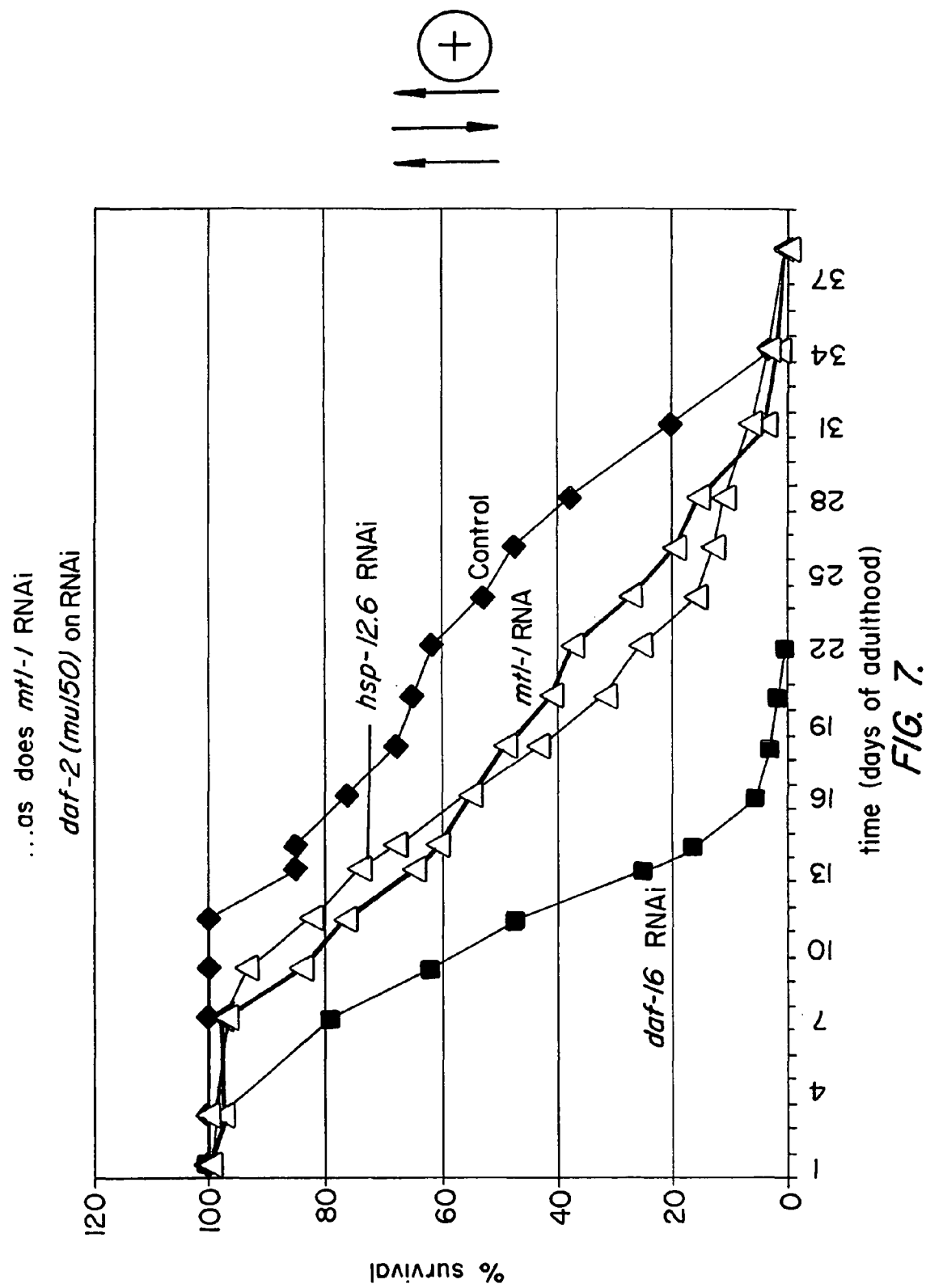
FIG. 7 shows that mtl-1 RNAi reduces daf-2 longevity.
Figure 8:
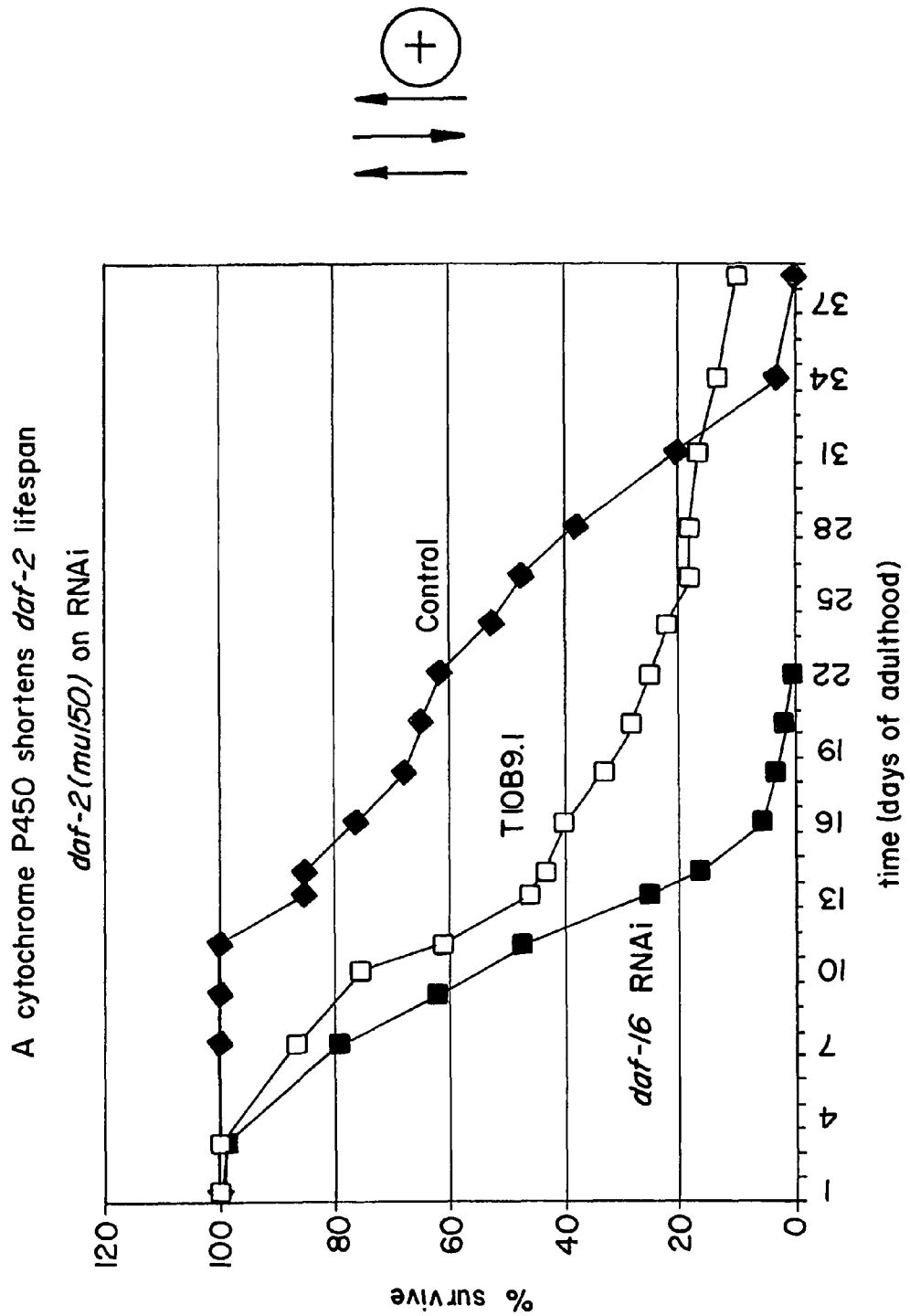
FIG. 8 shows that cytochrome P450 shortens daf-2 lifespan.
Figure 10:
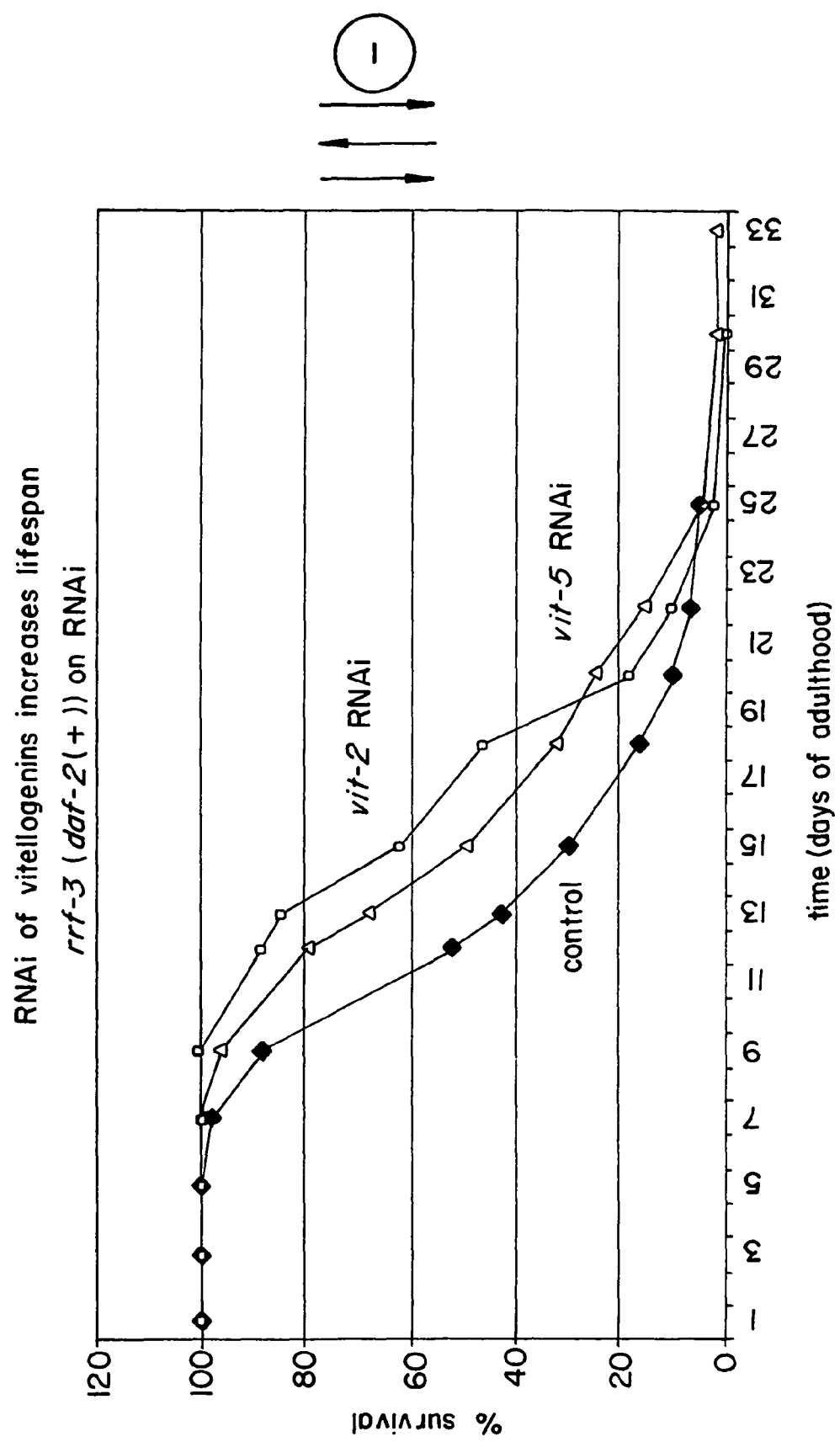
FIG. 10 shows that RNAi of vitellogenins increases lifespan.
Figure 11:
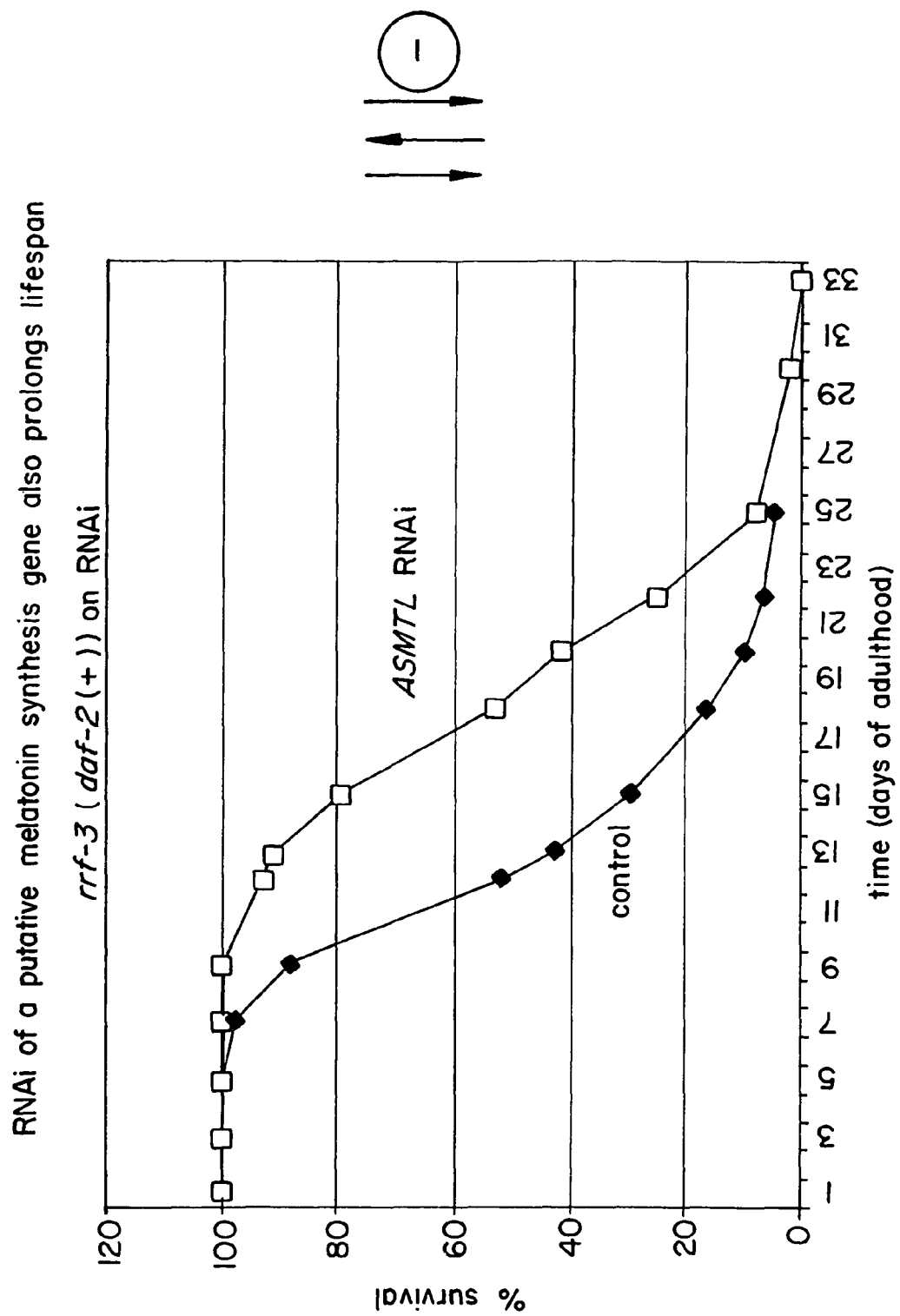
FIG. 11 shows that RNAi of ASMLT (melatonin synthesis gene) prolongs lifespan.
Figure 12:
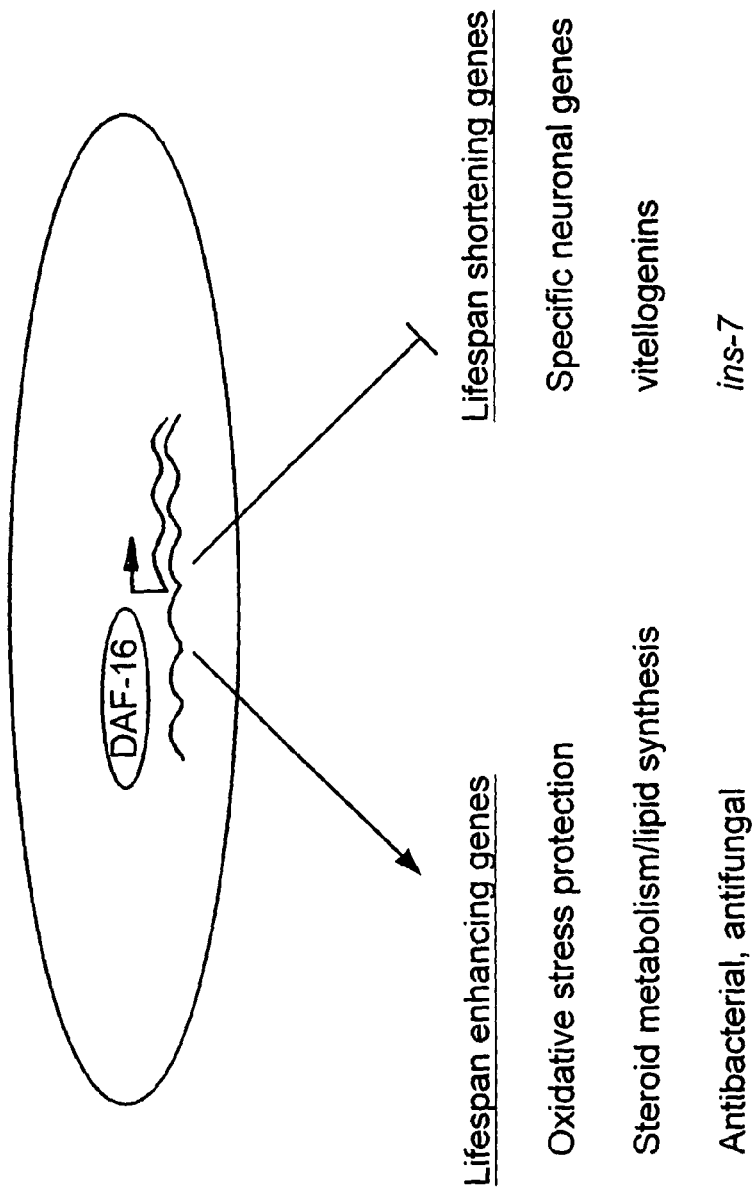
FIG. 12 shows certain genes that modulate lifespan.

Microarrays were constructed using *C. elegans* DNA primers purchased from Research Genetics. The arrays were then used to analyze gene expression profiles in daf-2 and daf-16 mutants. The expression of a number of genes varied in long-lived (daf-2) or short-lived (daf-16 and daf-16; daf-2) *C. elegans* mutants (see Table 5). The activity of genes identified using microarray analysis was then inhibited using RNAi (Table 6). The genes thus identified include hormones that activate the daf-2 pathway, several encoding cytochrome P450 proteins, e.g., genes involved in lipid and steroid biosynthesis, the melatonin synthesis gene (human homolog ASMTL, Accession No. NM_004192), insulin and insulin-like peptides (e.g., ins-7), heat shock factors, catalases, stress-response genes, neuronal genes, oxidative stress protection genes, antibacterial and antifungal genes, vitellogenins, and metabolic genes (see FIGS. 5-12).

Example 5

Screening for Genes and Compounds that Affect Aging Using a DAF-16/GFP Fusion Protein A DAF16-GFP fusion was constructed as described in Lin et al., *Nature Gen.* 28:139-145(2001). DAF16 is a transcription factor and in normal animals is localized throughout cells. Using the DAF16-GFP fusion protein, localization of DAF-16 in long lived animals was studied. In animals with extended lifespans, the DAF-16/GFP fusion was localized to the nuclei.

The following extended lifespan mutants were analyzed: daf-2 mutants and germline ablated animals. DAF-2 is an insulin/IGF-1 receptor homologue. In daf-2 mutants, lifespan is extended in a daf-16 dependent manner. When expressed in daf-2 mutants, the DAF-16/GFP fusion was localized in most nuclei throughout larval development and in adults. In germline ablated animals, the DAF-16/GFP fusion was localized in the nuclei of intestinal cells and to a lesser extent the nuclei of other cell types also.

Localization of DAF-16/GFP is used to screen for drugs or mutations that extend lifespan. Localization of DAF-16/GFP is also used to determine whether a mutation extends lifespan by perturbing the insulin/IGF-1 pathway, germline pathway, or other aging regulatory pathway.

Example 6

Screening for Genes and Compounds That Affect Aging Using an SOD-3/GFP Fusion Protein The *C. elegans* SOD-3 (superoxide dismutase) gene is regulated by the insulin/IGF-1 system. Mutants in the insulin/IGF1 pathway overexpress SOD-3. When an SOD-3/GFP was expressed in long-lived mutants of the insulin/IGF1 pathway, the mutants had a higher level of GFP fluorescence, especially in the intestine, than did wild-type worms expressing the same fusion protein.

Worms expressing the SOD-3/GFP fusion protein are screened for extended lifespan by assaying for intense fluorescence patterns. Screens are done for mutants in the insulin/IGF-1 pathway, for long-lived germline signaling mutants, and for respiratory chain mutants. Screens are also done to identify drugs that affect the aging process.

TABLE 5

| CF512 WL Sept | description | mean | std err | % vector | % avg V |
|---|---|---|---|---|---|
| C04F6.1 | vit-5 | 15.92 | 0.626 | 121.5267 | 103.7134 |
| C17G1.4 | muc-1 | 11.38 | 0.477 | 86.87023 | 74.13681 |
| C17G10.5 | Ent.His. N-acetylmuraminidase | 13.53 | 0.846 | 103.2824 | 88.14332 |
| C18B2.3 | | 12.22 | 0.495 | 93.28244 | 79.60912 |
| C40H5.1 | | 12.68 | 0.736 | 96.79389 | 82.60586 |
| C44E4.2 | | 13.39 | 0.79 | 102.2137 | 87.23127 |
| C54G4.6 | ASMTL | 16.92 | 0.758 | 129.1603 | 110.228 |
| C55B7.4 | AcylCoADH | 13.5 | 0.885 | 103.0534 | 87.94788 |
| Y54G11A.6 | ctl-1 | 16.3 | 0.748 | 124.4275 | 106.1889 |
| Y54G11A.5b | ctl-2 | 13.53 | 0.808 | 103.2824 | 88.14332 |
| Daf-16 | | 13 | 0.519 | 99.23664 | 84.69055 |
| Daf-2 | | 17.1 | 0.834 | 130.5344 | 111.4007 |
| F08B1.1 | vhp-1 phosphatase | 15.5 | 0.644 | 118.3206 | 100.9772 |
| F21F3.3 | farnesyl cystein carboxyl methyltransferase | 12.73 | 0.501 | 97.17557 | 82.9316 |
| F32A5.5 | aquaporin | 14.37 | 0.63 | 109.6947 | 93.61564 |
| F35H12.2 | PTB/PID GAP | 14 | 0.562 | 106.8702 | 91.20521 |
| F48D6.4 | | 14.07 | 1.06 | 107.4046 | 91.66124 |
| F56G4.3 | F-box domain sim.to pes-2 | 14.84 | 0.684 | 113.2824 | 96.67752 |
| F59D8.2 | vit-4 | 12.5 | 0.541 | 95.41985 | 81.43322 |
| H16D19.1 | C-type lectin | 13.22 | 0.778 | 100.916 | 86.12378 |
| H22K11.1 | asp-3 | 15 | 0.708 | 114.5038 | 97.71987 |
| K07A1.7 | | 15.12 | 0.617 | 115.4198 | 98.50163 |
| K10B3.8 | gpd-2 | 14.05 | 0.679 | 107.2519 | 91.53094 |
| K11D2.2 | ASAH acid ceramidase | 14.86 | 1.024 | 113.4351 | 96.80782 |
| R03E9.1 | mdl-1 tf | 15.8 | 0.522 | 120.6107 | 102.9316 |
| T01A4.1 | Npr1-like | 13.19 | 0.734 | 100.687 | 85.92834 |
| T07D10.4 | C-type lectin | 12.96 | 1.03 | 98.9313 | 84.42997 |
| T10B9.1 | Cyt P450 | 10.9 | 0.443 | 83.20611 | 71.00977 |
| T25C12.2 | like T08A9.9 antibacterial | 13.72 | 0.874 | 104.7328 | 89.38111 |
| T25C12.3 | EGF/lectin | 14.34 | 1.02 | 109.4656 | 93.4202 |
| vector | | 13.1 | 0.532 | 100 | 85.34202 |

TABLE 5-continued

| | | | | | |
|---|---|---|---|---|---|
| ZK1320.2 | | 14.63 | 0.459 | 111.6794 | 95.30945 |
| ZK270.2 | FERM domain/band 4.1 | 10.54 | 0.536 | 80.45802 | 68.6645 |
| ZK355.E | | 15.2 | 0.585 | 116.0305 | 99.0228 |

| CF512adult | description | mean | std err | % vector | % avg V |
|---|---|---|---|---|---|
| C04F6.1 | vit-5 | 17.15 | 0.587 | 103.1269 | 111.7263844 |
| C17G1.4 | muc-1 | 18.67 | 0.411 | 112.267 | 121.6286645 |
| C17G10.5 | Ent.His. N-acetylmuraminidase | 15.724 | 0.471 | 94.55201 | 102.4364821 |
| C18B2.3 | | 15.83 | 0.544 | 95.18942 | 103.1270358 |
| C40H5.1 | | 18.2 | 0.542 | 109.4408 | 118.5667752 |
| C44E4.2 | | 19.33 | 0.536 | 116.2357 | 125.9283388 |
| C54G4.6 | ASMTL | 18.41 | 0.803 | 110.7035 | 119.9348534 |
| C55B7.4 | AcylCoADH | 17.27 | 0.676 | 103.8485 | 112.5081433 |
| Y54G11A.6 | ctl-1 | 16.71 | 0.567 | 100.4811 | 108.8599349 |
| Y54G11A.5b | ctl-2 | 16.38 | 0.341 | 98.49669 | 106.7100977 |
| Daf-16 | | 14.53 | 0.49 | 87.37222 | 94.65798046 |
| Daf-2 | | 21.36 | 0.953 | 128.4426 | 139.1530945 |

| CF512adult | description | mean | std err | % vector | % avg V |
|---|---|---|---|---|---|
| F08B1.1 | vhp-1 phosphatase | 13.43 | 0.506 | 80.75767 | 87.49185668 |
| F21F3.3 | farnesyl cystein carboxyl methyltransferase | 15.86 | 0.449 | 95.36981 | 103.3224756 |
| F32A5.5 | aquaporin | 15.43 | 0.468 | 92.78413 | 100.5211726 |
| F35H12.2 | PTB/PID GAP | 18.87 | 0.972 | 113.4696 | 122.9315961 |
| F48D6.4 | | 17 | 0.567 | 102.2249 | 110.7491857 |
| F56G4.3 | F-box domain sim.to pes-2 | 18.58 | 0.791 | 111.7258 | 121.1023453 |
| F59D8.2 | vit-4 | 17.22 | 0.657 | 103.5478 | 112.1824104 |
| H16D19.1 | C-type lectin | 15.34 | 0.541 | 92.24293 | 99.93485342 |
| H22K11.1 | asp-3 | 17.36 | 0.498 | 104.3897 | 113.0944625 |
| K07A1.7 | | 15.68 | 0.559 | 94.28743 | 102.1498371 |
| K10B3.8 | gpd-2 | 17.36 | 0.629 | 104.3897 | 113.0944625 |
| K11D2.2 | ASAH acid ceramidase | 15.77 | 0.607 | 94.82862 | 102.7361564 |
| R03E9.1 | mdl-1 tf | 16.96 | 0.536 | 101.9844 | 110.4885993 |
| T01A4.1 | Npr1-like | 17.25 | 0.48 | 103.7282 | 112.3778502 |
| T07D10.4 | C-type lectin | 14.93 | 0.496 | 89.77751 | 97.26384365 |
| T10B9.1 | Cyt P450 | 15.83 | 0.448 | 95.18942 | 103.1270358 |
| T25C12.3 | like T08A9.9 antibacterial | 17.8 | 0.83 | 107.0355 | 115.9609121 |
| vector | EGF/lectin | 16.63 | 0.468 | 100 | 108.3387622 |
| ZK1320.2 | | 11.72 | 0.435 | 70.47505 | 76.35179153 |
| ZK270.2 | | 18.3 | 0.771 | 110.0421 | 119.218241 |
| ZK355.E | FERM domain/band 4.1 | 15.52 | 0.462 | 93.32532 | 101.1074919 |

| CF512 Dec. | description | mean | std err | % vector | % avg. V |
|---|---|---|---|---|---|
| AC3.7 | UDP-glucuronosyl transferase | 14.78 | 0.365 | 101.2329 | 96.28664 |
| B0213.15 | Cyt P450 | 14.35 | 0.365 | 98.28767 | 93.48534 |
| B0554.1 | | 12.67 | 0.417 | 86.78082 | 82.54072 |
| B0554.6 | like AK6.11 | 12.43 | 0.4 | 85.13699 | 80.9772 |
| C04F6.1 | vit-5 | 12.52 | 0.372 | 85.75342 | 81.56352 |
| C17G1.4 | muc-1 | 12.21 | 0.41 | 83.63014 | 79.54397 |
| C17H12.8 | | 15.16 | 0.325 | 103.8356 | 98.76221 |
| C24B9.4 | DUF32 domain | 14.12 | 0.376 | 96.71233 | 91.98697 |
| C32F10.9 | | 13.59 | 0.381 | 93.08219 | 88.5342 |
| C32H11.10 | DUF141 | 12.92 | 0.493 | 88.49315 | 84.16938 |
| C32H11.12 | DUF141 | 12.1 | 0.38 | 82.87671 | 78.82736 |
| C46F4.2 | long-chain fatty acid-Coenzyme A ligase 4 | 13.33 | 0.386 | 91.30137 | 86.84039 |
| C54D10.1 | GST | 13.56 | 0.371 | 92.87671 | 88.33876 |
| C54G4.6 | ASMTL/Maf-like | 12.81 | 0.422 | 87.73973 | 83.45277 |
| C55B7.4 | Acyl-CoA DH | 13.04 | 0.431 | 89.31507 | 84.95114 |
| Daf-16 | | 8.34 | 0.288 | 57.12329 | 54.33225 |
| Daf-2 | | 16.017 | 0.235 | 109.7055 | 104.3453 |
| F10D2.9 | fat-7 | 14.71 | 0.33 | 100.7534 | 95.83062 |
| F11A5.12 | short-chain DH-reductase; hydroxysteroid 17-beta DH | 13.93 | 0.407 | 95.41096 | 90.74919 |
| F28D1.3 | thaumatin | 12.28 | 0.442 | 84.10959 | 80 |
| F28D1.5 | thaumatin | 12.29 | 0.463 | 84.17808 | 80.06515 |
| F38E11.2 | hsp-12.6 | 14.79 | 0.383 | 101.3014 | 96.35179 |
| F49A5.6 | thaumatin | 14.43 | 0.341 | 98.83562 | 94.00651 |
| F55G11.5 | | 12.1 | 0.356 | 82.87671 | 78.82736 |
| K04E7.2 | pep-2 | 10.6 | 0.315 | 72.60274 | 69.05537 |
| K06A11.1 | | 15.16 | 0.374 | 103.8356 | 98.76221 |
| K07C6.4 | Cyt P450 | 12.13 | 0.411 | 83.08219 | 79.0228 |
| K10D11.1 | | 14.29 | 0.337 | 97.87671 | 93.09446 |
| K11G9.6 | mtl-1 | 13.16 | 0.429 | 90.13699 | 85.7329 |

TABLE 5-continued

| | | | | | |
|---|---|---|---|---|---|
| K12G11.3 | Alcohol DH | 12.58 | 0.396 | 86.16438 | 81.9544 |
| T10B9.1 | Cyt P450 | 10.77 | 0.309 | 73.76712 | 70.16287 |
| T13F2.1 | fat-4 | 13.12 | 0.369 | 89.86301 | 85.47231 |
| T16G12.1 | aminopeptidase | 14.25 | 0.367 | 97.60274 | 92.83388 |
| T20G5.7 | | 15.7 | 0.314 | 107.5342 | 102.2801 |
| T22G5.2 | lbp-7 | 14.116 | 0.349 | 96.68493 | 91.96091 |
| Vector | | 14.6 | 0.372 | 100 | 95.11401 |
| W06D12.3 | fat-5 | 13.69 | 0.429 | 93.76712 | 89.18567 |
| W08D2.4 | fat-3 | 12.13 | 0.241 | 83.08219 | 79.0228 |
| Y38H6C.5 | Zn knuckle domain | 13.25 | 0.37 | 90.75342 | 86.31922 |
| Y49E10.8 | | 15.85 | 0.291 | 108.5616 | 103.2573 |
| ZK1251.2 | ins-7 | 16.4 | 0.19 | 112.3288 | 106.8404 |
| ZK384.4 | | 12.6 | 0.401 | 86.30137 | 82.08469 |

| CF596 | description | mean | std err | % vector | CF596 | % vector |
|---|---|---|---|---|---|---|
| B0213.15 | Cyt P450 | 26 | 0.5 | 111.9242 | B0213.15 | 111.9242 |
| C02A12.4 | N-acetylmuraminidase | 18.63 | 0.855 | 80.19802 | vector | 100 |
| C05E4.4 | | 18.933 | 0.913 | 81.50237 | K12G11.3 | 91.08911 |
| C24B9.4 | DUF23 | 18.59 | 0.816 | 80.02583 | F10D2.9 | 82.5226 |
| Daf-16 | | 11.47 | 0.423 | 49.37581 | C05E4.4 | 81.50237 |
| Daf-2 | | 13.88 | 0.659 | 59.75032 | C02A12.4 | 80.19802 |
| F10D2.9 | fat-7 | 19.17 | 0.885 | 82.5226 | T20G5.7 | 80.19802 |
| F28D1.3 | thaumatin | 18.4 | 0.927 | 79.20792 | C24B9.4 | 80.02583 |
| F38E11.2 | hsp-12.6 | 18.42 | 0.78 | 79.29402 | K11G9.6 | 79.85364 |
| K11G9.6 | mtl-1 | 18.55 | 1.02 | 79.85364 | F38E11.2 | 79.29402 |
| K12G11.3 | Alcohol DH | 21.16 | 1.05 | 91.08911 | F28D1.3 | 79.20792 |
| T10B9.1 | Cyt P450 | 15.36 | 0.813 | 66.12139 | T10B9.1 | 66.12139 |
| T20G5.7 | | 18.63 | 0.938 | 80.19802 | Daf-2 | 59.75032 |
| vector | | 23.23 | 1.02 | 100 | Daf-16 | 49.37581 |

| rrf-3 20C | description | mean | std err | % vector | RNAi | % vector |
|---|---|---|---|---|---|---|
| C04F6.1 | vit-5 | 17.47 | 0.763 | 116.4667 | daf-2 | 207.3333 |
| C32H11.12 | DUF141 | 19.7 | 0.676 | 131.3333 | ZK1251.2 | 155.2 |
| C42D8.2 | vit-2 | 18.15 | 0.576 | 121 | C54G4.6 | 132.38 |
| C54G4.6 | ASMTL | 19.857 | 0.658 | 132.38 | C32H11.12 | 131.3333 |
| daf-16 | | 14.84 | 0.476 | 98.93333 | ZK896.8 | 125.4667 |
| daf-2 | | 31.1 | 0.749 | 207.3333 | C42D8.2 | 121 |
| vector | | 15.02 | 0.613 | 100.1333 | C04F6.1 | 116.4667 |
| ZK1251.2 | ins-7 | 23.28 | 0.512 | 155.2 | vector | 100.1333 |
| ZK896.8 | gcy-18 | 18.82 | 0.731 | 125.4667 | daf-16 | 98.93333 |

| CF512 25 | description | mean | std err | % vector | % avg. V |
|---|---|---|---|---|---|
| C04F6.1 | vit-5 | 14.7 | 0.586 | 86.47059 | 95.76547 |
| C32H11.12 | | 16.5 | 0.635 | 97.05882 | 107.4919 |
| C42D8.2 | vit-2 | 15.42 | 0.58 | 90.70588 | 100.456 |
| C54G4.6 | ASMTL | 18.71 | 0.637 | 110.0588 | 121.8893 |
| daf-16 | | 11.2 | 0.279 | 65.88235 | 72.96417 |
| daf-2 | | 18.13 | 0.76 | 106.6471 | 118.1107 |
| vector | | 17.06 | 0.574 | 100.3529 | 111.1401 |
| ZK1251.2 | ins-7 | 17.05 | 0.606 | 100.2941 | 111.0749 |
| ZK896.8 | gcy-18 | 16.41 | 0.695 | 96.52941 | 106.9055 |

| | | | | | |
|---|---|---|---|---|---|
| | vector | | 16.63 | | 0.468 |
| | vector | | 17.06 | | 0.574 |
| | Vector | | 14.6 | | 0.372 |
| | vector | | 13.1 | | 0.532 |
| | | | 15.3475 | | |

TABLE 6

| Gene | Gene product/homology |
|---|---|
| Upregulated in daf-2 mutants and with daf-2 RNAi, downregulated with daf-16 RNAi | |
| C15H9.1 | C15H9.1: Protein of unknown function |
| C53B7.3 | C53B7.3: Protein with weak similarity to EGF-like repeats, has moderate similarity to *C. elegans* F46C8.4 |
| C34C6.7 | C34C6.7: Protein of unknown function |
| E04F6.9 | E04F6.9: Protein of unknown function, has moderate similarity to *C. elegans* E04F6.8 |
| C50F7.5 | C50F7.5: Protein of unknown function, has moderate similarity to *H. sapiens* MUC1 gene product, a transmembrane mucin |
| Y15E3B.f | Y15E3B.fY15E3B.f |

TABLE 6-continued

| Gene | Gene product/homology |
|---|---|
| F09F7.7 | F09F7.7: Protein of unknown function |
| T23G7.3 | T23G7.3: Protein of unknown function, has weak similarity to *S. cerevisiae* Ygr280p |
| F08B12.4 | F08B12.4: Protein of unknown function |
| F47H4.10 | F47H4.10: Member of an uncharacterized protein family |
| H14N18.1 | H14N18.1: unc-23: Highly similar to mammalian BAG-2, BCL2-associated athanogene 2, a chaperone regulator |
| C40H1.5 | C40H1.5: Member of an uncharacterized protein family |
| T23B3.2 | T23B3.2: Protein of unknown function, has weak similarity to *C. elegans* F47B7.1 |
| C25E10.8 | C25E10.8: Member of an uncharacterized protein family |
| Y105C5A.12 | Y105C5A.12: Protein of unknown function |
| B0507.8 | B0507.8: Protein of unknown function, has similarity to *C. elegans* B0507.7 |
| C25E10.9 | C25E10.9: Member of an uncharacterized protein family |
| F38E11.1 | F38E11.1: Member of the small heat shock protein family |
| Y51A2D.11 | Y51A2D.11: Member of an uncharacterized protein family |
| Y51A2B.1 | Y51A2B.1: Protein of unknown function, has moderate similarity to *C. elegans* C07G3.2 |
| C08E8.4 | C08E8.4: Protein of unknown function, has weak similarity to *C. elegans* C07G3.2 |
| C44H9.5 | C44H9.5: Protein of unknown function |
| K10E9.1 | K10E9.1: Protein of unknown function |
| C08F11.3 | C08F11.3: Protein of unknown function, has moderate similarity to *C. elegans* F56G4.1 |
| C01H6.6 | C01H6.6: Protein of unknown function, has weak similarity to *S. cerevisiae* Yo1060p |
| C24A11.8a | C24A11.2 C24A11.2 |
| W06D12.3 | W06D12.3: fat-5: Likely a palmitoyl-CoA delta-9 fatty acid desaturase, specific for medium chain (14 |
| T02B5.1 | T02B5.1: Member of the carboxylesterase protein family |
| C05E4.9 | C05E4.9: Putative ortholog of *S. cerevisiae* MLS1 gene product (Malate synthase 1, functions in glyoxylate cycle, has near identity to Da17p) |
| ZC395.5 | ZC395.5: Protein of unknown function |
| H24O09.c | H24O09.c H24O09.c |
| C24B9.9 | C24B9.9: Protein of unknown function, has moderate similarity to *C. elegans* T04C12.1 |
| T20G5.7 | T20G5.7: Protein of unknown function, has moderate similarity to *C. elegans* T20G5.8 |
| K07C6.4 | K07C6.4: Member of the P450 heme-thiolate protein family |
| B0213.15 | B0213.15: Member of the P450 heme-thiolate protein family |
| F09F7.6 | F09F7.6: Protein of unknown function |
| R03E9.1 | R03E9.1: mdl-1: Member of the MAD family of putative transcription factors, interacts with *C. elegans* MAX-1 |
| B0238.1 | B0238.1: Member of the carboxylesterase protein family |
| E01G4.3 | E01G4.3: Protein of unknown function |
| M02D8.4 | M02D8.4: Member of the asparagine synthetase protein family |
| Y6E2A.3 | Y6E2A.3: Protein of unknown function, has weak similarity to *C. elegans* Y6E2A.5 |
| F38E11.2 | F38E11.2: hsp-12.6: Member of the small heat shock protein family |
| F17B5.1 | F17B5.1: Protein with strong similarity to *C. elegans* T20D4.7 gene product [Member of the thioredoxin protein family] |
| K07A1.7 | K07A1.7: Protein with similarity to *D. melanogaster* HDC (headcase) protein, a branching inhibitor produced by specialized tracheal cells |
| F48D6.4 | F48D6.4: Protein of unknown function |
| F11A5.12 | F11A5.12: Protein with similarity to estradiol 17-beta-dehydrogenases; strongly related to *C. elegans* C06B3.4, C06B3.5, F25G6.5, and C56G2.6 |
| C06B3.4 | C06B3.4: Possible estradiol 17 beta-dehydrogenase, member of a protein family |
| H10D18.2 | H10D18.2: Putative paralog of *C. elegans* H10D18.4 |
| Y40B10A.6 | Y40B10A.e Y40B10A.e |
| ZK355.3 | ZK355.3: Protein of unknown function |
| K11G9.6 | K11G9.6: mtl-1: Metallothionein-related, cadmium-binding intestinal protein |
| C02A12.4 | C02A12.4: Member of an uncharacterized protein family with weak similarity to Entemeba histolytica N-acetylmuraminidase |
| AC3.7 | AC3.7: Member of the UDP-glucuronosyltransferase protein family |
| C54D10.3 | C54D10.3: Member of an uncharacterized protein family |
| Upregulated in daf-2 mutants | |
| ZK973.7 | ZK973.7: Protein of unknown function, putative paralog of *C. elegans* ZK973_14.I |
| ZK973.7 | ZK973.7: Protein of unknown function, putative paralog of *C. elegans* ZK973_14.I |
| ZK973.7 | ZK973.7: Protein of unknown function, putative paralog of *C. elegans* ZK973_14.I |
| W10G6.3 | W10G6.3: ifa-2: Putative intermediate filament protein |

TABLE 6-continued

| Gene | Gene product/homology |
|---|---|
| ZK270.2a | ZK270.2 ZK270.2 |
| F16H6.7 | F16H6.7: Member of an uncharacterized protein family |
| F57H12.7 | F57H12.7: Protein of unknown function, has weak similarity to *C. elegans* W06B11.1 |
| F32A5.5 | F32A5.5: Protein with strong similarity to human AQP9, an aquaporin; putative paralog of *C. elegans* C01G6.1 and Y69E1A.G |
| C17G1.4 | C17G1.4: Protein with moderate similarity to *H. sapiens* MUC1 gene product, a transmembrane mucin |
| K12G11.4 | K12G11.4: Member of the alcohol dehydrogenase protein family |
| K12G11.3 | K12G11.3: Member of the alcohol dehydrogenase protein family |
| F21F3.3 | F21F3.3: Protein with strong similarity to *S. cerevisiae* Ste14p, a farnesyl cysteine |
| T07D10.4 | T07D10.4: Member of the C-type lectin protein family |
| H16D19.1 | H16D19.1: Member of the C-type lectin protein family |
| K11D2.2 | K11D2.2: Putative acid ceramidase, has strong similarity to human ASAH, acid ceramidase (N-acylsphingosine amidohydrolase) |
| C52E4.1 | C52E4.1: gcp-1: Cysteine protease expressed in the intestine |
| W08D2.4 | W08D2.4: fat-3: Protein with delta6-fatty acid-desaturase activity |
| F53F4.13 | F53F4.13: Protein of unknown function, has weak similarity to *C. elegans* F20A1.10 |
| C26C6.3 | C26C6.3: Member of the zinc metalloprotease protein family, has strong similarity to *C. elegans* TOH-2, has similarity to *D. melanogaster* and human TGF-beta-like growth factors |
| K08F4.7 | K08F4.7: gst-4: Member of the glutathione S-transferase protein family, has similarity to human and *D. melanogaster* glutathione S-transferases |
| VC5.3 | VC5.3: Ladder protein |
| VC5.3 | VC5.3: Ladder protein |
| E01A2.8 | E01A2.8: Putative paralog of *C. elegans* E01A2.7 |
| K10B3.8 | K10B3.8: gpd-2: Glyceraldehyde-3-phosphate dehydrogenase |
| R09B5.6 | R09B5.6: Member of the hydroxyacyl-CoA dehydrogenase protein family |
| C56A3.2 | C56A3.2: Member of an uncharacterized protein family |
| H22K11.1 | H22K11.1: asp-3: Probable aspartyl protease and an ortholog of human cathepsin D |
| C06G8.1 | C06G8.1: Protein of unknown function, has strong similarity to *C. elegans* K02D7.5, has similarity to *D. melanogaster* SLV (saliva), a putative transmembrane protein |
| Downregulated in daf-2 mutants and with daf-2 RNAi, upregulated with daf-16 RNAi | |
| M60.1 | M60.1: Putative serine proteinase, has strong similarity to human placental serine proteinase, P11 |
| ZK6.10 | ZK6.10: Protein of unknown function, putative paralog of *C. elegans* ZK6.11 |
| C49C3.9 | C49C3.9: Protein of unknown function |
| F55G11.7 | F55G11.7: Member of an uncharacterized protein family |
| F55G11.8 | F55G11.8: Member of an uncharacterized protein family |
| K10D11.1 | K10D11.1: Member of an uncharacterized protein family |
| C32H11.4 | C32H11.4: Member of an uncharacterized protein family |
| Y46C8_103.a | Y46C8_103.a Y46C8_103.a |
| F56D6.2 | F56D6.2: Member of the phospholipase A2 receptor protein family |
| B0365.6 | B0365.6: Member of the C-type lectin protein family |
| ZK1127.10 | ZK1127.10: Member of the cystathionine gamma-lyase protein family |
| C04F12.3 | C04F12.3: Protein with similarity to human B-cell CLL/lymphoma 3 (BCL3) |
| T05A12.3 | T05A12.3: Protein of unknown function, has weak similarity to *C. elegans* R07G3.3 |
| C17H12.8 | C17H12.8: Member of an uncharacterized protein family |
| C17B7.1 | C17B7.1: G protein-coupled receptor, member of a large subfamily that contains ODR-10 odorant response protein, no homolog found in human or *D. melanogaster* |
| F15E11.1 | F15E11.1 F15E11.1 |
| F15E11.12 | F15E11.12 F15E11.12 |
| F22A3.6 | F22A3.6: Possible lysozyme, member of an uncharacterized protein family |
| F58F6.2 | F58F6.2: Putative collagen, has similarity to human COL9A1, alpha-1 collagen, type IX |
| B0478.1 | B0478.1: jnk-1: Neuronally expressed serine/threonine protein kinase of the MAP kinase subfamily |
| F59D8.2 | F59D8.2: vit-4: Member of the vitellogenin protein family; expressed only in *C. elegans* intestinal cells |
| F59D8.1 | F59D8.f F59D8.f |
| ZK757.1 | ZK757.1: Protein of unknown function with similarity to a DHHC zinc finger domain, putative paralog of *C. elegans* B0546.5 protein |
| R11G1.3 | R11G1.3: Member of the glutathione S-transferase protein family, has similarity to *H. sapiens* and *D. melanogaster* glutathione S-transferases |
| C04F6.1 | C04F6.1: vit-5: 170 kDa yolk protein |
| F41A4.1 | F41A4.1: Protein with weak similarity to *C. elegans* let-653 (Putative mucin-like protein required for development beyond the late L1 larval stage or early L2 larval stage) |

TABLE 6-continued

| Gene | Gene product/homology |
|---|---|
| C54G4.6 | C54G4.6: Protein with similarity to human ASMTL protein, acetylserotonin N-methyltransferase-like protein |
| Y19D10A.9 | F15E11.9 F15E11.9 |
| Y19D10A.9 | Y19D10A.j Y19D10A.j |
| Y19D10A.9 | F56A4.j F56A4.j |
| K08D8.5 | K08D8.5: Member of an uncharacterized protein family |
| C32H11.1 | C32H11.1: Member of an uncharacterized protein family |
| T03E6.7 | T03E6.7: Member of the thiol protease protein family |
| R09H10.5 | R09H10.5: Member of the EGF-repeat protein family |
| T25C12.3 | T25C12.3: Member of the EGF-repeat protein family, member of the C-type lectin family |
| K12H4.7 | K12H4.7: Member of the carboxypeptidase protein family |
| F28H7.3 | F28H7.3: Member of the lipase protein family |
| Y38H6C.5 | Y38H6C.5: Putative Zinc finger, CCHC class protein |
| F57F4.3 | F57F4.3: Protein of unknown function, putative paralog of *C. elegans* F57F4.4 |
| F57F4.4 | F57F4.4: Protein of unknown function, putative paralog of *C. elegans* F57F4.3 |
| C12C8.2 | C12C8.2: Member of the cystathionine gamma-lyase protein family |
| W01A11.4 | W01A11.4: Member of the galactoside-binding lectin protein family |
| C08F11.8 | C08F11.8: Member of the UDP-glucuronosyltransferase protein family |
| Y38H6C.1 | Y38H6C.1: Protein of unknown function, has weak similarity to *C. elegans* M02H5.B |
| K06A4.5 | K06A4.5: Putative 3-hydroxyanthranilate 3,4-dioxygenase, has strong similarity to human Hs.108441 gene product (3-hydroxyanthranilic acid dioxygenase) |
| F23H11.7 | F23H11.7: Protein of unknown function |
| F52G3.4 | F52G3.4: Protein with weak similarity to *C. elegans* F33H12.6 |
| F46E10.1 | F46E10.1 F46E10.1 |
| C39E9.1 | C39E9.1: Member of the testis-specific protein TPX-1 like protein family |
| C25F6.3 | C25F6.3: Member of the 4Fe—4S ferredoxins and related iron-sulfur cluster binding protein family |
| F52E1.5 | F52E1.5: Protein of unknown function |
| F28B4.3 | F28B4.3: Member of the EGF-repeat protein family |
| Y106G6H.10 | Y106G6H.10: Protein of unknown function, putative paralog of *C. elegans* Y106G6H.9 |
| Y106G6H.9 | Y106G6H.9: Protein of unknown function, putative paralog of *C. elegans* Y106G6H.10 |
| K06A4.1 | K06A4.1: Putative zinc metalloprotease with similarity over the N-terminus to human and *D. melanogaster* TOLLOID-like proteins, has strong similarity over the middle region to *C. elegans* F56A4.K and Y19D10A.K |
| B0281.5 | B0281.5: Putative potassium voltage-gated channel, Shaw-related subfamily |
| F13A7.9 | F13A7.9: Protein with moderate similarity to *S. cerevisiae* Skp1p, a component of the kinetochore complex and a component of SCF (Skp1p-cullin-F-box) complexes that target proteins for ubiquitin-dependent degradation; also has strong similarity to several other *C. elegans* proteins |
| Y51H7BR.2 | Y51H7BR.2: Protein of unknown function, putative paralog of *C. elegans* Y51H7BR.1 |
| Y38E10A.14 | Y38E10A.n Y38E10A.n |
| Y46H3C__14.c | Y46H3C__14.c Y46H3C__14.c |
| Y9D1A.1 | Y9D1A.1: Protein with moderate similarity to *C. elegans* Y9D1A.A |
| Y49E10.8 | Y49E10.8: Protein of unknown function |
| F56G4.3 | F56G4.3: Protein of unknown function, is identical to *C. elegans* PES-2 |
| F56G4.2 | F56G4.2: pes-2: Protein of unknown function, is identical to *C. elegans* F56G4.3 |
| C52D10.9 | C52D10.9: Protein with similarity to the SKP1 family of proteins, nearly identical to *C. elegans* C52D10.7 |
| C52D10.7 | C52D10.7: Protein with similarity to the SKP1 family of proteins, nearly identical to *C. elegans* C52D10.9 |
| Y56A3A.15 | Y56A3A.15: Member of an uncharacterized protein family |
| C31A11.5 | C31A11.5: G protein-coupled receptor, member of unnamed subfamily with distant homology to SRG subfamily, no homolog found in human or *D. melanogaster* |
| F49E11.7 | F49E11.7: Member of the protein phosphatase protein family |
| C32H11.10 | C32H11.10: Member of an uncharacterized protein family |
| C32H11.9 | C32H11.9: Member of an uncharacterized protein family |
| ZK6.11 | ZK6.11: Protein of unknown function, putative paralog of *C. elegans* ZK6.10 |
| B0554.6 | B0554.6: Member of an uncharacterized protein family |
| F55G11.5 | F55G11.5: Member of an uncharacterized protein family |
| C32H11.12 | C32H11.12: Member of an uncharacterized protein family |
| F35E12.5 | F35E12.5: Member of an uncharacterized protein family |
| C08F8.5 | C08F8.5: Protein of unknown function, has weak similarity to *C. elegans* F38H4.2 |

TABLE 6-continued

| Gene | Gene product/homology |
| --- | --- |
| Y62H9A.3 | Y62H9A.3: Protein of unknown function, has weak similarity to *C. elegans* Y62H9A.5 |
| Y62H9A.4 | Y62H9A.4: Protein of unknown function, has weak similarity to *C. elegans* Y62H9A.6 |
| Y62H9A.6 | Y62H9A.6: Protein of unknown function, has weak similarity to *C. elegans* Y62H9A.4 |
| Y62H9A.5 | Y62H9A.5: Protein of unknown function, has weak similarity to *C. elegans* Y62H9A.3 |
| F49E12.2 | F49E12.2: Member of the calpain protease protein family |
| ZK896.8 | ZK896.8: gcy-18: Protein with a cytoplasmic receptor tyrosine kinase domain and a guanylate cyclase domain, has strong similarity to human natriuretic peptide receptor NPR1 and photoreceptor-specific membrane retina guanylyl cyclase RetGC-2 |
| T24B8.5 | T24B8.5: Protein of unknown function, has weak similarity to *C. elegans* F49F1.7 |
| K02H11.2 | K02H11.2: G protein-coupled receptor, member of a large subfamily that contains ODR-10 odorant response protein, no homolog found in human or *D. melanogaster* |
| Y22F5A.5 | Y22F5A.5: Member of an uncharacterized protein family with weak similarity to Entemeba histolytica N-acetylmuraminidase |
| C25B8.3 | C25B8.3: cpr-6: Member of the Cathepsin B-like Cysteine Protease family |
| Y55B1AR.1 | Y55B1AR.1: Protein with weak similarity to *C. elegans* W09H1.6 (Galactoside-binding lectin) |
| F49C12.7 | F49C12.7: Member of an uncharacterized protein family |
| ZK896.5 | ZK896.5: Member of an uncharacterized protein family |
| W02D9.7 | W02D9.7: Protein of unknown function |
| F49F1.1 | F49F1.1: Member of an uncharacterized protein family |

What is claimed is:

1. A method for identifying a small organic molecule that modulates aging, the method comprising:
   (i) contacting a small organic molecule with a mammalian cell comprising a heat shock factor-1 (HSF-1) polypeptide, wherein the HSF-1 polypeptide comprises an amino acid sequence at least 95% identical to a human HSF-1 polypeptide analog comprising the amino acid sequence of SEQ ID No. 11;
   (ii) determining the functional effect of the small organic molecule upon the cell comprising the HSF-1 polypeptide wherein the functional effect is determined in a mammalian host cell in vitro and wherein the functional effect is increased expression of the HSF-1 polypeptide in the mammalian host cell.

2. The method of claim 1, wherein the HSF-1 polypeptide is recombinant.

3. The method of claim 1, wherein the polypeptide comprises an amino acid sequence identical to the HSF-1 human homolog.

4. The method of claim 1, wherein the host cell is a mouse or human cell.

* * * * *

SEQUENCE LISTING

```
<160> NUMBER OF SEQ ID NOS: 12

<210> SEQ ID NO 1
<211> LENGTH: 285
<212> TYPE: PRT
<213> ORGANISM: Caenorhabditis elegans
<220> FEATURE:
<223> OTHER INFORMATION: cytochrome C1 component of complex III, gene
      C54G4.8 (CYC1)

<400> SEQUENCE: 1

Met Gln Arg Ala Val Val Gln Gly Ser Lys Arg Gly Leu Ala Ala Leu
  1               5                  10                  15

Ala Gly Val Thr Ala Ala Ser Gly Met Gly Leu Val Tyr Ala Leu Glu
                 20                  25                  30

Asn Ser Val Ser Ala Ser Gly Asp Asn Val His Pro Tyr Ala Leu Pro
             35                  40                  45

Trp Ala His Ser Gly Pro Phe Ser Ser Phe Asp Ile Ala Ser Val Arg
         50                  55                  60

Arg Gly Tyr Glu Val Tyr Lys Gln Val Cys Ala Ala Cys His Ser Met
 65                  70                  75                  80

Lys Phe Leu His Tyr Arg His Phe Val Asp Thr Ile Met Thr Glu Glu
                 85                  90                  95

Glu Ala Lys Ala Glu Ala Asp Ala Leu Ile Asn Asp Val Asp Asp
                100                 105                 110

Lys Gly Ala Ser Ile Gln Arg Pro Gly Met Leu Thr Asp Lys Leu Pro
            115                 120                 125

Asn Pro Tyr Pro Asn Lys Lys Ala Ala Ala Ala Asn Asn Gly Ala
        130                 135                 140

Ala Pro Pro Asp Leu Ser Leu Met Ala Leu Ala Arg His Gly Gly Asp
145                 150                 155                 160
```

-continued

```
Asp Tyr Val Phe Ser Leu Leu Thr Gly Tyr Leu Glu Ala Pro Ala Gly
                165                 170                 175

Val Lys Val Asp Asp Gly Lys Ala Tyr Asn Pro Tyr Phe Pro Gly Gly
            180                 185                 190

Ile Ile Ser Met Pro Gln Gln Leu Phe Asp Glu Gly Ile Glu Tyr Lys
        195                 200                 205

Asp Gly Thr Pro Ala Thr Met Ser Gln Gln Ala Lys Asp Val Ser Ala
    210                 215                 220

Phe Met His Trp Ala Ala Glu Pro Phe His Asp Thr Arg Lys Lys Trp
225                 230                 235                 240

Ala Leu Lys Ile Ala Ala Leu Ile Pro Phe Val Ala Val Val Leu Ile
                245                 250                 255

Tyr Gly Lys Arg His Ile Trp Ser Phe Thr Lys Ser Gln Lys Phe Leu
            260                 265                 270

Phe Lys Thr Val Lys Gly Arg Glu Pro Pro Lys Ala Gln
        275                 280                 285
```

<210> SEQ ID NO 2
<211> LENGTH: 401
<212> TYPE: PRT
<213> ORGANISM: Caenorhabditis elegans
<220> FEATURE:
<223> OTHER INFORMATION: NADH oxidoreductase component of complex I
      (NADH/ubiquinone oxidoreductase), gene T10E9.7 (NUO2)

<400> SEQUENCE: 2

```
Met Asp Ser Glu Ile Leu Asn Tyr Pro Ile His Arg Phe Leu Asp Ser
 1               5                  10                  15

Ser Leu Leu Gly Gln Phe Ile Gly Pro Glu Gly Ser Asn Ile Tyr Lys
            20                  25                  30

Ile Glu Lys Tyr Asn Lys Val Ala Leu Asp Ile Trp Lys Asn Asp Glu
        35                  40                  45

Glu Asn Ser Asn Val Arg Ile Thr Gly Pro Tyr Trp Asn Leu Lys Ser
    50                  55                  60

Ala Leu Asn Asp Val Leu Glu Leu Val Ser Thr Ile Arg Asn Lys Asn
65                  70                  75                  80

Gln Arg Tyr Lys Phe Glu Met Pro Ser Lys Asp Ile Gly Phe Leu Ile
                85                  90                  95

Gly Lys Asn Gly Ala Lys Ile Asn Glu Ile Lys Leu Ser Ser Asn Val
            100                 105                 110

Asp Val His Phe Glu Arg Asn Asn Glu Asn Arg Asp Asn Gly Glu Thr
        115                 120                 125

Asp Gly Arg Val Lys Met Leu Gly Ser Val Ile Arg Gln Ala Val Ser
    130                 135                 140

Arg Gln Ile Val Arg Asn Ser Pro Ile Ser Thr Thr Ala Ala Val Ala
145                 150                 155                 160

Gln Thr Asn Gln Thr Gly Asp Lys Lys Glu Ser Pro Lys Lys Pro Thr
                165                 170                 175

Ile Trp Lys Ile Asp Glu His Lys Arg Glu Arg Leu Ala Asn Phe Gly
            180                 185                 190

Lys Tyr Ala Ala Glu Cys Leu Pro Lys Phe Val Gln Lys Val Gln Phe
        195                 200                 205

Ala Ala Gly Asp Glu Leu Glu Leu Leu Ile His Pro Ser Gly Val Val
    210                 215                 220

Pro Val Leu Ser Phe Leu Lys Gly Asn His Ser Ala Gln Phe Thr Asn
```

```
                225                 230                 235                 240
Leu Thr Phe Ile Thr Gly Met Asp Val Pro Thr Arg Lys Asn Arg Leu
                    245                 250                 255
Glu Val Ile Tyr Ser Leu Tyr Ser Val Arg Phe Asn Ala Arg Val Arg
                260                 265                 270
Val Arg Thr Tyr Thr Asp Glu Ile Ala Pro Ile Asp Ser Ala Thr Pro
            275                 280                 285
Val Phe Lys Gly Ala Asp Trp Phe Glu Arg Glu Val Tyr Asp Met Tyr
        290                 295                 300
Gly Val Trp Phe Asn Asn His Pro Asp Leu Arg Arg Ile Leu Thr Asp
305                 310                 315                 320
Tyr Gly Phe Glu Gly His Pro Phe Arg Lys Asp Tyr Pro Leu Ser Gly
                325                 330                 335
Tyr Asn Glu Val Arg Tyr Asp Pro Glu Leu Lys Arg Val Val Tyr Glu
                340                 345                 350
Pro Ser Glu Leu Ala Gln Glu Phe Arg Lys Phe Asp Leu Asn Thr Pro
                355                 360                 365
Trp Glu Thr Phe Pro Ala Phe Arg Asn Gln Ser Ile Thr Ser Gly Tyr
        370                 375                 380
Glu Thr Ile Leu Glu Val Ala Glu Pro Thr Pro Ala Thr Pro Gln Asn
385                 390                 395                 400
Lys

<210> SEQ ID NO 3
<211> LENGTH: 207
<212> TYPE: PRT
<213> ORGANISM: Caenorhabditis elegans
<220> FEATURE:
<223> OTHER INFORMATION: ATP synthase component of complex V (delta
      family), gene F27C1.7 (ATP3)

<400> SEQUENCE: 3

Met Ala Gln Leu Met Lys Arg Gly Phe Ser Thr Ser Ala Ala Leu Ala
1               5                   10                  15
Lys Ala Gln Leu Val Lys Thr Pro Ile Gln Val His Gly Val Glu Gly
                20                  25                  30
Arg Tyr Ala Ala Ala Leu Tyr Ser Ala Gly His Lys Gln Asn Lys Leu
            35                  40                  45
Asp Gln Ile Ser Thr Asp Leu Asn Asn Val Arg Ser Val Tyr Lys Asp
        50                  55                  60
Asn Lys Lys Phe Gln Glu Phe Val Leu Asp Pro Thr Leu Lys Ala Asn
65                  70                  75                  80
Lys Lys Lys Thr Ala Ile Glu Ala Ile Ser Thr Lys Leu Gly Leu Thr
                85                  90                  95
Lys Glu Thr Gly Asn Phe Leu Gly Leu Leu Ala Glu Asn Gly Arg Leu
                100                 105                 110
Asn Lys Leu Glu Ser Val Val Ser Ser Phe Glu Ser Ile Met Arg Ala
            115                 120                 125
His Arg Gly Glu Leu Phe Val Gln Val Thr Ser Ala Glu Glu Leu Ser
        130                 135                 140
Ser Ser Asn Gln Lys Ala Leu Ser Asp Ala Leu Ser Lys Ile Gly Lys
145                 150                 155                 160
Ser Gly Gln Lys Leu Thr Val Thr Tyr Ala Val Lys Pro Ser Ile Leu
                165                 170                 175
Gly Gly Leu Val Val Thr Ile Gly Asp Lys Tyr Val Asp Leu Ser Ile
```

```
                        180                 185                 190
Ala Ser Arg Val Lys Lys Tyr Lys Asp Ala Leu Ala Thr Ala Ile
        195                 200                 205

<210> SEQ ID NO 4
<211> LENGTH: 132
<212> TYPE: PRT
<213> ORGANISM: Caenorhabditis elegans
<220> FEATURE:
<223> OTHER INFORMATION: cytochrome C oxidase component of complex IV,
      gene F26E4.9 (CCO1)

<400> SEQUENCE: 4

Met Ala Gln Leu Ala Lys Thr Ala Val Ala Ala Leu Ser Lys Lys Leu
  1               5                  10                  15

Val Ala Pro Ala Ala Val Ala Arg Arg Thr Leu Ala Thr Glu Ala Ser
             20                  25                  30

Pro Glu Asp Tyr Gly Tyr Tyr Pro Asp Pro Leu Glu His Ala Thr Gly
         35                  40                  45

Arg Glu Lys Lys Met Leu Leu Ala Arg Leu Ala Gly Asp Asp Arg Tyr
     50                  55                  60

Glu Pro Lys Val Tyr Tyr Arg Ala Glu Ala Ser Thr Lys Gln Lys Pro
 65                  70                  75                  80

Asn Leu Val Pro Ser His Tyr Asp Phe Arg Ile Ile Gly Cys Met Cys
                 85                  90                  95

Glu Gln Asp Ser Gly His Val Asn Phe Met Thr Ile Arg Lys Gly Asp
            100                 105                 110

Pro Lys Arg Cys Glu Cys Gly His Trp Phe Lys Gly Val Asp Ala Asp
        115                 120                 125

Pro Glu Ser Ile
    130

<210> SEQ ID NO 5
<211> LENGTH: 551
<212> TYPE: PRT
<213> ORGANISM: Caenorhabditis elegans
<220> FEATURE:
<223> OTHER INFORMATION: glucose phosphate isomerase (phosphoglucose
      isomerase), gene Y87G2A.8 (GPI-1)

<400> SEQUENCE: 5

Met Ser Leu Ser Gln Asp Ala Thr Phe Val Glu Leu Lys Arg His Val
  1               5                  10                  15

Glu Ala Asn Glu Lys Asp Ala Gln Leu Leu Glu Leu Phe Glu Lys Asp
             20                  25                  30

Pro Ala Arg Phe Glu Lys Phe Thr Arg Leu Phe Ala Thr Pro Asp Gly
         35                  40                  45

Asp Phe Leu Phe Asp Phe Ser Lys Asn Arg Ile Thr Asp Glu Ser Phe
     50                  55                  60

Gln Leu Leu Met Arg Leu Ala Lys Ser Arg Gly Val Glu Glu Ser Arg
 65                  70                  75                  80

Asn Ala Met Phe Ser Ala Glu Lys Ile Asn Phe Thr Glu Asn Arg Ala
                 85                  90                  95

Val Leu His Val Ala Leu Arg Asn Arg Ala Asn Arg Pro Ile Leu Val
            100                 105                 110

Asp Gly Lys Asp Val Met Pro Asp Val Asn Arg Val Leu Ala His Met
        115                 120                 125

Lys Glu Phe Cys Asn Glu Ile Ile Ser Gly Ser Trp Thr Gly Tyr Thr
```

-continued

```
            130                 135                 140
Gly Lys Lys Ile Thr Asp Val Val Asn Ile Gly Ile Gly Gly Ser Asp
145                 150                 155                 160

Leu Gly Pro Leu Met Val Thr Glu Ser Leu Lys Asn Tyr Gln Ile Gly
                165                 170                 175

Pro Asn Val His Phe Val Ser Asn Val Asp Gly Thr His Val Ala Glu
                180                 185                 190

Val Thr Lys Lys Leu Asn Ala Glu Thr Thr Leu Phe Ile Ile Ala Ser
                195                 200                 205

Lys Thr Phe Thr Thr Gln Glu Thr Ile Thr Asn Ala Glu Thr Ala Lys
210                 215                 220

Glu Trp Phe Leu Ala Lys Ala Gly Asp Ala Gly Ala Val Ala Lys His
225                 230                 235                 240

Phe Val Ala Leu Ser Thr Asn Val Thr Lys Ala Val Glu Phe Gly Ile
                245                 250                 255

Asp Glu Lys Asn Met Phe Glu Phe Trp Asp Trp Val Gly Gly Arg Tyr
                260                 265                 270

Ser Leu Trp Ser Ala Ile Gly Leu Ser Ile Ala Val His Ile Gly Phe
                275                 280                 285

Asp Asn Tyr Glu Lys Leu Leu Asp Gly Ala Phe Ser Val Asp Glu His
                290                 295                 300

Phe Val Asn Thr Pro Leu Glu Lys Asn Ile Pro Val Ile Leu Ala Met
305                 310                 315                 320

Ile Gly Val Leu Tyr Asn Asn Ile Tyr Gly Ala Glu Thr His Ala Leu
                325                 330                 335

Leu Pro Tyr Asp Gln Tyr Met His Arg Phe Ala Ala Tyr Phe Gln Gln
                340                 345                 350

Gly Asp Met Glu Ser Asn Gly Lys Phe Val Thr Arg His Gly Gln Arg
                355                 360                 365

Val Asp Tyr Ser Thr Gly Pro Ile Val Trp Gly Glu Pro Gly Thr Asn
                370                 375                 380

Gly Gln His Ala Phe Tyr Gln Leu Ile His Gln Gly Thr Arg Leu Ile
385                 390                 395                 400

Pro Ala Asp Phe Ile Ala Pro Val Lys Thr Leu Asn Pro Ile Arg Gly
                405                 410                 415

Gly Leu His His Gln Ile Leu Leu Ala Asn Phe Leu Ala Gln Thr Glu
                420                 425                 430

Ala Leu Met Lys Gly Lys Thr Ala Ala Val Ala Glu Ala Glu Leu Lys
                435                 440                 445

Ser Ser Gly Met Ser Pro Glu Ser Ile Ala Lys Ile Leu Pro His Lys
450                 455                 460

Val Phe Glu Gly Asn Lys Pro Thr Thr Ser Ile Val Leu Pro Val Val
465                 470                 475                 480

Thr Pro Phe Thr Leu Gly Ala Leu Ile Ala Phe Tyr Glu His Lys Ile
                485                 490                 495

Phe Val Gln Gly Ile Ile Trp Asp Ile Cys Ser Tyr Asp Gln Trp Gly
                500                 505                 510

Val Glu Leu Gly Lys Gln Leu Ala Lys Val Ile Gln Pro Glu Leu Ala
                515                 520                 525

Ser Ala Asp Thr Val Thr Ser His Asp Ala Ser Thr Asn Gly Leu Ile
                530                 535                 540

Ala Phe Ile Lys Asn Asn Ala
545                 550
```

<210> SEQ ID NO 6
<211> LENGTH: 201
<212> TYPE: PRT
<213> ORGANISM: Caenorhabditis elegans
<220> FEATURE:
<223> OTHER INFORMATION: GTPase, gene T23H2.5

<400> SEQUENCE: 6

```
Met Ala Arg Arg Pro Tyr Asp Met Leu Phe Lys Leu Leu Leu Ile Gly
  1               5                  10                  15

Asp Ser Gly Val Gly Lys Thr Cys Ile Leu Tyr Arg Phe Ser Asp Asp
                 20                  25                  30

Ala Phe Asn Thr Thr Phe Ile Ser Thr Ile Gly Ile Asp Phe Lys Ile
             35                  40                  45

Lys Thr Ile Glu Leu Lys Gly Lys Lys Ile Lys Leu Gln Ile Trp Asp
 50                  55                  60

Thr Ala Gly Gln Glu Arg Phe His Thr Ile Thr Thr Ser Tyr Tyr Arg
 65                  70                  75                  80

Gly Ala Met Gly Ile Met Leu Val Tyr Asp Ile Thr Asn Ala Lys Ser
             85                  90                  95

Phe Asp Asn Ile Ala Lys Trp Leu Arg Asn Ile Asp Glu His Ala Ser
            100                 105                 110

Glu Asp Val Val Lys Met Ile Leu Gly Asn Lys Cys Asp Met Ser Asp
            115                 120                 125

Arg Arg Val Val Ser Arg Glu Arg Gly Glu Lys Ile Ala Gln Asp His
        130                 135                 140

Gly Ile Ser Phe His Glu Thr Ser Ala Lys Leu Asn Val His Val Asp
145                 150                 155                 160

Thr Ala Phe Tyr Asp Leu Ala Glu Ala Ile Leu Ala Lys Met Pro Asp
                165                 170                 175

Ser Thr Asp Glu Gln Ser Arg Asp Thr Val Asn Pro Val Gln Pro Gln
            180                 185                 190

Arg Gln Ser Ser Ser Gly Gly Cys Cys
        195                 200
```

<210> SEQ ID NO 7
<211> LENGTH: 396
<212> TYPE: PRT
<213> ORGANISM: Caenorhabditis elegans
<220> FEATURE:
<223> OTHER INFORMATION: llw-1 (long-lived worm protein), gene Y54G11A.8

<400> SEQUENCE: 7

```
Met Leu Pro Ser Met Ser Lys Leu Cys Thr Ser Thr Val Arg Pro Val
  1               5                  10                  15

Ala Ala Ala Phe Ser Thr Gly Thr Thr Arg Gln His His Ser Ser Gly
                 20                  25                  30

Arg Ser Arg Gln Gln His His Arg His Gly Gly Ser Gly Gly Lys Thr
             35                  40                  45

Asn Gly Gly Gly Arg Trp Ser Arg Tyr Gly Lys Ser Ala Ala Thr Gly
         50                  55                  60

Gly Thr Thr Val Leu Ala Leu Ser Trp Met Thr Thr Ile Lys Asp Val
 65                  70                  75                  80

Leu Gly Ile Glu Lys Val Gln Leu Asp Ala Asp Pro Leu Lys Glu Lys
                 85                  90                  95

Val Lys Gln Ser Trp Leu Tyr Arg Lys Arg Arg Gln Tyr Asp Asp Ala
```

-continued

```
               100                 105                 110
Ile Gln Val Leu Gln Leu Ala Leu Glu Ala Glu Arg Lys Glu
            115                 120                 125

Asp Met Pro Ile Thr Arg Val Tyr Asp Glu Met Ala Asn Thr Phe Tyr
            130                 135                 140

Glu Lys Met Asn Leu Asp Glu Ala Asp Lys Tyr Phe Arg Ile Val Ile
145                 150                 155                 160

Gln Arg Leu Val Gln Leu His Gly Lys Lys Asp Phe Asp Pro Glu Phe
                165                 170                 175

Ile Gly Val Ser Leu Lys Leu Ala Asp Ile Leu Ala His Arg Gly Asp
            180                 185                 190

Leu Glu Ser Ala Glu Ser Gly Phe Lys His Cys Val Arg Arg Gln Met
            195                 200                 205

Lys Val Met Glu Glu His Met Lys Lys Phe Ser Val Ala His Gly Ala
210                 215                 220

Leu Val Glu Asp Arg His Thr Val Asp Thr Phe Gly Pro Met Tyr Thr
225                 230                 235                 240

Asp Pro Ile Ala Leu Phe Gly Met Thr Leu Glu Ala Tyr Ala Asn Phe
                245                 250                 255

Leu Ile Asn Tyr Cys Gly Glu Thr Arg Met Ala Glu Val Glu Glu Tyr
                260                 265                 270

Ile Asp Glu Val Met Lys Ile Ser Tyr Gln Ile Tyr Gly Ala Ser Ser
            275                 280                 285

Ala His Thr Ile Asn Met Leu Asn Asn Phe Gly Ala Thr Leu Val Leu
            290                 295                 300

Lys Asn Arg Phe Glu Leu Ala Lys Lys Tyr Leu Ala Ile Gly Val Asp
305                 310                 315                 320

Arg Ile Leu Tyr Val Asn Glu Cys Ala His Met Leu Pro Gly Tyr Tyr
                325                 330                 335

Cys Asn Tyr Ala Glu Ser Leu Phe His Thr Gly Gln Lys Asn Glu Ala
                340                 345                 350

Leu Glu Phe Ala Arg Lys Ala Val Gln Met Ser Arg Ser Gly Asp Asp
            355                 360                 365

Arg Val Arg His Tyr Thr Gln Asn Phe Leu Asn Asp Leu Glu Lys Asp
            370                 375                 380

Ile Asn Arg Gly Lys Pro Lys Ser Trp Trp Phe Phe
385                 390                 395

<210> SEQ ID NO 8
<211> LENGTH: 189
<212> TYPE: PRT
<213> ORGANISM: Caenorhabditis elegans
<220> FEATURE:
<223> OTHER INFORMATION: llw-2 (long-lived worm protein), gene F59E12.10

<400> SEQUENCE: 8

Met Asn Ala Ser Ser Arg Thr Lys Pro Ala Ile Asp Leu Asn Lys Val
1               5                  10                  15

Pro Pro Ile Asp His His Arg Thr Ala Val Thr Phe Asn Cys Leu Ile
            20                  25                  30

Met Lys Met Thr Glu Met Leu Asn Asn Phe Gly Asn Lys Met Glu Asp
        35                  40                  45

Ile Leu Glu Lys Ala Glu Gln Ser Leu Asp Thr Ala Asp Arg Lys Leu
    50                  55                  60

Arg Leu Met Glu Ser Lys Leu Ala Gly Met Ser Leu Glu Asp Lys Ser
```

-continued

```
                65                  70                  75                  80
Thr Thr Ala Thr Pro Ser Ser Ala Pro Glu Ile Asp Glu Ile His Glu
                    85                  90                  95
Ser Asn Pro Ser Ser Ser Gln Ile Val Glu Glu Thr Val Glu Glu Lys
                100                 105                 110
Pro Glu Glu His Thr Thr Thr Val Leu Ile Lys Asp Asp Pro Ala Tyr
                115                 120                 125
Ser Lys Tyr Phe Lys Met Leu Lys Leu Gly Val Leu Glu Ala Gly Val
                130                 135                 140
Ile Gln Lys Met Lys Ser Glu Gly Val Asp Pro Ser Ile Leu Lys Arg
145                 150                 155                 160
Gly Asp Glu Pro Ser Arg Pro Gln Ala Gln Thr Ser Arg Asn Tyr Glu
                165                 170                 175
Ser Ser Gly Glu Ser Thr Ala Ser Phe Ser Asp Ser Asp
                180                 185
```

<210> SEQ ID NO 9
<211> LENGTH: 497
<212> TYPE: PRT
<213> ORGANISM: Caenorhabditis elegans
<220> FEATURE:
<223> OTHER INFORMATION: llw-3 (long-lived worm protein), gene Y48E1B.1

<400> SEQUENCE: 9

```
Met Tyr His Val Pro Leu Ile Pro Arg Asp Ala Gly Arg Glu Glu Thr
1               5                   10                  15
Ile Phe Arg Ile Asn Gln Ser Leu Gln Lys Leu Leu Arg Val Ser Asp
                20                  25                  30
Glu Ile Phe Asp Arg Val Glu His Arg Ile Thr Arg Ile His Gly Lys
                35                  40                  45
Ala Glu Ala Ile Asp Arg Arg Thr Glu Val Leu Glu Lys Lys Leu Glu
                50                  55                  60
Ser Leu Gln Glu Ser Asp Lys Val Ile Thr Phe Thr Leu Pro Arg Gln
65                  70                  75                  80
Leu Pro Lys Leu Pro Glu Glu Pro Pro Thr Ser Thr Ser Leu Phe Arg
                    85                  90                  95
Ile Asn Ile Asp Thr Glu His Phe Pro Gly Ser Glu Glu Leu Pro Ala
                100                 105                 110
Phe Arg Arg Ala Asp Asp His Val Leu Arg Pro Cys Glu Pro Ile Asp
                115                 120                 125
Phe Thr Tyr Glu Leu Asn Lys Pro Asp Lys Phe Phe Leu Thr Ser Gln
                130                 135                 140
Val Leu Lys Glu Tyr Glu Gln Lys Gly Trp Glu Arg Tyr Lys Lys Arg
145                 150                 155                 160
Leu Leu Gly Gly Leu Arg Glu Leu Ser Arg Ser Pro Glu His Ile Ala
                165                 170                 175
Glu Leu Phe Tyr Ala Gly Thr Ser Ile Pro Ala Phe Glu Gly Val Ser
                180                 185                 190
Gly Asp Phe Ser Lys Lys Ala Leu Asp Ala Asp Asp Gly Gly Thr
                195                 200                 205
Ser Arg Ser Gly Arg Thr Thr Asp Glu Leu Ala Gln Leu Arg Leu His
                210                 215                 220
Glu Gln Leu Leu Glu Asp Thr Ala Leu Ser Ser Thr Leu Met Gln Glu
225                 230                 235                 240
Asp Ser Leu Asp Asp Asn His Pro Leu Ala Phe Arg Ile Asn Phe Asn
```

```
                    245                 250                 255
Glu Lys Lys Lys Lys Thr Ala Lys Met Val Glu Met Pro Asp Ser Leu
                260                 265                 270

Pro Asn Leu Lys Gly His Ala His Asp Phe Thr Leu Arg Asp Pro Glu
            275                 280                 285

Ile Asp Glu Asp Arg Leu Leu Asp Ile Leu Pro Ala Asp Asp Gln Ile
        290                 295                 300

Pro Glu Ala Ser Glu Pro Thr Glu Ala Glu Ala Asp Ala Pro Thr Thr
305                 310                 315                 320

Phe Ile Leu Pro Pro Pro Pro Met Lys Leu Asp Pro Ser Pro
                325                 330                 335

Gln Pro Ala Ala Thr Pro Val Glu Ile Thr Glu Ile Pro Pro Ile Ile
            340                 345                 350

Ser Pro Pro Ala Pro Pro Pro Pro Pro Pro Pro Pro Pro Pro
        355                 360                 365

Pro Pro Gln Thr Pro Ser Ala Ser Ser Ser Val Thr Phe Ser Pro Thr
    370                 375                 380

Lys Ser Val Asp Gly Gly Arg Ser Asp Leu Met Ala Ala Ile Arg Ala
385                 390                 395                 400

Ala Gly Gly Ala Gly Asn Ala Lys Leu Ser Arg Ile Ala Glu Lys Pro
                405                 410                 415

Lys Arg Lys Gly Lys Phe Asp Gly Ile Leu Glu Ser Ser Ala Leu Leu
            420                 425                 430

Gly Ala Ser Glu Thr Pro Arg Asn Ser Ala Pro Ala Pro Asp Gly Gly
        435                 440                 445

Gly Gly Gly Gly Asp Leu Met Ser Ala Leu Ser Lys Ala Leu Asp Ala
    450                 455                 460

Arg Arg Lys Ala Ile Asn Gly Lys Val Glu Ala Gln Pro Pro Ala Lys
465                 470                 475                 480

Val Ser Ser Thr Ile Pro Ala Pro Pro Asn Phe Asp Asp Glu Glu Trp
                485                 490                 495

Asp

<210> SEQ ID NO 10
<211> LENGTH: 884
<212> TYPE: PRT
<213> ORGANISM: Caenorhabditis elegans
<220> FEATURE:
<223> OTHER INFORMATION: llw-4 (long-lived worm protein), gene F45H10.4

<400> SEQUENCE: 10

Met Arg Ile Ile Ala Cys Ser Leu Leu Ile Ala Ser Leu Ile Pro Thr
1               5                   10                  15

Val Ile Gly Leu Lys Ser Asn Arg Thr Ser Cys Phe His Tyr Val Ser
                20                  25                  30

Cys Leu Glu Ala Thr Glu Ala Asn Leu Lys Gln Cys Ala Gly Gly Thr
            35                  40                  45

Ala Ile Ser Leu Thr Leu Glu Ala Lys Asp Val Asn Ile Arg Asp Leu
        50                  55                  60

Val Lys Tyr Arg Ala Leu Glu Phe Val Gly Cys Gln Asp Arg Leu Leu
65                  70                  75                  80

Lys Glu Val Val Asp Phe Glu Ser Leu Gln Ile Leu Val Asn Glu Asp
                85                  90                  95

Ala Arg Glu Cys Phe Glu Lys Leu Pro Glu Ser Ser Lys Arg Val Glu
            100                 105                 110
```

```
Glu Phe Thr Asp Ser Cys Asp Tyr Val Gln Pro Val Ser Arg Asn Ala
        115                 120                 125

Ser Lys Gly Asp Ala Leu Gln Cys Leu Ile Glu Phe Lys Gln Asp Arg
    130                 135                 140

Glu Tyr Cys Glu Ser Leu Leu Glu Cys Cys Pro Asp His Thr Arg Cys
145                 150                 155                 160

Gly Glu Arg Met Asn Ala Val Ser Leu Ser Tyr Gln Asn Ala Arg Val
                165                 170                 175

Lys Ala Glu Gln Ile Val Tyr Ser Met Ile Ser Cys Ile Val Val Asn
            180                 185                 190

Asp Pro Arg Phe Leu Arg Glu Gly Ala Arg Leu Gln Ser Leu Arg Asp
        195                 200                 205

Pro Tyr Arg Asn Ala Gly Val Pro Phe Leu Arg Pro Asp Ala Tyr Thr
    210                 215                 220

Glu Ala Arg Ile Thr Arg Arg Leu Ala Leu Thr Ser Thr Ala Thr Leu
225                 230                 235                 240

Ser Gln Arg Arg Glu Arg Phe Leu Lys Lys Tyr Ser Gln Ile Arg Gln
                245                 250                 255

Val Val Ala Gln Asn Leu Phe Gly Gln Gln Arg Leu Thr Arg Pro
            260                 265                 270

Val Glu Asp Leu Val Thr Glu Thr Ser Ser Lys Leu Ala Val Glu Glu
        275                 280                 285

Ala Pro Glu Glu Thr Thr Thr Gln Glu Glu Thr Thr Asp Ala Ser
    290                 295                 300

Glu Val Thr Thr Thr Lys Ala Val Glu Glu Thr Glu Glu Val Thr
305                 310                 315                 320

Glu Glu Ala Thr Glu Ala Thr Glu Ala Pro Val Ala Thr Thr Lys Glu
                325                 330                 335

Ser Ser Glu Met His Val Asn Thr Ile Arg Asn Met Ile Arg Ser Ala
            340                 345                 350

Ser Glu Lys Asp Leu Ser Lys Tyr Val Thr Leu Ile Ser Glu Gly Lys
        355                 360                 365

Phe Ser Glu Leu Phe Glu Leu Ala Glu Gln Lys Lys Leu Thr Leu Thr
    370                 375                 380

Ser Lys Phe Asp Glu Lys Leu Ser Ser Lys Met Ala Lys Leu Lys Asp
385                 390                 395                 400

Leu Ile Asn Glu Ala Leu Ser Glu Lys Glu Lys Ser Gly Glu Ile Glu
                405                 410                 415

Gln Ala Met Glu Lys Phe Glu Lys Pro Glu Lys Ser Glu Leu Val Ala
            420                 425                 430

Met Glu Asp Lys Asp Thr Pro Ala Val Phe Thr Ile Ser Asp Ser Leu
        435                 440                 445

Lys His Lys Lys Ala Glu Ala Lys Leu Ala His Thr Ile Val Ser Arg
    450                 455                 460

Asn Val Val Glu Ala Glu Asn Ala Ile Glu Lys Glu Val Val Glu Pro
465                 470                 475                 480

Lys Ala Glu Glu Lys Lys Val Lys Glu Glu Asp Val Lys Ala Val Ala
                485                 490                 495

Glu Glu Lys Lys Glu Glu Lys Lys Pro Gly Lys Leu Pro Met Lys Ile
            500                 505                 510

Glu Lys Leu Glu Lys Pro Val Asp Thr Lys Ser Glu Asn His Glu Leu
        515                 520                 525
```

Lys Lys Val Leu Asp Asp Lys Glu Arg Ala Leu Leu Val Glu Ser Glu
530                 535                 540

Ile Lys Asn Thr Ala Glu Glu Thr Lys Pro Lys Val Glu Ser Phe Lys
545                 550                 555                 560

Ser Glu Glu Thr Thr Val Ala Ile Asp Asp Met Pro Ala Leu Glu Lys
                565                 570                 575

Glu Glu Ser Ala Glu Lys Lys Glu Thr Thr Gly Glu Pro Thr Thr Thr
            580                 585                 590

Glu Ala Ala Val Glu Thr Thr Glu Ala Ser Glu Thr Pro Lys Pro Glu
        595                 600                 605

Ala Lys Pro Glu Leu Leu Ser Asn Leu Glu Asp Val Leu Thr Leu Thr
610                 615                 620

Thr Pro Glu Thr Glu Thr Ile Glu Gly Ser Gly Glu Arg Glu Pro
625                 630                 635                 640

Thr Thr Ser Ala Pro Ala Glu Ala Thr Ser Glu Ile Thr Leu Leu
                645                 650                 655

Lys Ser Ser Asp Val Ala Val Ile Glu Asn Val Lys Arg Ile Arg
            660                 665                 670

Pro Arg Thr Glu Gln Thr His Cys Gln Gln Tyr Ala Ser Cys Trp Gln
        675                 680                 685

Thr Val Leu Asp Tyr Glu Gln Gln Cys Asp Arg Lys Tyr Ser Thr Glu
690                 695                 700

Val Leu Ser His Gly Ile Asp Asp Ser Glu Ile Leu Asn Ile Leu His
705                 710                 715                 720

Asn Ser Ser Ile Ser His His Glu Ile Val Leu Lys Ala Cys Leu Arg
                725                 730                 735

Pro Leu Asp Arg Ser Val His Ser Thr Leu Lys Gln Leu Leu Val Ile
            740                 745                 750

Gln Arg Gly Val Arg Lys Ala Cys Leu Glu Leu Gly Arg Asn Lys Ile
        755                 760                 765

Ala Val Thr Asp Ser Glu Glu Ala Leu Cys Asn Thr Glu Ile Pro Ser
770                 775                 780

Thr Ala Ala Ile Asp Glu Phe Ile Ser Ser Glu His Val Arg Ser Gln
785                 790                 795                 800

Ser Asn His Leu Thr Cys Arg Ala Lys Leu Glu Pro Ile Arg Glu Thr
                805                 810                 815

Cys Ser Ile Val Arg Asn Cys Cys Ala Ser Val Asp Thr Cys Asp Asn
            820                 825                 830

Tyr Ile Ser Ser Ser Pro Val Lys Lys Leu Glu Thr Glu Ala Ile Arg
        835                 840                 845

Arg Leu Val Lys Lys Gln Asn Asp Cys Glu Thr Lys Met Leu Gln Thr
850                 855                 860

Leu Ser Tyr Ile His Glu Gln Leu Ser Asn Pro Ser Arg Arg Arg Arg
865                 870                 875                 880

Phe Tyr Tyr His

<210> SEQ ID NO 11
<211> LENGTH: 671
<212> TYPE: PRT
<213> ORGANISM: Caenorhabditis elegans
<220> FEATURE:
<223> OTHER INFORMATION: HSF-1 (heat shock factor), gene Y53C10A.12

<400> SEQUENCE: 11

Met Gln Pro Thr Gly Asn Gln Ile Gln Gln Asn Gln Gln Gln Gln Gln

-continued

```
  1               5              10              15
Gln Leu Ile Met Arg Val Pro Lys Gln Glu Val Ser Val Ser Gly Ala
                 20                  25                  30

Ala Arg Arg Tyr Val Gln Gln Ala Pro Pro Asn Arg Pro Pro Arg Gln
                 35                  40                  45

Asn His Gln Asn Gly Ala Ile Gly Gly Lys Lys Ser Val Thr Ile
                 50                  55                  60

Gln Glu Val Pro Asn Asn Ala Tyr Leu Glu Thr Leu Asn Lys Ser Gly
 65                  70                  75                  80

Asn Asn Lys Val Asp Asp Lys Leu Pro Val Phe Leu Ile Lys Leu
                 85                  90                  95

Trp Asn Ile Val Glu Asp Pro Asn Leu Gln Ser Ile Val His Trp Asp
                100                 105                 110

Asp Ser Gly Ala Ser Phe His Ile Ser Asp Pro Tyr Leu Phe Gly Arg
                115                 120                 125

Asn Val Leu Pro His Phe Phe Lys His Asn Asn Met Asn Ser Met Val
                130                 135                 140

Arg Gln Leu Asn Met Tyr Gly Phe Arg Lys Met Thr Pro Leu Ser Gln
145                 150                 155                 160

Gly Gly Leu Thr Arg Thr Glu Ser Asp Gln Asp His Leu Glu Phe Ser
                165                 170                 175

His Pro Cys Phe Val Gln Gly Arg Pro Glu Leu Leu Ser Gln Ile Lys
                180                 185                 190

Arg Lys Gln Ser Ala Arg Thr Val Glu Asp Lys Gln Val Asn Glu Gln
                195                 200                 205

Thr Gln Gln Asn Leu Glu Val Val Met Ala Glu Met Arg Ala Met Arg
                210                 215                 220

Glu Lys Ala Lys Asn Met Glu Asp Lys Met Asn Lys Leu Thr Lys Glu
225                 230                 235                 240

Asn Arg Asp Met Trp Thr Gln Met Gly Ser Met Arg Gln Gln His Ala
                245                 250                 255

Arg Gln Gln Gln Tyr Phe Lys Lys Leu Leu His Phe Leu Val Ser Val
                260                 265                 270

Met Gln Pro Gly Leu Ser Lys Arg Val Ala Lys Arg Gly Val Leu Glu
                275                 280                 285

Ile Asp Phe Cys Ala Ala Asn Gly Thr Ala Gly Pro Asn Ser Lys Arg
                290                 295                 300

Ala Arg Met Asn Ser Glu Glu Gly Pro Tyr Lys Asp Val Cys Asp Leu
305                 310                 315                 320

Leu Glu Ser Leu Gln Arg Glu Thr Gln Glu Pro Phe Ser Arg Arg Phe
                325                 330                 335

Thr Asn Asn Glu Gly Pro Leu Ile Ser Glu Val Thr Asp Glu Phe Gly
                340                 345                 350

Asn Ser Pro Val Gly Arg Gly Ser Ala Gln Asp Leu Phe Gly Asp Thr
                355                 360                 365

Phe Gly Ala Gln Ser Ser Arg Tyr Ser Asp Gly Ala Thr Ser Ser
                370                 375                 380

Arg Glu Gln Ser Pro His Pro Ile Ile Ser Gln Pro Gln Ser Asn Ser
385                 390                 395                 400

Ala Gly Ala His Gly Ala Asn Glu Gln Lys Pro Asp Asp Met Tyr Met
                405                 410                 415

Gly Ser Gly Pro Leu Thr His Glu Asn Ile His Arg Gly Ile Ser Ala
                420                 425                 430
```

```
Leu Lys Arg Asp Tyr Gln Gly Ala Ser Pro Ala Ser Gly Gly Pro Ser
        435                 440                 445

Thr Ser Ser Ser Ala Pro Ser Gly Ala Gly Ala Gly Ala Arg Met Ala
    450                 455                 460

Gln Lys Arg Ala Ala Pro Tyr Lys Asn Ala Thr Arg Gln Met Ala Gln
465                 470                 475                 480

Pro Gln Gln Asp Tyr Ser Gly Gly Phe Val Asn Asn Tyr Ser Gly Phe
                485                 490                 495

Met Pro Ser Asp Pro Ser Met Ile Pro Tyr Gln Pro Ser His Gln Tyr
        500                 505                 510

Leu Gln Pro His Gln Lys Leu Met Ala Ile Glu Asp Gln His His Pro
        515                 520                 525

Thr Thr Ser Thr Ser Thr Asn Ala Asp Pro His Gln Asn Leu Tyr
    530                 535                 540

Ser Pro Thr Leu Gly Leu Ser Pro Ser Phe Asp Arg Gln Leu Ser Gln
545                 550                 555                 560

Glu Leu Gln Glu Tyr Phe Thr Gly Thr Asp Thr Ser Leu Gln Ser Phe
                565                 570                 575

Arg Asp Leu Val Ser Asn His Asn Trp Asp Asp Phe Gly Asn Asn Val
            580                 585                 590

Pro Leu Asp Asp Glu Glu Gly Ser Glu Pro Leu Arg Gln Leu
        595                 600                 605

Ala Leu Glu Asn Ala Pro Glu Thr Ser Asn Tyr Asp Gly Ala Glu Asp
    610                 615                 620

Leu Leu Phe Asp Asn Glu Gln Gln Tyr Pro Glu Asn Gly Phe Asp Val
625                 630                 635                 640

Pro Asp Pro Asn Tyr Leu Pro Leu Ala Asp Glu Glu Ile Phe Pro His
                645                 650                 655

Ser Pro Ala Leu Arg Thr Pro Ser Pro Ser Asp Pro Asn Leu Val
        660                 665                 670

<210> SEQ ID NO 12
<211> LENGTH: 200
<212> TYPE: PRT
<213> ORGANISM: Artificial Sequence
<220> FEATURE:
<223> OTHER INFORMATION: Description of Artificial Sequence:poly Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 12

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly Gly
                85                  90                  95
```

-continued

```
Gly Gly Gly Gly Gly Gly Gly Gly Gly Gly Gly Gly Gly Gly Gly
            100                 105                 110
Gly Gly Gly Gly Gly Gly Gly Gly Gly Gly Gly Gly Gly Gly Gly
        115                 120                 125
Gly Gly Gly Gly Gly Gly Gly Gly Gly Gly Gly Gly Gly Gly Gly
    130                 135                 140
Gly Gly Gly Gly Gly Gly Gly Gly Gly Gly Gly Gly Gly Gly Gly
145                 150                 155                 160
Gly Gly Gly Gly Gly Gly Gly Gly Gly Gly Gly Gly Gly Gly Gly
            165                 170                 175
Gly Gly Gly Gly Gly Gly Gly Gly Gly Gly Gly Gly Gly Gly Gly
        180                 185                 190
Gly Gly Gly Gly Gly Gly Gly Gly
    195                 200
```